US006593514B1

(12) United States Patent
Cahoon et al.

(10) Patent No.: US 6,593,514 B1
(45) Date of Patent: Jul. 15, 2003

(54) METHOD FOR THE PRODUCTION OF CALENDIC ACID, A FATTY ACID CONTAINING DELTA-8,10,12 CONJUGATED DOUBLE BONDS AND RELATED FATTY ACIDS HAVING A MODIFICATION AT THE DELTA-9 POSITION

(75) Inventors: Edgar Benjamin Cahoon, Wilmington, DE (US); William Dean Hitz, Wilmington, DE (US); Kevin G. Ripp, Wilmington, DE (US)

(73) Assignee: E. I. du Pont de Nemours and Company, Wilmington, DE (US)

( * ) Notice: Subject to any disclaimer, the term of this patent is extended or adjusted under 35 U.S.C. 154(b) by 0 days.

(21) Appl. No.: 09/638,937

(22) Filed: Aug. 15, 2000

Related U.S. Application Data
(60) Provisional application No. 60/149,050, filed on Aug. 16, 1999.

(51) Int. Cl.$^7$ .......................... A01H 5/00; C12N 15/82; C07H 21/04

(52) U.S. Cl. ...................... 800/281; 800/298; 435/69.1; 435/419; 536/23.6

(58) Field of Search .............................. 800/281, 298; 435/69.1, 419; 536/23.6

(56) References Cited

U.S. PATENT DOCUMENTS

| 4,945,050 | A | 7/1990 | Sanford et al. |
| 5,107,065 | A | 4/1992 | Shewmaker et al. |
| 5,231,020 | A | 7/1993 | Jorgensen et al. |
| 5,428,072 | A | 6/1995 | Cook et al. |
| 5,519,451 | A | 5/1996 | Clatanoff et al. |
| 5,554,646 | A | 9/1996 | Cook et al. |
| 5,851,572 | A | 12/1998 | Cook et al. |

FOREIGN PATENT DOCUMENTS

| EP | 0 242 236 B2 | 8/1996 |
| WO | 94/11516 | 5/1994 |
| WO | 00/11176 | 3/2000 |

OTHER PUBLICATIONS

De Luca, "Molecular characterization of secondary metabolic pathways", 1993, AgBiotech News and information, vol. 5 No. 6, pp. 225N–229N.*
Bork et al. "Go hunting in sequence databases but watch out for the traps", Oct. 1996, TIG vol. 12 No. 20, pp. 425–427.*
Brenner, "Errors in genome annotation", Apr. 1999, TIG, vol. 15 No. 4, pp. 132–133.*
Smith et al, The challenges of genome sequence annotation or "The devil is the details", Nov. 1997, Nature Biotechnology, vol. 15, pp1222–1223.*
Doerks et al, "Protein annotation:detective work for function prediction", Jun. 1998, TIG, vol. 14 No. 6, pp. 248–250.*

Van de Loo, "An oleate 12hydroxylase from *Ricinus communis* L. is a fatty acyl desaturase homolog", Jul. 1995, Proc. Natl. Acad. Sci., vol. 92, pp. 6743–6747.*
Broun et al, "Catalytic Plasticity of Fatty Acid Modification Enzymes Underlying Chemical Diversity of Plant Lipids", Nov. 1998, Science vol. 282, pp/ 1315–1317.*
Desmond G. Higgins et al., CABIOS Comm., vol. 5(2):1989, pp. 151–153, Fast and Sensitive Multiple Sequence Alignments on a Microcomputer.
J. M. Eggert et al., J. Anim. Sci., vol. 77(suppl):53, 1999, Effects of Conjugated Linoleic Acid on Growth and Composition of Lean Gifts.
Leslie Crombie et al., Journ. of Chem. Soc., No. 15:953–955, 1984, Origins of Conjugated Triene Fatty Acids. The Biosynthesis of Calendic Acid by Calendula Officinalis.
Mary J. Chisholm et al., Can. Journ. of biochem., vol. 45:251–253, 1967, Calendic Acid in Seed Oils of the Genus Calendula.
L. J. Morris et al., Chem. & Ind., pp. 1493–1494, 1966, Occurrence of cis, trans–Linoleic Acid in Seed Oils.
Yuji Ishida et al., Nature Biotech., vol. 14:745–750, 1996, High efficiency transformation of maize (*Zea mays* L.) mediated by *Agrobacterium tumefaciens*.
William D. Hitz et al., Plant Phys., vol. 105:635–641, 1994, Cloning of a Higher–Plant Plastid w–6 Fatty Acid Desaturase cDNA and its Expression in a Cyanobacterium.
Gary Dobson, JAOCS, vol. 75(2):137–142, 1998, Identification of Conjugated Fatty Acids by Gas Chromatography-Mass Spectrometry of 4–Methyl–1,2,4–triazoline–3,5–dione Adducts.
Linsen Liu et al., Plant Phys., vol. 113:1343–1349, 1997, In vivo studies of the Biosynthesis of alpha–Eleostearic Acid in the Seed of *Momordica charantia* L..
Stephen G. Rogers et al., Methods in Enzymol., vol. 118:627–641, 1986, Gene Transfer in Plants: Production of Transformed Plants Using Ti Plasmid Vectors.
Michael Lee et al., Science, vol. 280:915–918, 1998, Identification of Non–Heme Diiron Proteins that Catalyze Triple Bond and Epoxy Group Formation.
R. G. Binder et al., Journ. of Amer. Oil Chemists Soc., vol. 41:108–110, 1964, Chromatographic Analysis of Seed Oils. II. Fatty Acid Composition of Dimorphotheca Oil.

(List continued on next page.)

Primary Examiner—Elizabeth F. McElwain

(57) ABSTRACT

The preparation and use of nucleic acid fragments encoding plant fatty acid modifying enzymes associated with modification of the delta-9 position of fatty acids, in particular, formation of conjugated double bonds are disclosed. Chimeric genes incorporating such nucleic acid fragments and suitable regulatory sequences can be used to create transgenic plants having altered lipid profiles. The preparation and use of nucleic acid fragments encoding plant fatty acid modifying enzymes associated with formation of a trans delta-12 double bond also are disclosed. Chimeric genes incorporating such nucleic acid fragments and suitable regulatory sequences can be used to create transgenic plants having altered lipid profiles.

15 Claims, 13 Drawing Sheets

OTHER PUBLICATIONS

Figure 1:
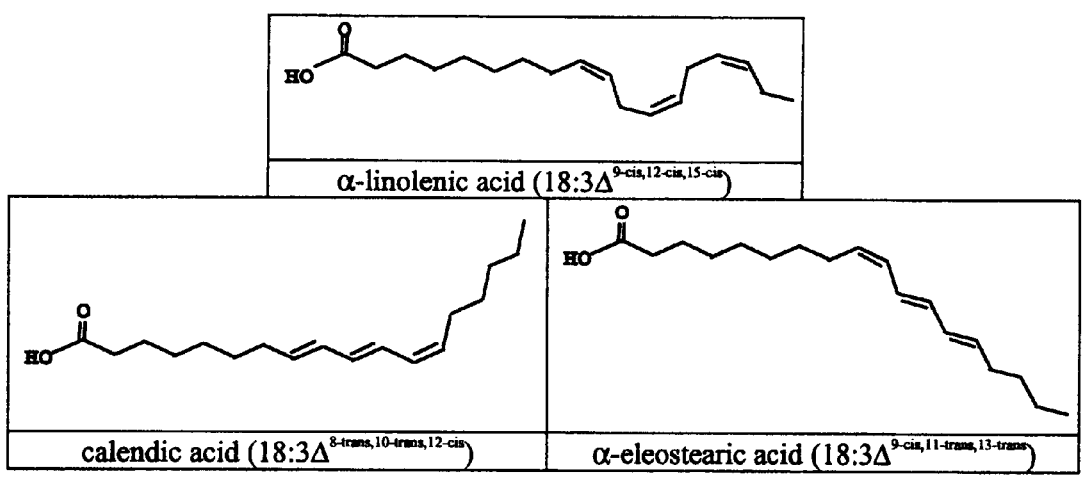

M. O. Bagby et al., Lipids, vol. 1(4):263–267, 1965, Stereochemistry of alpha–Parinaric Acid from Impatiens edgeworthii Seed Oil.

R. C. Badami et al., Prog. Lipid. Res., vol. 19:119–153, 1981, Structure and Occurrence of Ususual Fatty Acids in Minor Seed Oils.

L. J. Morris et al., Journ. of Amer. Oil Chem. Soc., vol. 37:323–327, 1960, Vicinally Unsaturated Hydroxy Acids in Seed Oils.

Leslie Crombie et al., J. Chem. Soc. Perkin Trans. I:2425–2434, 1985, The Biosynthesis of Calendic Acid, Octadeca–(8E, 10E, 12Z)–trienoic Acid, by Developing Marigold Seeds: Origins of (E,E,Z) and (Z,E,Z) Conjugated Triene Acids in Higher Plants.

Edgar B. Cahoon et al., PNAS, vol. 96:22:12935–12940, 1999, Biosynthetic origin of conjugated double bonds: Production of fatty acid commponents of high–value drying oils in transgenic soybean embroys.

National Center for Biotechnology Information General Identifier No. 4378875, Jul. 21, 2000, Marillia, E. F. et al., Cloning and Nucleotide Sequencing of a cDNA Encoding a *Brassica carinata* FAD2.

Elizabeth–France Marillia et al., Plant Gene Register PGR 99–068, Plant Phys., vol. 120(1):339, 1999, Cloning and Nucleotide Sequencing of a cDNA Encoding a *Brassica carinata* FAD2.

National Center for Biotechnology Information General Identifier No. 3417601, Aug. 13, 1998, Sayanova, O. et al., Fatty Acid Desaturases from Borage.

National Center for Biotechnology Information General Identifier No. 3334184, Jul. 15, 1998, Singh, S.P. et al., Nucleotide sequence of a cDNA from *Brassica juncea* Encoding a Microsomal Omega–6 Desaturase.

National Center for Biotechnology Information General Identifier No. 2501790, Oct. 8, 1997, Kirsch, C. et al., Rapid and transient induction of a parsley microsomal delta 12 fatty acid desaturase mRNA by fungal elicitor.

Christoph Kirsch et al., Plant Phys., vol. 115:283–289, 1997, Rapid and Transient Induction of a Parsley Microsomal alpha–12 Fatty Acid Desaturase mRNA by Fungal Elicitor.

Athel Cornish–Bowden, Nucleic Acids Res., vol. 13(9):1985, Nomenclature for Incompletely Specified Bases in Nucleic Acid Sequences.

Natasha Raikhel, Plant Phys., vol. 100:1627–1632, 1992, Nuclear Targeting in Plants.

Kenneth Keegstra, Cell, vol. 56:247–253, 1989, Transport and Routing of Proteins into Chloroplasts.

Stephen F. Altschul et al., J. Mol. Biol., vol. 215:403–410, 1990, Basic Local Alignment Search Tool.

Maarten J. Chrispeels, Annu. Rev. Plant Phys. Plant Mol. Biol., vol. 42:21–53, 1991, Sorting of Proteins in the Secretory System.

Michael A. Frohman et al., Journ. of Methods in Cell & Mol. Biol., vol. 1(3):165–170, 1989, Rapid Amplification of cDNA Ends Using Nested Primers.

Osamu Ohara et al., PNAS, vol. 86:5673–5677, 1989, One–sided Polymerase Chain Reaction: The amplification of cDNA.

Chu et al., Sci. Sin. Peking, vol. 18:659–668, 1975, The Important role of Historical Flood Data in the Estimation of Spillway Design Floods.

Ivan L. W. Ingelbrecht et al., The Plant Cell, vol. 1:671–680, 1989, Different 3' End Regions Strongly Influence the Level of Gene Expression in Plant Cells.

Jack K. Okamuro et al., Biochemistry of Plants, vol. 15:1–82, Regulation of Plant Gene Expression: General Principles.

Roisin Turner et al., Mol. Biotech., vol. 3:225–236, 1995, The Potential Exploitation of Plant Viral Translational Enhancers in Biotechnology for Increased Gene Expression.

IUPAC–IUB Joint Commission on Biochemical Nomenclature (JCBN), Biochem. J., vol. 219:345–373, 1984, Nomenclature & Symbolism for Amino Acids and Peptides.

John B. Ohlrogge et al., Plant Phys., vol. 104:821–826, 1994, Design of New Plant Products: Engineering of Fatty Acid Metabolism.

Warren Gish et al., Nature Genetics, vol. 3:266–272, 1993, Identification of Protein Coding Regions by Database Similarity Search.

John Shanklin et al., Biochem., vol. 33:12787–12794, 1994, Eight Histidine Residues are Catalytically Essential in a Membrane–Associated Iron Enzyme, Stearoyl–CoA Desaturase, and Are Conserved in Alkane Hydroxylase and Xylene Monooxygenase.

Frank J. Van De Loo et al., PNAS, vol. 92:6743–6747, 1995, An Oleate 12–hydroxylase from *Ricinus communis L.* is a fatty acyl desaturase homolog.

Faith C. Belanger et al., Plant Phys., vol. 91:636–643, 1989, Molecular Characterization of the Major Maize Embryo Globulin Encoded by the Glb1 Gene.

Michael E. Fromm et al., Biotech., vol. 8:833–839, 1990, Inheritance and Expression of Chimeric Genes in the Progeny of Transgenic Maize Plants.

R. N. Beachy et al., EMBO J., vol. 4(12):3047–3053, 1985, Accumulation and Assembly of Soybean beta–conglycinin in Seeds of Transformed Petunia Plants.

Jonathan D. G. Jones et al., EMBO J., vol. 4(10):2411–2418, 1985, High Level Expression of Introduced Chimaeric Genes in Regenerated Transformed Plants.

Elionor R. P. De Almeida et al., Mol. Gen. Genet., vol. 218:78–86, 1989, Transgenic Expression of Two Marker Genes under the Control of an Arabidopsis rbcS promoter: Sequences encoding the Rubisco transit peptide increase expression levels.

T. M. Klein et al., Nature, vol. 327:70–73, 1987, High–velocity microprojectiles for delivering nucleic acids into living cells.

Michael A. Frohman et al., PNAS, vol. 85:8998–9002, 1988, Rapid Production of full–length rare transcripts: Amplification using a single oligonucleotide primer.

Elwyn Y. Loh et al., Science, vol. 243:217–220–, 1989, Polymerase Chain Reaction with Single–Sided Specificity: Analysis of T C Receptor 8 Chain.

Nancy H. Wallace et al., Plant Phys., vol. 95:973–975, 1991, Nucleotide Sequence of a cDNA Clone Corresponding to the Maize Globulin–2 Gene.

Joan T. Odell et al., Nature, vol. 313:810–812, 1985, Identification of DNA sequences required for activity of the cauliflower mosaic virus 35S Promoter.

Mark D. Adams et al., Science, vol. 252:1651–1656, 1991, Complementary DNA Sequencing: Expressed Sequence Tags and Human Genome Project.

M. D. Chisholm et al., Can. Journ. of Biochem., vol. 42:1033–1040, 1964, Biosynthesis of Mustard Oil Glucosides.

R. C. Thiel et al., J. Anim. Sci., vol. 77(suppl):47, 1998, Effects of CLA supplementation on quality and sensory characteristics of pork.

R. C. Wiegand et al., J. Anim. Sci., vol. 77(suppl):47, 1999, Effects of CLA supplementation on pork quality characteristics in crossbred growing–finishing barrows.

Linda Gritz et al., Gene, vol. 25: 179–188, 1983, Plasmid–encoded hygromycin B resistance: the sequence of hygromycin B phosphotransferase gene and its expression in *Escherichia coli* and *Saccharomyces cerevisiae*.

Mats Hamberg et al., Biochem. & Biophys. Res. Comm., vol. 188(3):1992, Metabolism of 6,9,12–Octadecatrienoic acid in the red alga lithothamnion corallioides: Mechanism of formation of a conjugated tetraene fatty acid.

Edgar B. Cahoon et al., J. Biol. Chem., vol. Manuscript Moo9188200, No. in press, 2000, pp. 1–27, Formation of conjugated delta 8, delta 10 double bonds by delta 12–oleic acid desaturase related enzymes: Biosynthetic origin of calendic acid.

Kathrin Fritsche et al., FEBS Lett., vol. 462:249–253, 1999, Isolation and characterization of a calendic acid producing (8,11)–linoleoyl desaturase.

* cited by examiner-

FIGURE 2A

```
SEQ ID NO:15  MGGGGRMPVPTKGKKSKSDVFQ------------RVPSEKPPFTVGDLKKVIPPHCFQRSVLHSFSYVVYD
SEQ ID NO:13  MGASEEM-KVLE-------------------RVPVSKPPFEYNDLKKAVPPHCFTRSLSLSFYYLFYD
SEQ ID NO:6   MGGGGRMSTVITSNNSEKKG--GSS--HLKRAPHTKPPFTLGDLKRAIPPHCFERSFVRSFSYVAYD
SEQ ID NO:7   MGEVGPTNR--TKTKLDKQQESEN-----RVPHEPPPFTLSDLKKAIPPHCFERSLVKSFYHVIHD
SEQ ID NO:8   MGGRGAIGVLRNGGGPKKKMGPGQGLGPGERITHARPPFSISQIKKAIPPHCFQRSLRRSFSYLLSD
SEQ ID NO:9   MGAGGQKTFPRLEEEEKQQQAAAAGF---KRIPTTKPPFTLSDLKKAIPPHCFQRSLLRSFSYVFID
SEQ ID NO:5   MGLA-KETTMGGRGRVAKVEVQGKK--PLSRVPNTKPPFTVGQLKKAIPPHCFQRSLLTSFSYVVYD
SEQ ID NO:2   MGKGASNKKVLE--------------------RVPITKPPFEYNDLKKAVPPHCFSRPLFRSFYFLLHD
SEQ ID NO:4   MGKAASAKKVLE--------------------RVPISKPPFEYNDLKKAVPPHCFSRPLSRSLYFLFHD
SEQ ID NO:14  MGAGEYTSV-T----NENNPLD---------RVPHAKPPFTIGDLKKAIPPHCFQRSLTRSFSYVLSD
SEQ ID NO:11  MGAGGCISV-SETKPNQKNSLE---------RAPYDKPPFTISDLKKAIPPHLFKRSLIRSLSYVASD

*
SEQ ID NO:15  LVIAALFFYTASRYIHLQPHPL-SYVAWPLYWFCQGSVLTGVWVIA H ECG H HAFSDYQWLDDT
SEQ ID NO:13  LIKVCILFYVASKYIPMLPYSL-SCIWPLYWFFQGAFLGRLWMIG H ECG H HSFSNYRWLDDT
SEQ ID NO:6   VCLSFLFYSIATNFFPYISSPL-SYVAWLVYWLFQGCILTGLWVIG H ECG H HAFSEYQLADDI
SEQ ID NO:7   IIILSFFYVAANYIPMLPQNL-RYVAWPIYWAIQGCVQLGILVLG H ECG H HAFSDYQWVDDM
SEQ ID NO:8   IALVSAFYYVADTYFHRLPHPLLHYLAWPVYWFCQGAVLTGMWGIA H DCG H HAFSDYQLVDDV
SEQ ID NO:9   LTIISILGYIGATYICLLPPPS-KYLAWLLYWAVQGCFFTGAWALA H DCG H HAFSDYQWIDDA
SEQ ID NO:5   LSFAFIFY-IATTYFHLLPQPF-SLIAWPIYWVLQGCLLTGVWVIA H ECG H HAFSKYQWVDDV
SEQ ID NO:2   IIVTCILFYVASNYIPMLPGFL-SYIVWPVYWISQGVFLGRLWMIG H ECG H HSFSNYRWVDDS
SEQ ID NO:4   IIVTCILFYVASNYIHMLPRFL-SCIVWPVYWISQGVFLGRLWMIG H ECG H HSFSNYRWVDDT
SEQ ID NO:14  LTITAVLYHIATTYFHHLPTPL-SSIAWASYWVVQGCVLTGVWVIA H ECG H HAFSDYQWVDDT
SEQ ID NO:11  LTVAFLLYH-ATTYFHHLPQPF-TALAWLAYWVAQGCVLTGVWVIG H ECG H HGLSEYRGVDDT
```

FIGURE 2B

```
SEQ ID NO:15  VGLLLHSALLVPYFSWKYS H RR HH SNTGSLERDEVFVPKKRSGISWS--SEYL-NNPPGRVLV
SEQ ID NO:13  VGFLVHTATLTPYFSFKYS H RN HH AHTNSLEYDEVHVPKIRKFKSEHLYSEFLTNNPFGLVVN
SEQ ID NO:6   VGLIVHSALLVPYFSWKYS H RR HH SNIGSLERDEVFVPKSKSKISWY--SKYS-NNPPGRVLT
SEQ ID NO:7   VGFVLHSSQLIPYFSWKHS H RR HH SNTASIERDEVYPPAYKNDLPWF--AKYL-RNPVGRFLM
SEQ ID NO:8   VGFLIHSLVFVPYFSFKIS H RR HH SNTSSVDRDEVFVPKPKAKMPWY--FKYL-TNPPARVFI
SEQ ID NO:9   VGMVLHSTLMVPYFSFKYS H RR HH SNINSLERDEVFVPRPKSKIKWYC-SKYL-NNPLGRVLT
SEQ ID NO:5   VGLTLHSTLLVPYFSWKIS H RR HH SNTGSLDRDEVFVPKPKSKVAWF--SKYL-NNPLGRAVS
SEQ ID NO:2   VGFLIHTATLTPYFSFKYS H RN HH AHTNSMEYDEVHIPKRKSEALDLY-FEFLGNNPMGLMIT
SEQ ID NO:4   VGFLIHTATLTPYFSFKYS H RN HH AHTNSMEYDEVHIPKRKSEAL--Y-FEFLGNNPIGLMIT
SEQ ID NO:14  VGFVLHSSLLVPYFSWKYS H HR HH SNTGSLERDEVFVPKSRSKVPWY--SKYF-NNTVGRIVS
SEQ ID NO:11  VGYILHSSLLVPYFSWKYS H RR HH SNTGSLDRDEVFVPKPRSKISWY--SKYF-NNPVGRIGV

SEQ ID NO:15  LLVQLTLGWPLYLMFNVSGRPYDR--FACHFDPKSPIYNDRERLQIYISDAGIVAVMYGLYRLVAAK
SEQ ID NO:13  MVFELTFGYPSYLIFNYSGRKLTQAGFASHLYPQSPIFNDSERNHVFFSDVGICIVLYALYRIAIAK
SEQ ID NO:6   LAATLLLGWPLYLAFNVSGRPYDR--FACHYDPYGPIFSERERLQIYIADLGIFATTFVLYQATMAK
SEQ ID NO:7   IFGALLFGWPSYLLFNANGRLYDR--FASHYDPQSPIFNNRERLQVIASDVGLVFAYFVLYKIALAK
SEQ ID NO:8   IFITLTLGWPMYLTFNISGRYYGR--FTSHFDPNSPIFSPKERVLVHISNAGLVATGYLLYRIAMAK
SEQ ID NO:9   LAVTLILGWPMYLALNASGRDYDR--FVSHFYPYGPIYNDRERLQIYISDAGIFIVSYVLYQVALAK
SEQ ID NO:5   LLVTLTIGWPMYLAFNVSGRPYDS--FASHYHPYAPIYSNRERLLIYVSDVALFSVTYSLYRVATLK
SEQ ID NO:2   MLCKLTFGYAAYIMFNYTGKKHKSGGLASHFYPQSPLFNDSERNHVLFSDVGICIVLYACYRIVMVT
SEQ ID NO:4   MLCKLTFGYAAYIMFNYTGKKHKSGGLASHFYPQSPLFNDSERNHVLFSDIGICIVLYACYRIVTVT
SEQ ID NO:14  MFVTLTLGWPLYLAFNVSGRPYDR--FACHYVPTSPMYNERKRYQIVMSDIGIVITSFILYRVAMAK
SEQ ID NO:11  LFITLTLGWPLYLTFNVSGRPYDR--FACHYSPNSPIYNNRERFQIYLSDIGIVITSLVLLRAAMVK
```

FIGURE 2C

```
SEQ ID NO:15    GVAWVVCYYGVPLLVVNGFLVLITYLQHTQPSLPHYDSSEWDWLKGALATVDRDYGFLNKVLH-NIT
SEQ ID NO:13    GAMLVLYVYGLPWVVMSAFIFSLTYLQHTHPSIPHYDSTEWNWLRGALSSIDRE--LAGAFNIKKT
SEQ ID NO:6     GLAWVMRIYGVPLLIVNCFLVMITYLQHTHPAIPRYGSSEWDWLRGAMVTVDRDYG-VLNKVFHNIA
SEQ ID NO:7     GFVWLICVYGVPYVILNGLIVLITFLQHTHPNLPRYDLSEWDWLRGALSTVDRDYG-MLNKVFHNVT
SEQ ID NO:8     GVGWLIRLYGVPLIVLNACVVLITALQHTHPSFPYYDSTEWDWLRGNLVTVDRDYGPIMNRVFHHIT
SEQ ID NO:9     GLPWLICIYGVPLFVNNALVVTITYLQHTHPELPRYGNSEWDWFKGTLATVDRDMGPLLNWATHHVS
SEQ ID NO:5     GLVWLLCVYGVPLLIVNGFLVTITYLQHTHPDSSEWDWLKGALATMDRDYG-ILNKVFHHIT
SEQ ID NO:2     GAMSAFYVYGIPWVIMSAILFAATYLQHTHPSIPHYDTTEWNWLRGALSTIDRD---LGFFNMNKT
SEQ ID NO:4     GAMPAFYVYGIPWVIMSAILFAATYLQHTHPSIPHYDTTEWNWLRGALSTIDRD---LGFFNMNKT
SEQ ID NO:14    GLVWICVYGVPLMVVNAFLVLITYLQHTHPGLPHYDSSEWEWLKGALATVDRDYG-VLNKVFHHIT
SEQ ID NO:11    GLVWLICVYGVPLMITNGFLVLVTYLQHTHPSLPHYDNSEWEWLKGALVTVDRDFG-VLNTVFHHAT

SEQ ID NO:15    DT  H  VA  HH    LFSTMPHYHAMEATKAIKPILGDYYQCDRTPVFKAMYREVKECIYVEADE------
SEQ ID NO:13    HY  H  VV  HH    LFPFIPEYHAHDATEALKPILGPYYKYDGTPFYKALWREMKDCLYVESDD------
SEQ ID NO:6     DT  H  VA  HH    LFATVPHYHAMEATKAIKPIMGEYYRYDGTPFYKALWREAKECLFVEPDE------
SEQ ID NO:7     DT  H  LV  HH    LFTTMPHYRAKEATEVIKPILGDYYKFDDTPFLKALWKDMGKCIYVESDV------
SEQ ID NO:8     DT  H  YV  HH    LFPSMPHYNGKEATVAAKRILGEYYQFDGTPIWKAAWREFRECVYVEPDEDDGATS
SEQ ID NO:9     DT  H  VA  HH    LFSTMPHYHGVEATKAVKPMLGEYYRFDPTPLYKALWREAKECLFVEPDS------
SEQ ID NO:5     DT  H  VA  HH    LFSTMPHYHAMEATNAIKPILGEYYQFDDTPFYKALWREARECLYVEPDE------
SEQ ID NO:2     HY  H  VI  HH    LFPVIPEYHAQEATEAIKPILGQYYYKYDGTPFLKALWREMKDCIYVESDQ------
SEQ ID NO:4     HY  H  VI  HH    LFPVIPEYHAQEATEAIKPILGQYYKYDGTPFLKALWREMKECIYVESDE------
SEQ ID NO:14    DT  H  VV  HH    LFSTMPHYNAMEAQKALRPVLGEYYRFDKTPFYVAMWREMKECLFVEQDDEG----
SEQ ID NO:11    DG  H  IV  HH    LFPTIPHYNAMEATKAVKPLMGEYYQYDATPFYVAMWREAKECLFVDRDEGE----
```

FIGURE 2D

| | | |
|---|---|---|
| SEQ ID NO:15 | GDNKKGVFWYKNKL | Borage |
| SEQ ID NO:13 | GPNKTGVYWFKTKT | DMFad2-2 |
| SEQ ID NO:6 | GAPTQGVFWYRNKY | Hydroxylase |
| SEQ ID NO:7 | PGKNKGVYWYNNDI | ImpFad2H8 |
| SEQ ID NO:8 | GSSSKGVFWYHNKL | MomFad2 |
| SEQ ID NO:9 | --KSPGVFWFDKF | ChrFad2 |
| SEQ ID NO:5 | GTSEKGVYWYRNKY | soy omega-6 |
| SEQ ID NO:2 | GQKKQGIYWFKNKI | CalFad2-1 |
| SEQ ID NO:4 | GQKKQGIYWFKNKT | CalFad2-2 |
| SEQ ID NO:14 | --KGGVFWYKNKMN | Sunflower |
| SEQ ID NO:11 | --KGGVFWYKNKM | DMFad2-1 |

METHOD FOR THE PRODUCTION OF CALENDIC ACID, A FATTY ACID CONTAINING DELTA-8,10,12 CONJUGATED DOUBLE BONDS AND RELATED FATTY ACIDS HAVING A MODIFICATION AT THE DELTA-9 POSITION

This application claims priority benefit of U.S. Provisional Application No. 60/149,050 filed Aug. 16, 1999, now abandoned.

FIELD OF THE INVENTION

This invention relates to fatty acid biosynthesis and, in particular, to the preparation and use of nucleic acid fragments encoding plant fatty acid modifying enzymes associated with modification of the delta-9 position of fatty acids and, in particular, formation of conjugated double bonds. Chimeric genes incorporating such nucleic acid fragments and suitable regulatory sequences can be used to create transgenic plants having altered lipid profiles. This invention also relates to the preparation and use of nucleic acid fragments encoding plant fatty acid modifying enzymes associated with the formation of a trans-delta-12 double bond. Chimeric genes incorporating such nucleic acid fragments and suitable regulatory sequences can be used to create transgenic plants having altered lipid profiles.

BACKGROUND OF THE INVENTION

Fatty acids bearing chemical modifications in addition to the common double bonds are found in the storage lipids of many oilseeds (Badami and Patil (1981) *Prog. Lipid Res.* 19:119–153). Some of these modifications functionalize the fatty acid to produce products that are useful in industrial applications; this is an alternative to the more common usage of plant-derived lipids as foods. Examples are the use of the hydroxylated fatty acid ricinoleic acid in lubricants, and the short- or medium-carbon chain length fatty acids from palm oil in detergents. In some cases, fatty acid composition of the storage lipids of oilseeds produced in temperate climates can be modified by the addition of genes from exotic sources so that large amounts of unique fatty acids are produced (Ohlrogge, J. B. (1994) *Plant Physiol.* 104, 821–826).

Fatty acids containing conjugated double bonds are major components of the seed oil of a limited number of plant species. For example, calendic acid (8-trans, 10-trans, cis-12-octadecatrienoic acid) composes greater than 50% of the total fatty acids of the seed oil of *Calendula officinalis* (Crombie and Holloway (1984) *J. Chem. Soc. Chem. Commun.* 15, 953–955, Chisholm, M. J. & Hopkins, C. Y. (1967) *Can. J. Biochem* 45:251–254). Another example, α-parinaric acid (9-cis, 11-trans, 13-trans, 15-cis-octadecatetraenoic acid) and β-parinaric acid (9-trans, 11-trans, 13-trans, 15-cis-octadecatetraenoic acid) compose more than 25% of the total fatty acids of the seed oil of Impatiens species (Bagby, M. O., Smith, C. R. and Wolff, I. A. (1966) *Lipids* 1, 263–267). In addition, α-eleostearic acid (9-cis, 11-trans, 13-trans-octadecatrienoic acid) and β-eleostearic acid (9-trans, 11-trans, 13-trans-octadecatrienoic acid) compose >55% of the total fatty acids of the seed oil of *Momordica charantia* (Chisolm, M. J. and Hopkins, C. Y. (1964) *Can. J. Biochem.* 42, 560–564; Liu, L., Hammond, E. G. and Nikolau, B. J. (1997) *Plant Physiol.* 113, 1343–1349). Calendic acid and eleostearic acid are both 18:3 fatty acids, like linolenic acid, however, their structures are quite different, as shown in FIG. 1. Another fatty acid containing conjugated double bonds is found in the seeds of *Dimorphotheca sinuata*. This unusual $C_{18}$ fatty acid, dimorphecolic acid (9-OH-18:2$\Delta^{10trans,12trans}$), contains two conjugated trans-double bonds between the $\Delta^{10}$ and $\Delta^{11}$ carbon atoms and between the $\Delta^{12}$ and $\Delta^{13}$ carbon atoms as well as a hydroxyl group on the $\Delta^9$ carbon atom [Binder, R. G. et al., (1964) *J. Am. Oil Chem. Soc.* 41:108–111; Morris, L. J. et al., (1960)*J. Am. Oil Chem. Soc.* 37:323–327]. Thus, there are certain 18:2 and 18:3 plant fatty acids that contain conjugated double bonds.

The presence of conjugated double bonds in fatty acids provides the functional basis for drying oils such as tung oil that are enriched in isomers of eleostearic acid. This is due largely to the fact that fatty acids with conjugated double bonds display high rates of oxidation, particularly when compared to polyunsaturated fatty acids with methylene interrupted double bonds. Drying oils, such as tung oil, are used as components of paints, varnishes, and inks.

Conjugated fatty acids can also be used as an animal feed additive. Conjugated linoleic acids (CLAs, 18:2) have been used to improve fat composition in feed animals.

U.S. Pat. No. 5,581,572, issued to Cook et al. on Dec. 22, 1998, describes a method of increasing fat firmness and improving meat quality in animals using conjugated linoleic acds.

U.S. Pat. No. 5,554,646, issued to Cook et al. on Sep. 10,1996, describes a method of reducing body fat in animals using conjugated linoleic acids.

U.S. Pat. No. 5,519,451, issued to Cook et al. on Jul. 6, 1999, describes a method of improving the growth or the efficiency of feed conversion of an animal which involves animal feed particles having an inner core of nutrients and an outer layer containing a conjugated fatty acid or an antibody that can protect the animal from contacting diseases that can adversely affect the animal's ability to grow or efficiently convert its feed into body tissue.

U.S. Pat. No. 5,428,072, issued to Cook et al. on Jun. 27, 1995, describes a method of enhancing weight gain and feed efficiency in animals, which involves the use of conjugated linoleic acid.

The mechanism by which these effects are realized is not known. It is believed that no one heretofore has discussed the use of conjugated 18:3 fatty acids (conjugated linolenic acids or ClnAs), for improving animal carcass characteristics.

The biosynthesis of fatty acids with conjugated double bonds is not well understood. Several reports have indicated that conjugated double bonds are formed by modification of an existing double bond (Crombie, L. and Holloway, S. J. (1985) *J. Chem. Soc. Perkins Trans. I* 1985, 2425–2434; Liu, L., Hammond, E. G. and Nikolau, B. J. (1997) *Plant Physiol.* 113, 1343–1349). For example, the double bonds at the 11 and 13 carbon atoms in eleostearic acid have been shown to arise from the modification of the $\Delta^{12}$ double bond of linoleic acid (18:2$\Delta^{9,12}$) (Liu, L., Hammond, E. G. and Nikolau, B. J. (1997) *Plant Physiol.* 113, 1343–1349). The exact mechanism involved in conjugated double formation in fatty acids, however, has not yet been determined. Fatty acid desaturase (Fad)-related enzymes are responsible for producing 18:3$\Delta^{9,11,13}$ oils such as α and β-eleostearic acid and 18:4$\Delta^{9,11,13,15}$ oils such as α and β-parinaric acid in Impatiens, Momordica, and Chrysobalanus. Insertion of a chimeric gene comprising an isolated nucleic acid fragment encoding these enzymes into species that do not normally accumulate conjugated double-bond containing; fatty acids resulted in production of eleostearic and/or parinaric acids (Cahoon et al. (1999) *Proc. Natl. Acad. Sci. USA* 96:12935–12940; and WO 00/11176, published on Mar. 2, 2000, the disclosure of which is hereby incorporated by reference). The present invention extends this work by answering whether 18:3$\Delta^{8,10,12}$ fatty acids like calendic or dimorphecolic acids can also be produced in transgenic plants. Unlike the Fad-related enzymes that modify the delta-12 position to produce eleostearic and parinaric acids, the enzymes of the present invention (with one exception as is discussed below with respect to DMFad2-1) modify the delta-9 position of fatty acids to produce calendic and dimorphecolic acids. One enzyme is disclosed herein which is associated with the formation of a trans-delta-12 double bond. The product of this enzymatic reaction then becomes the substrate for a reaction involving conjugated double bond formation comprising a delta-9 position of fatty acids. Isolation and characterization of two Calendula cDNAs, two Dimorphotheca cDNAs, and expression of a chimeric transgene, are described herein.

SUMMARY OF THE INVENTION

This invention concerns an isolated nucleic acid fragment encoding a plant fatty acid modifying enzyme associated with conjugated double bond formation comprising a delta-9 position of fatty acids wherein said fragment or a functionally equivalent subfragment thereof (a) hybridizes to any of the nucleotide sequences set forth in SEQ ID NOs:1, 3, or 12 under conditions of moderate stringency or (b) is at least 40% identical to a polypeptide encoded by any of the nucleotide sequences set forth in SEQ ID NOs:1, 3, or 12 or a functionally equivalent subfragment thereof as determined by a comparison method designed to detect homologous sequences.

In a second aspect, this invention concerns an isolated nucleic acid fragment encoding a plant fatty acid modifying enzyme associated with conjugated double bond formation comprising a delta-9 position of fatty acids wherein said fragment, or a functionally equivalent subfragment thereof, encodes a protein comprising any one of the amino acid sequences set forth in SEQ ID NOs:2, 4, or 13.

In a third aspect, this invention concerns a chimeric gene comprising such isolated nucleic acid fragments, or a functionally equivalent subfragment thereof, or a complement thereof, operably linked to suitable regulatory sequences.

In a fourth aspect, this invention concerns a transformed host cell or plant comprising such a chimeric gene.

In a fifth aspect, this invention concerns a method of altering the level of fatty acids in a host cell or plant wherein said fatty acids comprise a modification at a delta-9 position, said method comprising:

(a) transforming a host cell or plant with a chimeric gene as discussed above;

(b) growing the transformed host cell or plant under conditions suitable for the expression of the chimeric gene; and (c) selecting those transformed host cells or plants having altered levels of fatty acids with double bonds.

In a sixth aspect, this invention concerns a method for producing seed oil containing fatty acids comprising a modified delta-9 position in the seeds of plants which comprises:

(a) transforming a plant cell with such a chimeric gene;

(b) growing a fertile mature plant from the transformed plant cell of step (a);

(c) screening progeny seeds from the fertile plants of step (b) for altered levels of fatty acids comprising a modified delta-9 position; and (d) processing the progeny seed of step (c) to obtain seed oil containing altered levels of plant fatty acids comprising a modified delta-9 position.

In a seventh aspect, this invention concerns a method for producing plant fatty acid modifying enzymes associated with modification of a delta-9 position of fatty acids which comprises:

(a) transforming a microbial host cell with the claimed chimeric genes;

(b) growing the transformed host cell under conditions suitable for the expression of the chimeric gene; and (c) selecting those transformed host cells containing altered levels of protein encoded by the chimeric gene.

In an eighth aspect, this invention concerns a method to isolate nucleic acid fragments and functionally equivalent subfragments thereof encoding a plant fatty acid modifying enzyme associated with modification of a delta-9 position of fatty acids comprising:

(a) comparing SEQ ID NOs:2, 4, or 13 and other plant fatty acid modifying enzyme polypeptide sequences;

(b) identifying conserved sequences of 4 or more amino acids obtained in step (a), (c) designing degenerate oligomers based on the conserved sequences identified in step (b); and (d) using the degenerate oligomers of step(s) to isolate sequences encoding a plant fatty acid modifying enzyme or a portion thereof associated with modification of the delta-9 position of fatty acids by sequence dependent protocols.

In an ninth aspect, this invention concerns an isolated nucleic acid fragment encoding a plant fatty acid modifying enzyme wherein said enzyme modifies a delta-9 position of fatty acids and further wherein said fragment or a functionally equivalent subfragment thereof (a) hybridizes to any of the nucleotide sequences set forth in SEQ ID NOs:1, 3, or 12 under, conditions of moderate stringency or (b) is at least 40% identical to a polypeptide encoded by any of the nucleotide sequences set forth in SEQ ID NOs:1, 3, or 12 or a functionally equivalent subfragment thereof as determined by a comparison method designed to detect homologous sequences.

In an tenth aspect, this invention concerns an isolated nucleic acid fragment encoding a plant fatty acid modifying enzyme wherein said enzyme modifies a delta-9 position of fatty acids and further wherein said fragment or a functionally equivalent subfragment thereof encodes a protein comprising any one of the amino acid sequences set forth in SEQ ID NOs:2, 4, or 13.

In a eleventh aspect, this invention concerns isolated nucleic acid fragment encoding a plant fatty acid modifying enzyme wherein said enzyme modifies a delta-9 position of fatty acids wherein said fragment or a functionally equivalent subfragment thereof (a) hybridizes to the isolated nucleic acid fragment of claim 2 under conditions of moderate stringency or (b) is at least 40% identical to a polypeptide encoded by any of the isolated nucleic acid fragments of claim 2 or a functionally equivalent subfragment thereof as determined by a comparison method designed to detect homologous sequences.

Also of interest are chimeric genes comprising such isolated nucleic acid fragments, or a functionally equivalent subfragment thereof, or a complement thereof, operably linked to suitable regulatory sequences. Transformed host cells or plants comprising such chimeric genes are of interest. Indeed, these nucleic acid fragments can be used in any of the above-identified methods such as altering the level of fatty acids in a host cell or plant, producing plant fatty acid modifying enzymes associated with modification of a delta-9 position of a fatty acid, etc.

In a twelfth aspect, this invention concerns an animal feed comprising an ingredient derived from the processing of any of the seeds obtained from plants transformed with the chimeric genes discussed herein and a method of improving the carcass quality of an animal by supplementing the diet of the animal with such animal feeds.

In a thirteenth aspect, this invention concerns an isolated nucleic acid fragment encoding a plant fatty acid modifying enzyme associated with the formation of a trans delta-12 double bond wherein said enzyme modifies a delta-12 position of fatty acids and further wherein said fragment or a functionally equivalent subfragment thereof (a) hybridizes to any of the nucleotide sequences set forth in SEQ ID NO:10 under conditions of moderate stringency or (b) is at least 75% identical to a polypeptide encoded by any of the nucleotide sequences set forth in SEQ ID NO:10 or a functionally equivalent subfragment thereof as determined by a comparison method designed to detect homologous sequences.

Also of interest are chimeric genes comprising such isolated nucleic acid fragments, or a functionally equivalent subfragment thereof, or a complement thereof, operably linked to suitable regulatory sequences. Transformed host cells or plants comprising such chimeric genes are of interest. Indeed, these nucleic acid fragments can be used in any of the above-identified methods such as altering the level of fatty acids in a host cell or plant, producing plant fatty acid modifying enzymes associated with modification of a delta-12 position of a fatty acid, etc.

BRIEF DESCRIPTION OF THE FIGURES AND SEQUENCE DESCRIPTIONS

The invention can be more fully understood from the following detailed description and the Figure and Sequence Descriptions which form a part of this application.

The sequence descriptions summarize the Sequences Listing attached hereto. The Sequence Listing contains one letter codes for nucleotide sequence characters and the three letter codes for amino acids as defined in the IUPAC-IUB standards described in *Nucleic Acids Research* 13:3021–3030 (1985) and in the *Biochemical Journal* 219 (No. 2):345–373 (1984), and the symbols and format used for all nucleotide and amino acid sequence data further comply with the rules governing nucleotide and/or amino acid sequence disclosures in patent applications as set forth in 37 C.F.R. §1.821–1.825 and WIPO Standard St.25.

FIG. 1 shows the structures of α-linolenic acid, calendic acid, and α-eleostearic acid.

FIGS. 2A–2D show a comparison of the amino acid sequences of the instant fatty acid modifying enzymes associated with conjugated double bond formation comprising a modification of the delta-9 position of fatty acids from seeds of *Calendula officinalis* (CalFad2-1 and CalFad2-2), *Dimorphotheca sinuata* (DMFad2-2), and a delta-12 modifying enzyme from *Dimorphotheca sinuata* (DMFad2-1). The two Calendula genes, that encode enzymes that form $18:3\Delta^{8,10,12}$ conjugated double bonds, are compared to the genes from *Impatiens balsamina* (ImpFad2 H8), *Momordica charantia* (MomFad2), and *Chrysobalanus icaco* (ChrFad2) that encode enzymes forming $18:3\Delta^{9,11,13}$ conjugated double bonds, a castor bean fatty acid hydroxylase (Hydroxylase), and a soybean omega-6 oleate desaturase (Soy omega-6). The two *Dimorphotheca sinuata* amino acid sequences (DMFad2-1 and DMFad2-2) are compared to delta-12 fatty acid desaturases from sunflower (*Helianthus annuus*), and borage (*Borago officinalis*), respectively. The conserved histidine motifs found in desaturases and hydroxylases are boxed. The position of the glycine substitution for alanine, mentioned in Example 5, is highlighted with an asterisk (*).

FIGS. 3A, B, and C shows the fatty acid profile of transgenic yeast expressing the Calendula fatty acid-modifying enzyme associated with conjugated double bond formation comprising a modification of the delta-9 position of fatty acids. Shown are gas chromatograms of fatty acid methyl esters prepared from (A) wild-type yeast, (B) transgenic yeast expressing the Calendula CalFad2-1 gene, and (C) from wild-type Calendula seeds.

Figure 4:
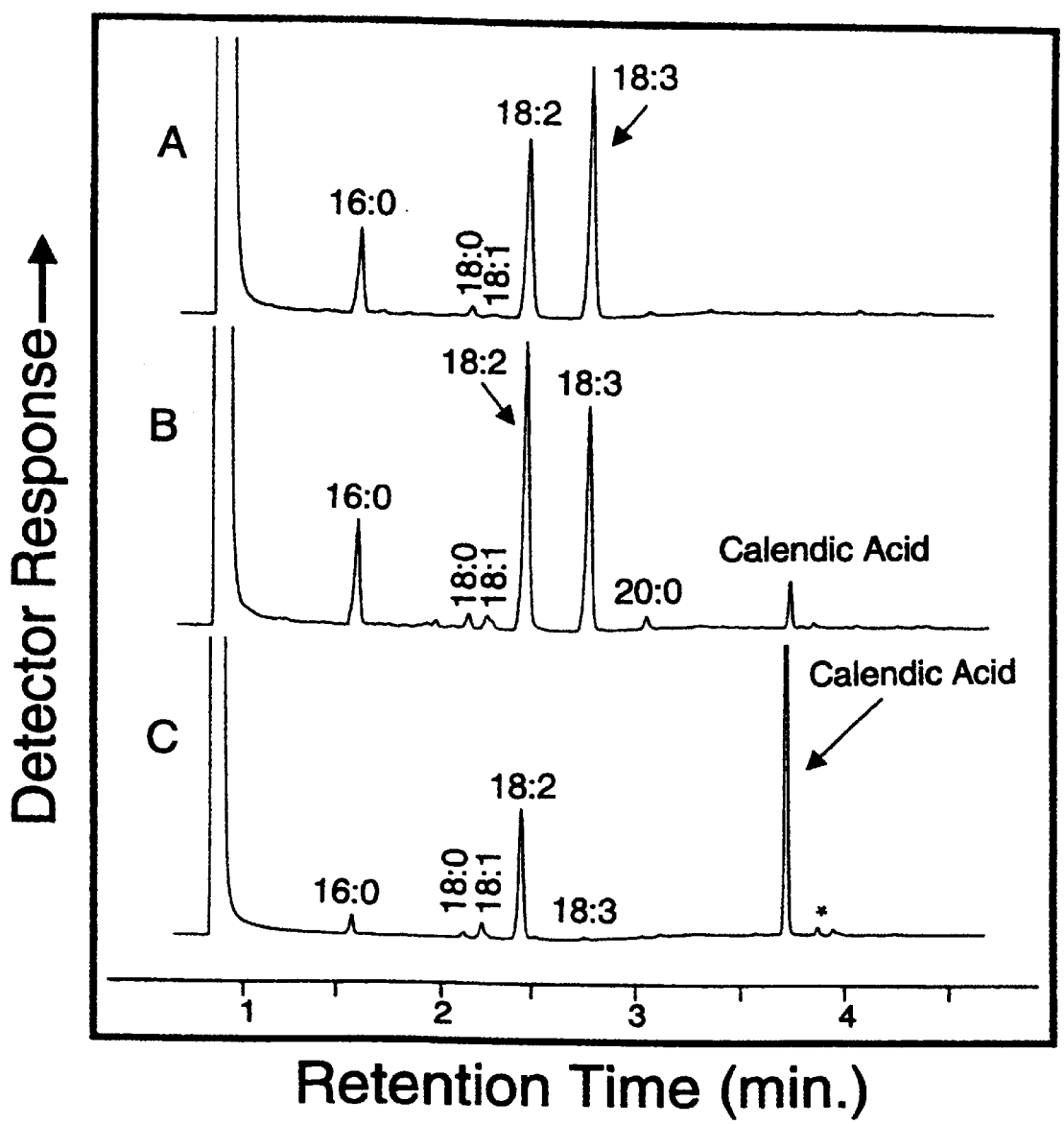

FIGS. 4A, B, and C shows the fatty acid profile of transgenic tobacco callus expressing the Calendula fatty acid-modifying enzyme associated with conjugated double bond formation comprising a modification of the delta-9 position of fatty acids. Shown are gas chromatograms of fatty acid methyl esters prepared from (A) wild-type tobacco callus, (B) transgenic tobacco callus expressing the Calendula CalFad2-1 gene, and (C) fatty acids isolated from wild-type Calendula seeds.

FIGS. 5A, B, and C shows a gas chromatographic analysis of fatty acid methyl esters prepared from somatic soybean embryos expressing CalFad2-2. Shown are gas chromatograms of fatty acid methyl esters from (A) untransformed soybean embryos, (B) transgenic embryos expressing CalFad2-2, and (C) a standard fatty acid methyl ester mix prepared from seeds of *Punica granatum, Momordica charantia,* and *Calendula officinalis,* all of which accumulate fatty acids with conjugated double bonds. Punica seeds accumulate punicic acid ($18:3\Delta^{9cis,11trans,13cis}$), Momordica seeds accumulate α-eleostearic acid ($18:3\Delta^{9cis,11trans,13trans}$), and Calendula seeds accumulate calendic acid ($18:3\Delta^{8trans,10trans,12cis}$). As shown, the novel fatty acid methyl ester peak in soybean embryos expressing CalFad2-2 has the same retention time (3.26 min) as methyl calendic acid from *Calendula officinalis* seeds. (The peak in B labeled with an asterisk is tentatively identified as methyl $18:3\Delta^{8trans, 10trans, 12trans}$).

FIGS. 6A and B shows a mass spectral analysis of 4-methyl-1,2,4-triazoline-3,5-dione (MTAD) derivatives of methyl calendic acid from (A) *Calendula officinalis* seeds and from (B) transgenic somatic soybean embryos expressing CalFad2-2. The MTAD reagent preferentially reacts with the conjugated $\Delta^{8trans}$ and $\Delta^{10trans}$ double bonds of methyl calendic acid to yield the derivative shown in A. As indicated, the mass spectrum of the MTAD derivative prepared from transgenic soybean embryos expressing CalFad2-2 (B) is identical to that of the MTAD derivative of methyl calendic acid from Calendula seeds (A). A similar mass spectrum was also obtained from MTAD derivatives prepared from transgenic soybean embryos expressing CalFad2-1 (data not shown).

Figure 7:
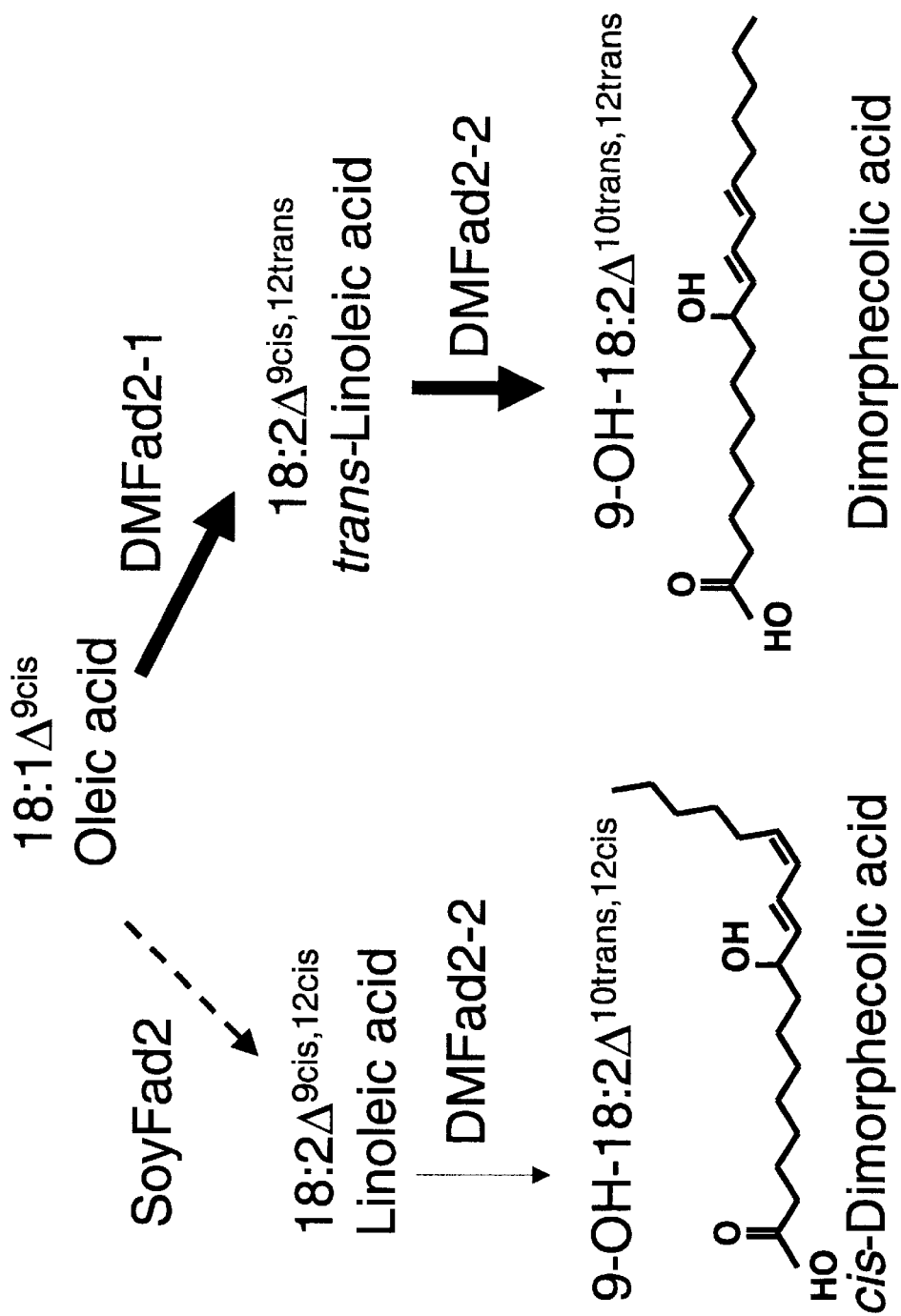

FIG. 7 shows the biosynthesis of dimorphecolic acid in transgenic somatic soybean embryos. The biosynthetic pathway is based on results from the transgenic expression of DMFad2-1 and DMFad2-2 as described in Example 11.

Figure 8:
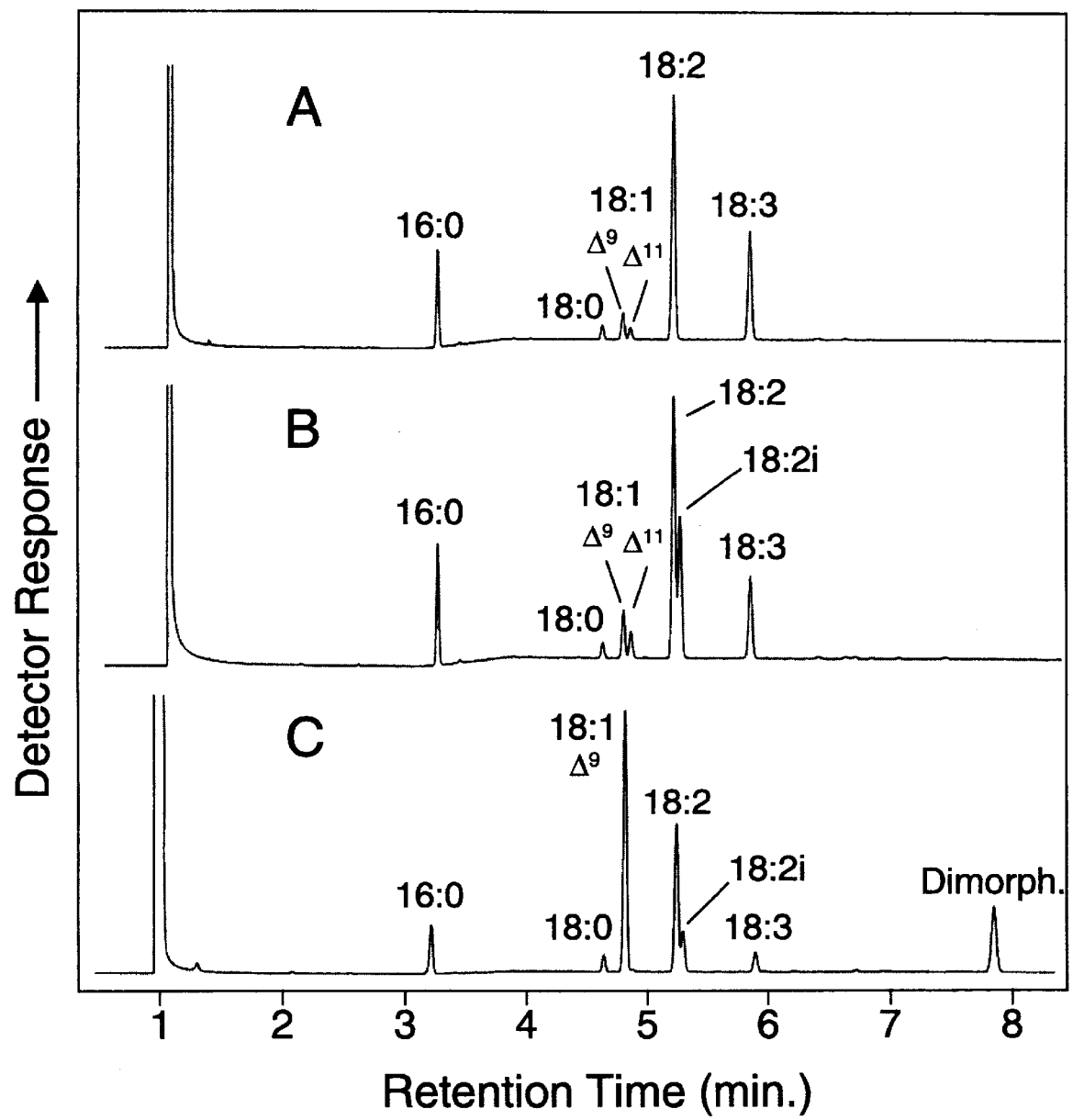

FIGS. 8A, B, and C shows the gas chromatographic analyses of fatty acid methyl esters from (A) untransformed somatic soybean embryos, (B) somatic soybean embryos expressing DMFad2-1, and (C) developing *Dimorphotheca sinuata* seeds. The peak labeled 18:2i corresponds to the trans-$\Delta^{12}$ isomer of linoleic acid ($18:2\Delta^{9cis,12trans}$). The peak labeled Dimorph. in panel C corresponds to dimorphecolic acid.

FIGS. 9A, B, and C shows the selected ion chromatograms from GC-MS analyses of fatty acid methyl ester derivatives from (A) developing *Dimorphotheca sinuata* seeds, (B) transgenic somatic soybean embryos expressing DMFad2-2 and (C) transgenic somatic soybean embryos co-expressing DMFad2-1 and DMFad2-2. Chromatograms were obtained by scanning for the 225 m/z ion, which is the primary ion of the trimethyl silyl derivative of methyl dimorphecolic acid. Extracts from somatic soybean embryos shown in panel B lacked detectable amounts of the 18:2$\Delta^{9cis, 12trans}$, the preferred substrate for dimorphecolic acid synthesis which is formed by the activity of DMFad2-1. In contrast, 18:2$\Delta^{9cis, 12trans}$ composed >10% of the total fatty acids in extracts from somatic soybean embryos shown in panel C. cis-Dimorph.=the tentatively identified cis-$\Delta^{12}$ isomer of dimorphecolic acid (9-OH -18:2$\Delta^{9cis, 12cis}$). Dimorph.=dimorphecolic acid (9-OH-18:2$\Delta^{9cis, 12trans}$).

FIGS. 10A and B shows the mass spectra of the trimethyl silyl derivative of methyl dimorphecolic acid from developing *Dimorphotheca sinuata* seeds (A) and transgenic somatic soybean embryos co-expressing DMFad2-1 and DMFad2-2 (B).

SEQ ID NO:1 is the nucleotide sequence comprising the cDNA insert in clone ecs1c.pk009.n14 (CalFad2-1) encoding an fatty acid modifying enzymes associated with conjugated double bond formation comprising a modification of the delta-9 position of fatty acids from seeds of *Calendula officinalis*.

SEQ ID NO:2 is the deduced amino acid sequence of the nucleotide sequence comprising the cDNA insert in CalFad2-1.

SEQ ID NO:3 is the nucleotide sequence comprising the cDNA insert in clone ecs1c.pk008.a24 (CalFad2-2) encoding fatty acid modifying enzymes associated with conjugated double bond formation comprising a modification of the delta-9 position of fatty acids from seeds of *Calendula officinalis*.

SEQ ID NO:4 is the deduced amino acid sequence of the nucleotide sequence comprising the cDNA insert in CalFad2-2.

SEQ ID NO:5 is the amino acid sequence encoding the soybean (*Glycine max*) fatty acid desaturase enzyme depicted in FIG. 2.

SEQ ID NO:6 is the amino acid sequence encoding the castor bean (*Ricinus communis*) fatty acid hydroxylase enzyme depicted in FIG. 2.

SEQ ID NO:7 is the deduced amino acid sequence of the nucleotide sequence comprising the cDNA insert in clone ImpH8Fad2 encoding an fatty acid modifying enzymes associated with conjugated double bond formation from seeds of *Impatiens balsamina*.

SEQ ID NO:8 is the deduced amino acid sequence of the nucleotide sequence comprising the cDNA insert in clone MomFad2 encoding fatty acid modifying enzymes associated with conjugated double bond formation from seeds of *Momordica charantia*.

SEQ ID NO:9 is the deduced amino acid sequence of the nucleotide sequence comprising the cDNA insert in the clone from ChrFad2 encoding a fatty acid modifying enzymes associated with conjugated double bond formation from seeds of *Chrysobalanus icaco*.

SEQ ID NO:10 is the nucleotide sequence comprising the cDNA insert in clone dms2c.pk006.d7 (DMFad2-1) encoding an fatty acid modifying enzymes associated with modification of the delta-12 position of fatty acids from seeds of *Dimorphotheca sinuata*.

SEQ ID NO:11 is the deduced amino acid sequence of the nucleotide sequence comprising the cDNA insert in DMFad2-1.

SEQ ID NO:12 is the nucleotide sequence comprising the cDNA insert in clone dms2c.pk001.113 (DMFad2-2) encoding fatty acid modifying enzymes associated with conjugated double bond formation comprising a modification of the delta-9 position of fatty acids from seeds of *Dimorphotheca sinuata*.

SEQ ID NO:13 is the deduced amino acid sequence of the nucleotide sequence comprising the cDNA insert in DMFad2-2.

SEQ ID NO:14 is the amino acid sequence encoding the sunflower (*Helianthus annuus*) fatty acid desaturase enzyme depicted in FIG. 2.

SEQ ID NO:15 is the amino acid sequence encoding the borage (*Borago officinalis*) fatty acid hydroxylase enzyme depicted in FIG. 2.

SEQ ID NO:16 is the BamHI-containing 5'-end "sense" primer used to amplify the *Calendula officinalis* coding region for cloning into the vector pBI121 for expression in tobacco.

SEQ ID NO:17 is the SstI-containing 3'-end "anti-sense" primer used to amplify the *Calendula officinalis* coding region for cloning into the vector pBI121 for expression in tobacco.

SEQ ID NO:18 is the NotI-containing 5'-end "sense" primer used to amplify the *Calendula officinalis* CalFad2-1 coding region for cloning into the vector pKS67 for expression in soybean.

SEQ ID NO:19 is the NotI-containing 3'-end "anti-sense" primer used to amplify the *Calendula officinalis* CalFad2-1 coding region for cloning into the vector pKS67 for expression in soybean.

SEQ ID NO:20 is the NotI-containing 5'-end "sense" primer used to amplify the *Calendula officinalis* CalFad2-2 coding region for cloning into the vector pKS67 for expression in soybean.

SEQ ID NO:21 is the NotI-containing 3'-end "anti-sense" primer used to amplify the *Calendula officinalis* CalFad2-2 coding region for cloning into the vector pKS67 for expression in soybean. SEQ ID NO:22 is the NotI-containing 5'-end "sense" primer used to amplify the *Dimorphotheca sinuata* DMFad2-1 coding region for cloning into the vector pKS67 for expression in soybean.

SEQ ID NO:23 is the NotI-containing 3'-end "anti-sense" primer used to amplify the *Dimorphotheca sinuata* DMFad2-1 coding region for cloning into the vector pKS67 for expression in soybean.

SEQ ID NO:24 is the NotI-containing 5'-end "sense" primer used to amplify the *Dimorphotheca sinuata* DMFad2-2 coding region for cloning into the vector pKS67 for expression in soybean.

SEQ ID NO:25 is the NotI-containing 3'-end "anti-sense" primer used to amplify the *Dimorphotheca sinuata* DMFad2-2 coding region for cloning into the vector pKS67 for expression in soybean.

DETAILED DESCRIPTION OF THE INVENTION

In the context of this disclosure, a number of terms shall be utilized.

As used herein, an "isolated nucleic acid fragment" is a polymer of RNA or DNA that is single- or double-stranded, optionally containing synthetic, non-natural or altered nucleotide bases. An isolated nucleic acid fragment in the form of a polymer of DNA may be comprised of one or more segments of cDNA, genomic DNA or synthetic DNA.

The terms "subfragment that is functionally equivalent" and "functionally equivalent subfragment" are used interchangeably herein. These terms refer to a portion or subsequence of an isolated nucleic acid fragment in which the ability to alter gene expression or produce a certain phenotype is retained whether or not the fragment or subfragment encodes an active enzyme. For example, the fragment or subfragment can be used in the design of chimeric genes to produce the desired phenotype in a transformed plant. Chimeric genes can be designed for use in co-suppression or antisense by linking a nucleic acid fragment or subfragment thereof, whether or not it encodes an active enzyme, in the appropriate orientation relative to a plant promoter sequence.

The terms "substantially similar" and "corresponding substantially" as used herein refer to nucleic acid fragments wherein changes in one or more nucleotide bases does not affect the ability of the nucleic acid fragment to mediate gene expression or produce a certain phenotype. These terms also refer to modifications of the nucleic acid fragments of the instant invention such as deletion or insertion of one or more nucleotides that do not substantially alter the functional properties of the resulting nucleic acid fragment relative to the initial, unmodified fragment. It is therefore understood, as those skilled in the art will appreciate, that the invention encompasses more than the specific exemplary sequences.

Moreover, the skilled artisan recognizes that substantially similar nucleic acid sequences encompassed by this invention are also defined by their ability to hybridize, under moderately stringent conditions (for example, 0.5×SSC, 0.1% SDS, 60° C.) with the sequences exemplified herein, or to any portion of the nucleotide sequences reported herein and which are functionally equivalent to the promoter of the invention. Preferred substantially similar nucleic acid sequences encompassed by this invention are those sequences that are 40% identical to the nucleic acid fragments reported herein or which are 40% identical to any portion of the nucleotide sequences reported herein. More preferred are nucleic acid fragments which are 50% identical to the nucleic acid sequences reported herein, or which are 50% identical to any portion of the nucleotide sequences reported herein. Most preferred are nucleic acid fragments which are 60% identical to the nucleic acid sequences reported herein, or which are 60% identical to any portion of the nucleotide sequences reported herein. Sequence alignments and percent similarity calculations may be determined using the Megalign program of the LASARGENE bioinformatics computing suite (DNASTAR Inc., Madison, Wis.). Multiple alignment of the sequences are performed using the Clustal method of alignment (Higgins and Sharp (1989) *CABIOS.* 5:151–153) with the default parameters (GAP PENALTY=10, GAP LENGTH PENALTY=10). Default parameters for pairwise alignments and calculation of percent identity of protein sequences using the Clustal method are KTUPLE=1, GAP PENALTY=3, WINDOW=5 and DIAGONALS SAVED=5. For nucleic acids these parameters are KTUPLE=2, GAP PENALTY=5, WINDOW=4 and DIAGONALS SAVED=4.

A "substantial portion" of an amino acid or nucleotide sequence comprises enough of the amino acid sequence of a polypeptide or the nucleotide sequence of a gene to afford putative identification of that polypeptide or gene, either by manual evaluation of the sequence by one skilled in the art, or by computer-automated sequence comparison and identification using algorithms such as BLAST (Altschul, S. F., et al., (1993) *J. Mol. Biol.* 215:403–410) and Gapped Blast (Altschul, S. F. et al., (1997) *Nucleic Acids Res.* 25:3389–3402).

"Gene" refers to a nucleic acid fragment that expresses a specific protein, including regulatory sequences preceding (5' non-coding sequences) and following (3' non-coding sequences) the coding sequence. "Native gene" refers to a gene as found in nature with its own regulatory sequences. "Chimeric gene" refers any gene that is not a native gene, comprising regulatory and coding sequences that are not found together in nature. Accordingly, a chimeric gene may comprise regulatory sequences and coding sequences that are derived from different sources, or regulatory sequences and coding sequences derived from the same source, but arranged in a manner different than that found in nature. "Endogenous gene" refers to a native gene in its natural location in the genome of an organism. A "foreign" gene refers to a gene not normally found in the host organism, but that is introduced into the host organism by gene transfer. Foreign genes can comprise native genes inserted into a non-native organism, or chimeric genes. A "transgene" is a gene that has been introduced into the genome by a transformation procedure.

"Coding sequence" refers to a DNA sequence that codes for a specific amino acid sequence. "Regulatory sequences" refer to nucleotide sequences located upstream (5' non-coding sequences), within, or downstream (3' non-coding sequences) of a coding sequence, and which influence the transcription, RNA processing or stability, or translation of the associated coding sequence. Regulatory sequences may include, but are not limited to, promoters, translation leader sequences, introns, and polyadenylation recognition sequences.

"Promoter" refers to a DNA sequence capable of controlling the expression of a coding sequence or functional RNA. The promoter sequence consists of proximal and more distal upstream elements, with the latter elements often referred to as enhancers. Accordingly, an "enhancer" is a DNA sequence which can stimulate promoter activity and may be an innate element of the promoter or a heterologous element inserted to enhance the level or tissue-specificity of a promoter. Promoters may be derived in their entirety from a native gene, or be composed of different elements derived from different promoters found in nature, or even comprise synthetic DNA segments. It is understood by those skilled in the art that different promoters may direct the expression of a gene in different tissues or cell types, or at different stages of development, or in response to different environmental conditions. Promoters which cause a gene to be expressed in most cell types at most times are commonly referred to as "constitutive promoters". New promoters of various types useful in plant cells are constantly being discovered; numerous examples may be found in the compilation by Okamuro and Goldberg, (1989) *Biochemistry of Plants* 15:1–82. It is further recognized that since in most cases the exact boundaries of regulatory sequences have not been completely defined, DNA fragments of some variation may have identical promoter activity.

An "intron" is an intervening sequence in a gene that does not encode a portion of the protein sequence. Thus, such sequences are transcribed into RNA but are then excised and are not translated. The term is also used for the excised RNA sequences. An "exon" is a portion of the sequence of a gene that is transcribed and is found in the mature messenger RNA derived from the gene, but is not necessarily a part of the sequence that encodes the final gene product.

The "translation leader sequence" refers to a DNA sequence located between the promoter sequence of a gene and the coding sequence. The translation leader sequence is present in the fully processed mRNA upstream of the translation start sequence. The translation leader sequence may affect processing of the primary transcript to mRNA, mRNA stability or translation efficiency. Examples of translation leader sequences have been described (Turner, R. and Foster, G. D. (1995) Molecular Biotechnology 3:225).

The "3' non-coding sequences" refer to DNA sequences located downstream of a coding sequence and include polyadenylation recognition sequences and other sequences encoding regulatory signals capable of affecting mRNA processing or gene expression. The polyadenylation signal is usually characterized by affecting the addition of polyadenylic acid tracts to the 3' end of the mRNA precursor. The use of different 3' non-coding sequences is exemplified by Ingelbrecht et al., (1989) Plant Cell 1:671–680.

"RNA transcript" refers to the product resulting from RNA polymerase-catalyzed transcription of a DNA sequence. When the RNA transcript is a perfect complementary copy of the DNA sequence, it is referred to as the primary transcript or it may be a RNA sequence derived from posttranscriptional processing of the primary transcript and is referred to as the mature RNA. "Messenger RNA (mRNA)" refers to the RNA that is without introns and that can be translated into protein by the cell. "cDNA" refers to a DNA that is complementary to and synthesized from a mRNA template using the enzyme reverse transcriptase. The cDNA can be single-stranded or converted into the double-stranded form using the klenow fragment of DNA polymerase I. "Sense" RNA refers to RNA transcript: that includes the mRNA and so can be translated into protein within a cell or in vitro. "Antisense RNA" refers to a RNA transcript that is complementary to all or part of a target primary transcript or mRNA and that blocks the expression of a target gene (U.S. Pat. No. 5,107,065). The complementarity of an antisense RNA may be with any part of the specific gene transcript, i.e., at the 5' non-coding sequence, 3' non-coding sequence, introns, or the coding sequence. "Functional RNA" refers to antisense RNA, ribozyme RNA, or other RNA that may not be translated but has an effect on cellular processes. The terms "complement" and "reverse complement" are used interchangeably herein with respect to mRNA transcripts, and are meant to define the antisense RNA of the message.

The term "operably linked" refers to the association of nucleic acid sequences on a single nucleic acid fragment so that the function of one is affected by the other. For example, a promoter is operably linked with a coding sequence when it is capable of affecting the expression of that coding sequence (i.e., that the coding sequence is under the transcriptional control of the promoter). Coding sequences can be operably linked to regulatory sequences in sense or antisense orientation.

The term "expression", as used herein, refers to the production of a functional end-product. Expression or overexpression of a gene involves transcription of the gene and translation of the mRNA into a precursor or mature protein. "Antisense inhibition" refers to the production of antisense RNA transcripts capable of suppressing the expression of the target protein. "Overexpression" refers to the production of a gene product in transgenic organisms that exceeds levels of production in normal or non-transformed organisms. "Co-suppression" refers to the production of sense RNA transcripts capable of suppressing the expression of identical or substantially similar foreign or endogenous genes (U.S. Pat. No. 5,231,020).

"Altered expression" refers to the production of gene product(s) in transgenic organisms in amounts or proportions that differ significantly from that activity in comparable tissue (organ and of developmental type) from wild-type organisms.

"Mature" protein refers to a post-translationally processed polypeptide; i.e., one from which any pre- or propeptides present in the primary translation product have been removed. "Precursor" protein refers to the primary product of translation of mRNA; i.e., with pre- and propeptides still present. Pre- and propeptides may be but are not limited to intracellular localization signals.

A "chloroplast transit peptide" is an amino acid sequence which is translated in conjunction with a protein and directs the protein to the chloroplast or other plastid types present in the cell in which the protein is made. "Chloroplast transit sequence" refers to a nucleotide sequence that encodes a chloroplast transit peptide. A "signal peptide" is an amino acid sequence which is translated in conjunction with a protein and directs the protein to the secretory system (Chrispeels, J. J., (1991) Ann. Rev. Plant Phys. Plant Mol. Biol. 42:21–53). If the protein is to be directed to a vacuole, a vacuolar targeting signal (supra) can further be added, or if to the endoplasmic reticulum, an endoplasmic reticulum retention signal (supra) may be added. If the protein is to be directed to the nucleus, any signal peptide present should be removed and instead a nuclear localization signal included (Raikhel (1992) Plant Phys. 100:1627–1632).

"Transformation" refers to the transfer of a nucleic acid fragment into the genome of a host organism, resulting in genetically stable inheritance. Host organisms containing the transformed nucleic acid fragments are referred to as "transgenic" organisms. The preferred method of cell transformation of rice, corn and other monocots is the use of particle-accelerated or "gene gun" transformation technology (Klein et al., (1987) Nature (London) 327:70–73; U.S. Pat. No. 4,945,050), or an Agrobacterium-mediated method using an appropriate Ti plasmid containing the transgene (Ishida Y. et al., 1996, Nature Biotech. 14:745–750).

Standard recombinant DNA and molecular cloning techniques used herein are well known in the art and are described more fully in Sambrook, J., Fritsch, E. F. and Maniatis, T. Molecular Cloning: A Laboratory Manual; Cold Spring Harbor Laboratory Press: Cold Spring Harbor, 1989 (hereinafter "Sambrook").

"PCR" or "Polymerase Chain Reaction" is a technique for the synthesis of large quantities of specific DNA segments, consists of a series of repetitive cycles (Perkin Elmer, Cetus Instruments, Norwalk, Conn.). Typically, the double stranded DNA is heat denatured, the two primers complementary to the 3' boundaries of the target segment are annealed at low temperature and then extended at an intermediate temperature. One set of these three consecutive steps is referred to as a cycle.

An "expression construct" as used herein comprises any of the isolated nucleic acid fragments of the invention used either alone or in combination with each other as discussed herein and further may be used in conjunction with a vector or a subfragment thereof. If a vector is used then the choice of vector is dependent upon the method that will be used to transform host plants as is well known to those skilled in the art. For example, a plasmid vector can be used. The skilled artisan is well aware of the genetic elements that must be present on the vector in order to successfully transform, select and propagate host cells or plants comprising any of the isolated nucleic acid fragments of the invention. The skilled, artisan will also recognize that different independent transformation events will result in different levels and patterns of expression (Jones et al., (1985) *EMBO J.* 4:2411–2418; De Almeida et al., (1989) *Mol. Gen. Genetics* 218:78–86), and thus that multiple events must be screened in order to obtain lines displaying the desired expression level and pattern. Such screening may be accomplished by Southern analysis of DNA, Northern analysis of mRNA expression, Western analysis of protein expression, or phenotypic analysis. The terms "expression construct" and "recombinant expression construct" are used interchangeably herein.

The term "$\omega^6$-oleic acid desaturase" refers to a cytosolic enzyme that catalyzes the insertion of a double bond into oleic acid between the twelfth and thirteenth carbon atoms relative to the carboxyl end of the acyl chain. Double bonds are referred to as "cis" or "trans" because they are chiral units that can assume the following non-equivalent structures:

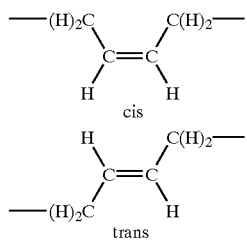

The linoleic acid substrate for this enzyme may be bound to a glycerolipid such as phosphatidylcholine. In fatty acid chains the omega-carbons are counted from the methyl-end, while the delta-carbons are counted from the carboxyl-end. Thus, the term "delta-9 position", as used herein means the 9th carbon atom counting from the carboxyl-end of the fatty acid chain. Modifications involving the delta-9 position include, but are not limited to, at least one modification selected from the group consisting of double bond formation, conjugated double bond formation, hydroxylation, epoxidation, hydroxy-conjugation, and the like. For example, a modification can involve just one alteration such as conjugated double bond formation or a modification can involve more than one alteration such as conjugated double bond formation and hydroxylation (hydroxy-conjugation). The term "modification of the delta-9 ($\Delta^9$) position" and "a modified delta-9 ($\Delta^9$) position" are used interchangeably. Also, the term "modification of the delta-12 position", as used herein means a double bond formation involving the $12^{th}$ carbon counting from the carboxyl-end of the fatty acid chain. This modification as described in the present invention involves the formation of a trans-$\Delta^{12}$ double bond resulting in the formation of trans-linoleic acid ($18:2\Delta^{9cis, 12trans}$).

In the production of calendic acid, the delta-9 double bond of linoleic acid ($18:2\Delta^{9,12}$) is converted by the activity of CalFad2-1 or CalFad2-2 to delta-8 and delta-10 double bonds. The resulting calendic acid, a linolenic acid derivative, contains delta-8, delta-10, and delta-12 double bonds in conjugation ($18:3\Delta^{8,10,12}$). CalFad2-1 and CalFad2-2 are thus distinct from all previously reported Fad2-related polypeptides by their ability to modify the delta-9 rather than the delta-12 position of a fatty acid. The enzymes from *Impatiens balsamina*, *Momordica charantia*, and *Chrysobalanus icaco*, shown in FIG. 2, all convert the delta-12 double bond of linoleic acid to delta-11 and delta-13 conjugated double bonds, to form eleostearic acid ($18:3\Delta^{9,11,13}$).

In the production of dimorphecolic acid (9-hydroxy-$18:2\Delta^{10trans, 12trans}$, see FIG. 7 for the structure) oleic acid is first converted to trans-linoleic acid ($18:2\Delta^{9cis, 12trans}$) by the enzyme designated DMFad2-1. This enzyme (DMFad2-1) is a *Dimorphotheca sinuata* fatty acid modifying enzyme associated with the formation of a trans delta-12 double bond wherein said enzyme modifies a delta-12 position of fatty acids by inserting a double bond having a trans configuation between carbon atoms 12 and 13. The resulting product of this enzymatic reaction is trans-linoleic acid. This product then becomes the substrate for the next enzymatic reaction in this pathway. Specifically, trans-linoleic acid is converted by the enzyme DMFad2-2 to dimorphecolic acid, which is a conjugated double-bond containing fatty acid. The enzyme DMFad2-2 is a $\Delta$-9 hydroxy-conjugase from *Dimorphotheca sinuata*. The enzyme introduces a hydroxyl group at position 9 and converts $18:2\Delta^{9cis, 12trans}$ (trans-linoleic acid) to the conjugated double bond containing dimorphecolic acid (9-hydroxy-$18:2\Delta^{10trans, 12trans}$). A related product, cis-dimorphecolic acid (9-hydroxy -$18:2\Delta^{10trans, 12cis}$, see FIG. 7 for the structure) is produced by DMFad2-2 from endogenous soybean linoleic acid ($18:2\Delta^{9trans, 12cis}$). It is believed that the trans- form of linoleic acid is the preferred substrate for DMFad2-2.

The enzymes of the present invention, with the exception of DMFad2-1, comprise activities involving modification of fatty acids at the delta-9 position resulting in conjugated double bond formation. The term "conjugated double bond" is defined as two double bonds in the relative positions indicated by the formula —CH=CH—CH=CH— (Grant & Hackh's Chemical Dictionary, Fifth Ed., R. Grant and C. Grant eds., McGraw-Hill, New York). The $\pi$-orbital electrons are shared between conjugated double bonds, but remain relatively independent in unconjugated double bonds. This explains the greater reactivity of conjugated double bonds to oxidation. The modifying enzymes, associated with conjugated double bond formation described herein, are related to, and share sequence homology to, the fatty acid desaturases (Fads), especially the Fad2 class. Fads introduce double bonds in fatty acid chains that result in the formation of the mono and polyunsaturated oils, such as oleate,: linoleate, and linolenate, but do not produce conjugated double bonds. The terms "Fad2 related" and "Fad2-like" reflect the conservation and differences in nucleic acid sequence homology between the genes encoding Fad2 enzymes versus the genes of the present invention.

This invention concerns an isolated nucleic acid fragment encoding a plant fatty acid modifying enzyme associated with conjugated double bond formation comprising the delta-9 position of fatty acids, or in the case of DMFad2-1, modification of a delta-12 position, wherein said fragment or a functionally equivalent subfragment thereof (a) hybridizes to any of the nucleotide sequences set forth in SEQ ID NOs:1, 3, or 12 under conditions of moderate stringency or (b) is at least 40% identical to a polypeptide encoded by any of the nucleotide sequences set forth in SEQ ID NOs:1, 3, or 12 or a functionally equivalent subfragment thereof as determined by a comparison method designed to detect homologous sequences.

This invention also concerns an isolated nucleic acid fragment encoding a plant fatty acid modifying enzyme wherein said enzyme modifies a delta-9 position of fatty acids and further wherein said fragment or a functionally equivalent subfragment thereof (a) hybridizes to any of the nucleotide sequences set forth in SEQ ID NOs:1, 3, or 12 under conditions of moderate stringency or (b) is at least 40% identical to a polypeptide encoded: by any of the nucleotide sequences set forth in SEQ ID NOs:1, 3, or 12 or a functionally equivalent subfragment thereof as determined by a comparison method designed to detect homologous sequences.

Such enzymes are normally expressed in developing seeds of *Calendula officinalis* or *Dimorphotheca sinuata* that are similar in sequence to plant, membrane-bound fatty acid desaturases. However, these fatty acid modifying enzymes differ from membrane-bound fatty acid desaturases in their functionality. Specifically, these enzymes are associated with the formation of fatty acids having conjugated double bonds and, more particularly, with the formation of conjugated linolenic acids. Examples of fatty acids having conjugated double bonds include, but are not limited to, eleostearic acid and/or parinaric acid. Naturally occurring plant oils containing eleostearic acid include tung oil from *Aleurites fordii* or *montana,* which contains up to 69% α-eleostearic acid in the oil extracted from the seeds, or oils from valarian species (*Centranthus microsiphon*). There can also be mentioned jacaric acid (from the jacaranda tree, *Jacaranda mimosifolia* and *Jacaranda chelonia,* $18:3\Delta^{8cis, 10trans, 12cis}$), calendic acid (from marigold or African daisy, *Calendula officinalis,* and *Osteospermum spinescens* and *Osteospermum hyoseroides,* $18:3\Delta^{8trans, 10trans, 12cis}$), catalpic acid (from the trumpet creeper, *Catalpa ovata,* or *speciosa,* or *bigninioides,* $18:3\Delta^{9trans, 11trans, 13cis}$), and punicic acid (from bitter melon and pomegranate, or Tricosanthes species, Cucurbita, and *Punica granatum, Tricosanthes cucumeroides,* $18:3\Delta^{9cis, 11trans, 13cis}$). These and other examples of fatty acids having conjugated double bonds may be found in "The Lipid Handbook" (Second Edition, Gunstone, F. D., et al., eds., Chapman and Hall, London, 1994), Crombie and Holloway (*J. Chem. Soc.* Perkins Trans. 1985:2425–2434), and Liu, et al. (*Plant. Physiol.* [1997] 113:1343–1349). These conjugated fatty acids are also referred to as ClnAs (conjugated linolenic acids) because they are all 18:3 in composition. This is in contrast to CLAs (conjugated linoleic acids) which have an 18:2 configuration.

The nomenclature "18:3" denotes the number of carbons in the fatty acid chain (in this case "18" or stearic acid length), and the number of unsaturating double bonds (in this case "3" specifying this fatty acid as linolenic). Although 18:2 and 18:3 denote linoleic acid and linolenic acid, respectively, the positions of the double bonds are not specified (i.e. they may be unconjugated or conjugated, cis or trans). The term "calendic acid" as used herein refers to a mixture of cis-trans isomers of $\Delta^{8,10,12}$-octadecatrienoic acid ($18:3\Delta^{8,10,12}$). This mixture is primarily composed of the $\Delta^{8trans, 10trans, 12cis}$ isomer of octadecatrienoic acid (18:3) but may also contain various cis-trans isomers of this fatty acid. As those skilled in the will appreciate, the various isomers of calendic acid are separated easily by gas chromatography-mass spectrometry (GC-MS, see FIG. 3). More details on GC-MS analyses are found in Examples 3, 4, 6, 7, and 8. The term "dimorphecolic acid" as used herein refers to 9-hydroxy-$18:2\Delta^{10trans, 12trans}$ (see FIG. 7 for the structure). This unusual fatty acid and the intermediate that is its precursor (trans-linoleic acid, $18:2\Delta^{9cis, 12trans}$) can be analyzed by GC-MS analyses (see Example 11) and by $^1H$-$^{13}C$ NMR two-dimensional correlation NMR (see Example 12).

Examples of comparison methods which detect sequence homology include but are not limited to the BLAST computational method (Basic Local Alignment Search Tool; Altschul et al. (1993) *J. Mol. Biol.* 215:403–410) which includes BLASTN (nucleotide, both strands), BLASTX (nucleotide, six-frame translation), BLASTP (protein), TBLASTN (protein, from six-frame translation), TBLASTX (nucleotide, six-frame translation), Megalign program of the LASARGENE bioinformatics computing suite (DNASTAR Inc., Madison, Wis., used for calculating percent identity), and the Clustal method of multiple sequence alignment (Higgins and Sharp (1989) *CABIOS.* 5:151–153). The default parameters were used for all comparisons and for all methods. The BLAST suite at NCBI has a detailed discussion of their algorithms at their web site, the Megalign program uses a Clustal program that shares default parameters with Clustal, namely, for multiple sequence alignments of nucleic acids or polypeptides (GAP PENALTY=10, GAP LENGTH PENALTY=10), for pairwise alignments of nucleic acids (KTUPLE=2, GAP PENALTY=5, WINDOW=4, DIAGONALS SAVED=4), and for pairwise alignments of polypeptides (KTUPLE=1, GAP PENALTY= 3, WINDOW=5, DIAGONALS SAVED=5).

This invention also relates to the following:
a) an isolated nucleic acid fragment encoding a plant fatty acid modifying enzyme associated with conjugated double bond formation comprising the delta-9 position of fatty acids wherein said fragment encodes a protein comprising any one of the amino acid sequences set forth in SEQ ID NOs:2, 4, or 13, as well as
b) an isolated nucleic acid fragment encoding a plant fatty acid modifying enzyme wherein said enzyme modifies a delta-9 position of fatty acids and further wherein said fragment or a functionally equivalent subfragment thereof encodes a protein comprising any one of the amino acid sequences set forth in SEQ ID NOs:2, 4, or 13.

In another aspect, this invention concerns an isolated nucleic acid fragment encoding a plant fatty acid modifying enzyme associated with conjugated double bond formation comprising a the delta-9 position of fatty acids or an isolated nucleic acid fragment encoding a plant fatty acid modifying enzyme wherein said enzyme modifies the delta-9 position of the fatty wherein said fragments or a functionally equivalent subfragments thereof hybridize to any of the isolated nucleic acid fragments or functionally equivalent subfragments thereof encoding a plant fatty acid modifying enzyme associated with conjugated double bond formation comprising the delta-9 position of fatty acids or associated with modification of the delta-9 position wherein said fragments or subfragments encode a protein comprising any one of the amino acid sequences set forth in SEQ ID NOs:2, 4, or 13 and further wherein said fragments or subfragments (a) hybridize to these isolated nucleic acid fragments or functionally equivalent subfragments under conditions of moderate stringency or (b) is at least 40% identical to a polypeptide encoded by any of the foregoing isolated nucleic acid fragments or a functionally equivalent subfragments thereof as determined by a comparison method designed to detect homologous sequences. Examples of suitable comparison methods which detect homologous sequences are discussed above.

Also of interest is a chimeric gene comprising any of the instant isolated nucleic acid fragments, or functionally equivalent subfragments thereof, or a complement thereof operably linked to suitable regulatory sequences wherein expression of the chimeric gene results in production of altered levels of the desired enzyme in a transformed host cell or plant.

The invention also relates to methods of using such isolated nucleic acid fragments, or functionally equivalent subfragments thereof, or the complement thereof, to alter the level of fatty acids comprising a modification of the delta-9 position of fatty acids in a host cell or plant which comprises:

(a) transforming a host cell or plant with any of the instant chimeric genes;

(b) growing the transformed host cell or plant under conditions suitable for the expression of the chimeric gene; and (c) selecting those transformed host cells or plants having altered levels of fatty acids comprising a modification at the delta-9 position.

In still another aspect, this invention concerns a method for producing seed oil containing fatty acids comprising a modification at the delta-9 position in the seeds of plants which comprises:

(a) transforming a plant cell with any of the instant chimeric genes;

(b) growing a fertile mature plant from the transformed plant cell of step (a);

(c) screening progeny seeds from the fertile plants of step (b) for altered levels of fatty acids comprising a modification at the delta-9 position; and (d) processing the progeny seed of step (c) to obtain seed oil containing altered levels plant fatty acids comprising a modification at the delta-9 position.

In still a further aspect, this invention concerns a method for producing plant fatty acid modifying enzymes associated with modification of the delta-9 position of fatty acids which comprises:

(a) transforming a microbial host cell with any of the instant chimeric genes;

(b) growing the transformed host cell under conditions suitable for the expression of the chimeric gene; and (c) selecting those transformed host cells containing altered levels of protein encoded by the chimeric gene.

The isolated nucleic acid fragments encoding fatty acid modifying enzymes associated with conjugated double bond formation comprising the delta-9 position of fatty acids in seeds of *Calendula officinalis* is provided in SEQ ID NO:1 and 3, and the corresponding deduced amino acid sequences are provided in SEQ ID NO:2 and 4, and in the seeds of *Dimorphotheca sinuata* is provided in SEQ ID NO:12, and the corresponding deduced amino acid sequences are provided in SEQ ID NO:13. Fatty acid modifying enzymes associated with conjugated double bond formation comprising modification of the delta-9 position of fatty acids from other plants fatty acid modifying enzymes which are capable of modifying the delta-9 position of a fatty acid can now be identified by when nucleotide sequence hybridizes to any of the nucleotide sequences set forth in SEQ ID NOS:1, 3, and 12 under conditions of moderate stringency, as set forth above, or (b) is at least 40% identical to a polypeptide encoded by any of the nucleotide sequences set forth in SEQ ID NOs:1, 3, or 12 or a functionally equivalent subfragment thereof as determined by a comparison method designed to detect homologous sequences.

The amino acid sequences encoded by these nucleotide sequences disclosed herein are compared in FIG. 2 to the sequences encoding enzymes involved in conjugated fatty acid synthesis in Impatiens, Momordica, Chrysobalanus, and delta-12 desaturases from Helianthus and Borago, as well as the fatty acid desaturases from soybean which inserts the second double bond between carbon atoms 12 and 13 into monounsaturated fatty acid, oleic acid to produce linoleic acid.

The isolated nucleic acid fragments of the instant invention, or functionally equivalent subfragments thereof, or the complement thereof, can be used to create chimeric genes to transform host cells or plants. Examples of host cells which can be transformed include prokaryotic and eukaryotic cells. There can be mentioned microorganisms such as the bacterium *E. coli* and yeast *Saccharomyces cerevisiae*. Examples of plant cells include but are not limited to those obtained from soybean, oilseed Brassica species, corn, peanut, rice, wheat, sunflower, safflower, cotton, palm, flax, and cocoa.

Thus, the chimeric genes of the instant invention can be used to create transgenic plants in which the fatty acid modifying enzymes which modify the delta-9 position of fatty acids in seeds of *Calendula officinalis* or *Dimorphotheca sinuata* are present at higher levels than normal or in cell types or developmental stages in which it is not normally found. Also of interest are seeds obtained from such plants and oil obtained from these seeds.

Transgenic plants can be made in which fatty acid modifying enzyme associated with modification of the delta-9 position of fatty acids is present at lower levels than normal or in cell types or developmental stages in which it is not normally found. This would have the effect of altering the level of such fatty acids comprising a modified delta-9 position in those cells. It may be desirable to reduce or eliminate expression of a gene encoding such enzymes in plants for some applications. In order to accomplish this, a chimeric gene designed for co-suppression of the endogenous enzyme can be constructed by linking a gene or gene fragment encoding a fatty acid modifying enzyme associated with modification of the delta-9 position of fatty acids to plant promoter sequences. Alternatively, a chimeric gene designed to express antisense RNA for all or part of the instant nucleic acid fragment can be constructed by linking the gene or a gene fragment in reverse orientation to plant promoter sequences. Either the co-suppression or antisense chimeric genes could be introduced into plants via transformation wherein expression of the corresponding endogenous genes are reduced or eliminated.

When over-expressed in plant cells, the fatty acid modifying enzymes associated with modification of the delta-9 position of fatty acids in seeds of *Calendula officinalis* or *Dimorphotheca sinuata* can be useful for causing the biosynthesis and accumulation of fatty acids with conjugated double bonds, such as calendic acid, in those cells. It is particularly useful to use fatty acid modifying enzymes associated with modification of the delta-9 position of fatty acids in seeds of *Calendula officinalis* or *Dimorphotheca sinuata* to produce fatty acids containing conjugated double bonds in the cells of the seeds of oilseed crop plants.

Overexpression of fatty acid modifying enzymes associated with modification of the delta-9 position of fatty acids in seeds of *Calendula officinalis* or *Dimorphotheca sinuata* may be accomplished by first constructing a chimeric gene in which the coding region of cDNAs for fatty acid modifying enzymes associated with modification of the delta-9 position of fatty acids in seeds of *Calendula officinalis* or *Dimorphotheca sinuata* is operably linked to a promoter capable of directing expression of a gene in the desired tissues at the desired stage of development. For reasons of convenience, the chimeric gene may comprise a promoter sequence and translation leader sequence derived from the same gene. 3' non-coding sequences encoding transcription termination signals must also be provided. The instant chimeric genes may also comprise one or more introns in order to facilitate gene expression.

Vectors, such as plasmid vectors, comprising the instant chimeric genes can then be constructed. The choice of plasmid vector is dependent upon the method that will be used to transform host plants. The skilled artisan is well aware of the genetic elements that must be present on the plasmid vector in order to successfully transform, select and propagate host cells or plants containing the chimeric gene. The skilled artisan will also recognize that different independent transformation events will result in different levels and patterns of expression (Jones et al., (1985) *EMBO J.* 4:2411–2418; De Almeida et al., (1989) *Mol. Gen. Genetics* 218:78–86), and thus that multiple events must be screened in order to obtain lines displaying the desired expression level and pattern. Such screening may be accomplished by Southern analysis of DNA, Northern analysis of mRNA expression, Western analysis of protein expression, or phenotypic analysis.

For some applications it may be useful to direct the instant fatty acid modifying enzymes associated with modification of the delta-9 position of fatty acids in seeds of *Calendula officinalis* or *Dimorphotheca sinuata* to different cellular compartments, or to facilitate its secretion from the cell. It is thus envisioned that the chimeric genes described above may be further supplemented by altering the coding sequences to encode fatty acid modifying enzymes associated with modification of the delta-9 position of fatty acids in seeds of *Calendula officinalis* or *Dimorphotheca sinuata* disclosed herein with appropriate intracellular targeting sequences such as transit sequences (Keegstra, K. (1989) *Cell* 56:247–253), signal sequences or sequences encoding endoplasmic reticulum localization (Chrispeels, J. J., (1991) *Ann. Rev. Plant Phys. Plant Mol. Biol.* 42:21–53), or nuclear localization signals (Raikhel, N. (1992) *Plant Phys.* 100:1627–1632) added and/or with targeting sequences that are already present removed. While the references cited give examples of each of these, the list is not exhaustive and more targeting signals of utility may be discovered in the future.

The nucleic acid fragments of the instant invention, or functionally equivalent subfragment thereof, may be used to isolate cDNAs and other nucleic acid fragments encoding homologous fatty acid modifying enzymes from the same or other plant species. Isolation of homologous genes using sequence-dependent protocols is well known in the art. Examples of sequence-dependent protocols include, but are not limited to, methods of nucleic acid hybridization, and methods of DNA and RNA amplification as exemplified by various uses of nucleic acid amplification technologies (e.g., polymerase chain reaction, ligase chain reaction). The term "conserved sequence(s)" as used herein encompasses both strict conservation as well as conservation of a majority of the sequences used in an alignment, for example, conservation with respect to a consensus sequence.

Thus, in still a further aspect this invention concerns a method to isolate nucleic acid fragments and functionally equivalent subfragments thereof encoding a plant fatty acid modifying enzyme associated with modification of the delta-9 position of fatty acids comprising:

(a) comparing SEQ ID NOs:2, 4, or 13 and other plant fatty acid modifying enzyme polypeptide sequences;

(b) identifying conserved sequences of 4 or more amino acids obtained in step (a);

(c) designing degenerate oligomers based on the conserved sequences identified in step (b); and (d) using the degenerate oligomers of step (s) to isolate sequences encoding a plant fatty acid modifying enzyme or a portion thereof associated with modification of the delta-9 position of fatty acids by sequence dependent protocols.

For example, genes encoding homologous fatty acid modifying enzymes, either as cDNAs or genomic DNAs, could be isolated directly by using all or a portion of the instant nucleic acid fragments as DNA hybridization probes to screen libraries from any desired plant employing methodology well known to those skilled in the art. Specific oligonucleotide probes based upon the instant nucleic acid sequences can be designed and synthesized by methods known in the art (Sambrook). Moreover, the entire sequences can be used directly to synthesize DNA probes by methods known to the skilled artisan such as random primers DNA labeling, nick translation, or end-labeling techniques, or RNA probes using available in vitro transcription systems. In addition, specific primers can be designed and used to amplify a part of or full-length of the instant sequences. The resulting amplification products can be labeled directly during amplification reactions or labeled after amplification reactions, and used as probes to isolate full length cDNA or genomic fragments under conditions of appropriate stringency.

In addition, two short segments of the instant nucleic acid fragments may be used in polymerase chain reaction protocols to amplify longer nucleic acid fragments encoding homologous genes from DNA or RNA. The polymerase chain reaction may also be performed on a library of cloned nucleic acid fragments wherein the sequence of one primer is derived from the instant nucleic acid fragments, and the sequence of the other primer takes advantage of the presence of the polyadenylic acid tracts to the 3' end of the mRNA precursor encoding plant genes. Alternatively, the second primer sequence may be based upon sequences derived from the cloning vector. For example, the skilled artisan can follow the RACE protocol (Frohman et al., (1988) *PNAS USA* 85:8998) to generate cDNAs by using PCR to amplify copies of the region between a single point in the transcript and the 3' or 5' end. Primers oriented in the 3' and 5' directions can be designed from the instant sequences. Using commercially available 3' RACE or 5' RACE systems (BRL), specific 3' or 5' cDNA fragments can be isolated (Qhara et al., (1989) *PNAS USA* 86:5673; Loh et al., (1989) *Science* 243:217). Products generated by the 3' and 5' RACE procedures can be combined to generate full-length cDNAs (Frohman, M. A. and Martin, G. R., (1989) *Techniques* 1:165).

Thus, other nucleic acid fragments encoding enzymes associated with modification of the delta-9 position of fatty acids can be identified using any of the general methodologies described above. For example, a general group of fatty acid desaturase (FAD) related cDNAs, can be identified and a specific subset of those cDNAs encoding enzymes involved in modification of the delta-9 position of fatty acids can be detected or screened by transformation. A group of cDNA sequences encoding fatty acid desaturase-like enzymes can be identified using low-stringency hybridization (for example 2×SSC, 0.1% SDS, 60° C.) with a probe corresponding to any known FAD sequence, and/or all-or-part of the sequences presented in any of SEQ ID NOs:1, 3, or 12. Alternatively, randomly sequenced cDNAs can be analyzed by a computer program designed to detect homologous sequences, such as, but not limited to, BLAST or gapped BLAST (using standard default parameters). BLAST (Basic Local Alignment Search Tool; Altschul et al. (1993) *J. Mol. Biol.* 215:403–410) searches for similarity to sequences contained in the BLAST "nr" database (comprising all non-redundant GenBank CDS translations, sequences derived from the 3-dimensional structure Brookhaven Protein Data Bank, the last major release of the SWISS-PROT protein sequence database, EMBL, and DDBJ databases). Test sequences are analyzed for similarity to all publicly available DNA sequences contained in the "nr" database using the BLASTN algorithm provided by the National Center for Biotechnology Information (NCBI). The DNA sequences are translated in all reading frames and compared for similarity to all publicly available protein sequences contained in the "nr" database using the BLASTX algorithm (Gish and States (1993) *Nature Genetics* 3:266–272) provided by the NCBI. For convenience, the P-value (probability), or "pLog" (the negative of the logarithm of the P-value), is given as a measure of similarity between the two sequences. A test sequence and a sequence contained in the searched databases are compared, and the probability that the two sequences are related only by chance is calculated by BLAST and reported as a "pLog" value. Accordingly, the greater the pLog value, the greater the likelihood that the cDNA sequence and the BLAST "hit" represent homologous proteins. Sequences with pLogs greater than 5, or preferably greater than 10, or more preferably greater than 15, and most preferably greater than 20, that are defined as FADs or lipid desaturases are candidates. cDNAs encoding enzymes associated with modification of the delta-9 position of fatty acids can be identified from the candidate pools using transformation screening. Individual cDNAs are inserted into expression vectors and transformed into yeast or plant host cells using methods well known to those skilled in the art (see Examples 3, 4, 6, 7, and 8). Production of fatty acids containing conjugated double bonds is confirmed by GC-MS analyses as described in the Examples 3 and 4. Yeast or plant tissue culture cells are preferred for initial screening due to speed and the ease with which they can be handled when dealing with large numbers of transformants and the appropriate cell biology and eukaryotic cell physiology.

The instant fatty acid modifying enzymes associated with modification of the delta-9 position of fatty acids in seeds of *Calendula officinalis* or *Dimorphotheca sinuata* produced in heterologous host cells or plants, particularly in the cells of microbial hosts, can be used to prepare antibodies to the fatty acid modifying enzymes associated with modification of the delta-9 position of fatty acids in seeds of *Calendula officinalis* or *Dimorphotheca sinuata* by methods well known to those skilled in the art. The antibodies are useful for detecting the instant fatty acid modifying enzymes associated with modification of the delta-9 position of fatty acids in seeds of *Calendula officinalis* or *Dimorphotheca sinuata* in situ in cells or in vitro in cell extracts. Preferred heterologous host cells for production of the instant fatty acid modifying enzymes associated with modification of the delta-9 position of fatty acids in seeds of *Calendula officinalis* or *Dimorphotheca sinuata* are microbial hosts. Microbial expression systems and expression vectors containing regulatory sequences that direct high level expression of foreign proteins are well known to those skilled in the art. Any of these could be used to construct chimeric genes for production of the instant fatty acid modifying enzymes associated with modification of the delta-9 position of fatty acids in seeds of *Calendula officinalis* or *Dimorphotheca sinuata*. These chimeric genes could then be introduced into appropriate microorganisms via transformation to provide high level expression of the encoded fatty acid modifying enzymes associated with modification of the delta-9 position of a fatty acid in seeds *Calendula officinalis* or *Dimorphotheca sinuata*. An example of the use of the *Calendula officinalis* or *Dimorphotheca sinuata* fatty acid modifying enzyme in *Saccharomyces cerevisiae* for the production of calendic acid is discussed below in Example 4. An example of a vector for high level expression of the instant fatty acid modifying enzymes associated with modification of the delta-9 position of fatty acids in seeds of *Calendula officinalis* or *Dimorphotheca sinuata* in a bacterial host is discussed below in Example 8.

In still another aspect, it has been found that fatty acids modified at the delta-9 position, and in particular, those fatty acids having conjugated double bonds comprising the delta-9 position, more specifically, conjugated linolenic acids can also be used as an animal feed additive. The quality of meat grown for consumption is dependent upon many variables that ultimately influence market demand for the product. For instance, pork quality improvement is a primary focus of the pork industry. Quality variables include pork color, water holding capacity, size, chemical composition and firmness of lean and fat tissue. Experiments have shown that the fat firmness of pork can be influenced by the addition of conjugated linoleic acid ($18:2\Delta^{9cis, 11trans}$ or $\Delta^{10trans, 12cis}$) to swine diets (Eggert, J. M., et al. (1999) *J. Anim. Sci.* 77(*Suppl*):53; Thiel, R. C., et al. (1998)*J. Anim. Sci.* 76(*Suppl*):13; Wiegand, B. R., F. C. Parrrish Jr and J. C. Sparks (1999) *J. Anim. Sci.* 77(*Suppl*):19; U.S. Pat. No. 5,554,646; and U.S. Pat. No. 5,851,572). Some experiments have also reported improved carcass leanness and the efficiency of feed utilization when conjugated linoleic acid (CLA) is added as a supplement to the diet. It is not known whether feeding of different conjugated fatty acids would have similar effects. The present invention describes the production of conjugated double bonds in 18:3 and 18:4 fatty acids which are derived from 18:3 fatty acids in transgenic seeds that can be used as feed additives.

Thus, the instant invention concerns animal feed comprising an ingredient derived from the processing of any of the seeds obtained plants or plant cells transformed with any of the chimeric genes. The ingredient or conjugated linolenic acid should be present in a carcass quality improving amount. A "carcass quality improving amount" is that amount needed to improve the carcass quality of an animal. The ingredient can be a mixture of fatty acids obtained from such seeds. This mixture can be in any form suitable for use as a feed additive. For example, the mixture can be in the form of an oil whether or not it is saponified.

Also of interest is animal feed comprising oil obtained from any of the foregoing seeds. This invention also includes a method of improving the carcass quality of an animal by supplementing a diet of the animal with any of the animal feeds discussed above.

In a further aspect the present invention also concerns an isolated nucleic acid fragment encoding a plant fatty acid modifying enzyme (DMFad2-1) associated with modification of the delta-12 position of oleic acid to produce trans-linoleic acid, wherein said fragment or a functionally equivalent subfragment thereof (a) hybridizes to any of the nucleotide sequences set forth in SEQ ID NO:10 under conditions of moderate stringency or (b) is at least 75% identical to a polypeptide encoded by any of the nucleotide sequences set forth in SEQ ID NO:11 or a functionally equivalent subfragment thereof as determined by a comparison method designed to detect homologous sequences.

This invention also concerns an isolated nucleic acid fragment encoding a plant fatty acid modifying enzyme wherein said enzyme modifies a delta-12 position of fatty acids and further wherein said fragment or a functionally equivalent subfragment thereof (a) hybridizes to any of the nucleotide sequences set forth in SEQ ID NO:10 under conditions of moderate stringency or (b) is at least 75% identical to a polypeptide encoded by the nucleotide sequence set forth in SEQ ID NOs:11 or a functionally equivalent subfragment thereof as determined by a comparison method designed to detect homologous sequences.

This invention also relates to the following:

a) an isolated nucleic acid fragment encoding a plant fatty acid modifying enzyme associated with conjugated double bond formation comprising the delta-12 position of fatty acids wherein said fragment encodes a protein comprising any one of the amino acid sequences set forth in SEQ ID NO:11, as well as b) an isolated nucleic acid fragment encoding a plant fatty acid modifying enzyme wherein said enzyme modifies a delta-12 position of fatty acids and further wherein said fragment or a functionally equivalent subfragment thereof encodes a protein comprising any one of the amino acid sequences set forth in SEQ ID NO:11.

In another aspect, this invention concerns an isolated nucleic acid fragment encoding a plant fatty acid modifying enzyme associated with conjugated double bond formation comprising a the delta-12 position of fatty acids or an isolated nucleic acid fragment encoding a plant fatty acid modifying enzyme wherein said enzyme modifies the delta-12 position of the fatty wherein said fragments or a functionally equivalent subfragments thereof hybridize to any of the isolated nucleic acid fragments or functionally equivalent subfragments thereof encoding a plant fatty acid modifying enzyme associated with conjugated double bond formation comprising the delta-12 position of fatty acids or associated with modification of the delta-12 position wherein said fragments or subfragments encode a protein comprising any one of the amino acid sequences set forth in SEQ ID NO:11 and further wherein said fragments or subfragments (a) hybridize to these isolated nucleic acid fragments or functionally equivalent subfragments under conditions of moderate stringency or (b) is at least 75% identical to a polypeptide encoded by any of the foregoing isolated nucleic acid fragments or a functionally equivalent subfragments thereof as determined by a comparison method designed to detect homologous sequences. Examples of suitable comparison methods which detect homologous sequences are discussed above.

Also of interest is a chimeric gene comprising any of the instant isolated nucleic acid fragments, or functionally equivalent subfragments thereof, or a complement thereof operably linked to suitable regulatory sequences wherein expression of the chimeric gene results in production of altered levels of the desired enzyme in a transformed host cell or plant.

The invention also relates to methods of using such isolated nucleic acid fragments, or functionally equivalent subfragments thereof, or the complement thereof, to alter the level of fatty acids comprising a modification of the delta-12 position of fatty acids in a host cell or plant which comprises:

(a) transforming a host cell or plant with any of the instant chimeric genes;

(b) growing the transformed host cell or plant under conditions suitable for the expression of the chimeric gene; and (c) selecting those transformed host cells or plants having altered levels of fatty acids comprising a modification at the delta-12 position.

In still another aspect, this invention concerns a method for producing seed oil containing fatty acids comprising a modification at the delta-12 position in the seeds of plants which comprises:

(a) transforming a plant cell with any of the instant chimeric genes;

(b) growing a fertile mature plant from the transformed plant cell of step (a);

(c) screening progeny seeds from the fertile plants of step (b) for altered levels of fatty acids comprising a modification at the delta-12 position; and (d) processing the progeny seed of step (c) to obtain seed oil containing altered levels plant fatty acids comprising a modification at the delta-12 position.

In still a further aspect, this invention concerns a method for producing plant fatty acid modifying enzymes associated with modification of the delta-12 position of fatty acids which comprises:

(a) transforming a microbial host cell with any of the instant chimeric genes;

(b) growing the transformed host cell under conditions suitable for the expression of the chimeric gene; and (c) selecting those transformed host cells containing altered levels of protein encoded by the chimeric gene.

The isolated nucleic acid fragments encoding fatty acid modifying enzymes associated with conjugated double bond formation comprising the delta-12 position of fatty acids in seeds of *Dimorphotheca sinuata* is provided in SEQ ID NO:10, and the corresponding deduced amino acid sequences are provided in SEQ ID NO:11. Fatty acid modifying enzymes associated with conjugated double bond formation comprising modification of the delta-12 position of fatty acids from other plants fatty acid modifying enzymes which are capable of modifying the delta-12 position of a fatty acid can now be identified by when nucleotide sequence hybridizes to any of the nucleotide sequences set forth in SEQ ID NO:10 under conditions of moderate stringency, as set forth above, or (b) is at least 75% identical to a polypeptide encoded by any of the nucleotide sequences set forth in SEQ ID NO:10 or a functionally equivalent subfragment thereof as determined by a comparison method designed to detect homologous sequences.

Thus, the chimeric genes of the instant invention can be used to create transgenic plants in which the fatty acid modifying enzymes which modify the delta-12 position of fatty acids in seeds of *Dimorphotheca sinuata* are present at higher levels than normal or in cell types or developmental stages in which it is not normally found. Also of interest are seeds obtained from such plants and oil obtained from these seeds.

Transgenic plants can be made in which fatty acid modifying enzyme associated with modification of the delta-12 position of fatty acids is present at lower levels than normal or in cell types or developmental stages in which it is not normally found. This would have the effect of altering the level of such fatty acids comprising a modified delta-12 position in those cells. It may be desirable to reduce or eliminate expression of a gene encoding such enzymes in plants for some applications. In order to accomplish this, a chimeric gene designed for co-suppression of the endogenous enzyme can be constructed by linking a gene or gene fragment encoding a fatty acid modifying enzyme associated with modification of the delta-12 position of fatty acids to plant promoter sequences. Alternatively, a chimeric gene designed to express antisense RNA for all or part of the instant nucleic acid fragment, can be constructed by linking the gene or a gene fragment in reverse orientation to plant promoter sequences. Either the co-suppression or antisense chimeric genes could be introduced into plants via transformation wherein expression of the corresponding endogenous genes are reduced or eliminated.

When overexpressed in plant cells, the fatty acid modifying enzymes associated with modification of the delta-12 position of fatty acids in seeds of *Dimorphotheca sinuata* can be useful for causing the biosynthesis and accumulation of fatty acids with conjugated double bonds, such as calendic acid, in those cells. It is particularly useful to use fatty acid modifying enzymes associated with modification of the delta-12 position of fatty acids in seeds of *Dimorphotheca sinuata* to produce fatty acids containing conjugated double bonds in the cells of the seeds of oilseed crop plants. The modification of the delta-12 position by DMFad2-1 leads to an intermediate (trans-linoleic acid) that is the precursor to dimorphecolic acid.

Overexpression of fatty acid modifying enzymes associated with modification of the delta-12 position of fatty acids in seeds of *Dimorphotheca sinuata* may be accomplished by first constructing a chimeric gene in which the coding region of cDNAs for fatty acid modifying enzymes associated with modification of the delta-12 position of fatty acids in seeds of *Dimorphotheca sinuata* is operably linked to a promoter capable of directing expression of a gene in the desired tissues at the desired stage of development. For reasons of convenience, the chimeric gene may comprise a promoter sequence and translation leader sequence derived from the same gene. 3' non-coding sequences encoding transcription termination signals must also be provided. The instant chimeric genes may also comprise one or more introns in order to facilitate gene expression.

Vectors, such as plasmid vectors, comprising the instant chimeric genes can then be constructed. The choice of plasmid vector is dependent upon the method that will be used to transform host plants. The skilled artisan is well aware of the genetic elements that must be present on the plasmid vector in order to successfully transform, select and propagate host cells or plants containing the chimeric gene. The skilled artisan will also recognize that different independent transformation events will result in different levels and patterns of expression (Jones et al., (1985) *EMBO J.* 4:2411–2418; De Almeida et al., (1989) *Mol. Gen. Genetics* 218:78–86), and thus that multiple events must be screened in order to obtain lines displaying the desired expression level and pattern. Such screening may be accomplished by Southern analysis of DNA, Northern analysis of mRNA expression, Western analysis of protein expression, or phenotypic analysis.

For some applications it may be useful to direct the instant fatty acid modifying enzymes associated with modification of the delta-12 position of fatty acids in seeds of *Dimorphotheca sinuata* to different cellular compartments, or to facilitate its secretion from the cell. It is thus envisioned that the chimeric genes described above may be further supplemented by altering the coding sequences to encode fatty acid modifying enzymes associated with modification of the delta-12 position of fatty acids in seeds of *Dimorphotheca sinuata* disclosed herein with appropriate intracellular targeting sequences, such as transit sequences (Keegstra, K. (1989) *Cell* 56:247–253), signal sequences or sequences encoding endoplasmic reticulum localization (Chrispeels, J. J., (1991) *Ann. Rev. Plant Phys. Plant Mol. Biol.* 42:21–53), or nuclear localization signals (Raikhel, N. (1992) *Plant Phys.* 100:1627–1632) added and/or with targeting sequences that are already present removed. While the references cited give examples of each of these, the list is not exhaustive and more targeting signals of utility may be discovered in the future.

The nucleic acid fragments of the instant invention, or functionally equivalent subfragment thereof, may be used to isolate cDNAs and other nucleic acid fragments encoding homologous fatty acid modifying enzymes from the same or other plant species. Isolation of homologous genes using sequence-dependent protocols is well known in the art. Examples of sequence-dependent protocols include, but are not limited to, methods of nucleic acid hybridization, and methods of DNA and RNA amplification as exemplified by various uses of nucleic acid amplification technologies (e.g., polymerase chain reaction, ligase chain reaction). The term "conserved sequence(s)" as used herein encompasses both strict conservation as well as conservation of a majority of the sequences used in an alignment, for example, conservation with respect to a consensus sequence.

Thus, in still a further aspect this invention concerns a method to isolate nucleic acid fragments and functionally equivalent subfragments thereof encoding a plant fatty acid modifying enzyme associated with modification of the delta-12 position of fatty acids comprising:

(a) comparing SEQ ID NO:11 and other plant fatty acid modifying enzyme. polypeptide sequences;

(b) identifying conserved sequences of 4 or more amino acids obtained in step (a);

(c) designing degenerate oligomers based on the conserved sequences identified in step (b); and (d) using the degenerate oligomers of step (s) to isolate sequences encoding a plant fatty acid modifying enzyme or a portion thereof associated with modification of the delta-12 position of fatty acids by sequence dependent protocols.

For example, genes encoding homologous fatty acid modifying enzymes, either as cDNAs or genomic DNAs, could be isolated directly by using all or a portion of the instant nucleic acid fragments as DNA hybridization probes to screen libraries from any desired plant employing methodology well known to those skilled in the art. Specific oligonucleotide probes based upon the instant nucleic acid sequences can be designed and synthesized by methods known in the art (Sambrook). Moreover, the entire sequences can be used directly to synthesize DNA probes by methods known to the skilled artisan such as random primers DNA labeling, nick translation, or end-labeling techniques, or RNA probes using available in vitro transcription systems. In addition, specific primers can be designed and used to amplify a part of or full-length of the instant sequences. The resulting amplification products can be labeled directly during amplification reactions or labeled after amplification reactions, and used as probes to isolate full length cDNA or genomic fragments under conditions of appropriate stringency.

In addition, two short segments of the instant nucleic acid fragments may be used in polymerase chain reaction protocols to amplify longer nucleic acid fragments encoding homologous genes from DNA or RNA. The polymerase chain reaction may also be performed on a library of cloned nucleic acid fragments wherein the sequence of one primer is derived from the instant nucleic acid fragments, and the sequence of the other primer takes advantage of the presence of the polyadenylic acid tracts to the 3' end of the mRNA precursor encoding plant genes. Alternatively, the second primer sequence may be based upon sequences derived from the cloning vector. For example, the skilled artisan can follow the RACE protocol (Frohman et al., (1988) *PNAS*

USA 85:8998) to generate cDNAs by using PCR to amplify copies of the region between a single point in the transcript and the: 3' or 5' end. Primers oriented in the 3' and 5' directions can be designed from the instant sequences. Using commercially available 3' RACE or 5' RACE systems (BRL), specific 3' or 5' cDNA fragments can be isolated (Ohara et al., (1989) *PNAS USA* 86:5673; Loh et al., (1989) *Science* 243:217). Products generated by the 3' and 5' RACE procedures can be combined to generate full-length cDNAs (Frohman, M. A. and Martin, G. R., (1989) *Techniques* 1:165).

Thus, other nucleic acid fragments encoding enzymes associated with modification of the delta-12 position of fatty acids can be identified using any of the general methodologies described above. For example, a general group of fatty acid desaturase (FAD) related cDNAs, can be identified and a specific subset of those cDNAs encoding enzymes involved in modification of the delta-12 position of fatty acids can be detected or screened by transformation. A group of cDNA sequences encoding fatty acid desaturase-like enzymes can be identified using low-stringency hybridization (for example 2×SSC, 0.1% SDS, 60° C.) with a probe corresponding to any known FAD sequence, and/or all-or-part of the sequences presented in any of SEQ ID NO:10. Alternatively, randomly sequenced cDNAs can be analyzed by a computer program designed to detect homologous sequences, such as, but not limited to, BLAST or gapped BLAST (using standard default parameters). BLAST (Basic Local Alignment Search Tool; Altschul et al. (1993) *J. Mol. Biol.* 215:403–410) searches for similarity to sequences contained in the BLAST "nr" database (comprising all non-redundant GenBank CDS translations, sequences derived from the 3-dimensional structure Brookhaven Protein Data Bank, the last major release of the SWISS-PROT protein sequence database, EMBL, and DDBJ databases). Test sequences are analyzed for similarity to all publicly available DNA sequences contained in the "nr" database using the BLASTN algorithm provided by the National Center for Biotechnology Information (NCBI). The DNA sequences are translated in all reading frames and compared for similarity to all publicly available protein sequences contained in the "nr" database using the BLASTX algorithm (Gish and States (1993) *Nature Genetics* 3:266–272) provided by the NCBI. For convenience, the P-value (probability), or "pLog" (the negative of the logarithm of the P-value), is given as a measure of similarity between the two sequences. A test sequence and a sequence contained in the searched databases are compared, and the probability that the two sequences are related only by chance is calculated by BLAST and reported as a "pLog" value. Accordingly, the greater the pLog value, the greater the likelihood that the cDNA sequence and the BLAST "hit" represent homologous proteins. Sequences with pLogs greater than 5, or preferably greater than 10, or more preferably greater than 15, and most preferably greater than 20, that are defined as FADs or lipid desaturases are candidates. cDNAs encoding enzymes associated with modification of the delta-12 position of fatty acids can be identified from the candidate pools using transformation screening. Individual cDNAs are inserted into expression vectors and transformed into yeast or plant host cells using methods well known to those skilled in the art (see Examples 3, 4, 6, 7, and 8). Production of fatty acids containing conjugated double bonds is confirmed by GC-MS analyses as described in the Examples 3 and 4. Yeast or plant tissue culture cells are preferred for initial screening due to speed and the ease with which they can be handled when dealing with large numbers of transformants and the appropriate cell biology and eukaryotic cell physiology.

The instant fatty acid modifying enzymes associated with modification of the delta-12 position of fatty acids in seeds of *Dimorphotheca sinuata* produced in heterologous host cells or plants, particularly in the cells of microbial hosts, can be used to prepare antibodies to the fatty acid modifying enzymes associated with modification of the delta-12 position of fatty acids in seeds of *Dimorphotheca sinuata* by methods well known to those skilled in the art. The antibodies are useful for detecting the instant fatty acid modifying enzymes associated with modification of the delta-12 position of fatty acids in seeds of *Dimorphotheca sinuata* in situ in cells or in vitro in cell extracts. Preferred heterologous host cells for production of the instant fatty acid modifying enzymes associated with modification of the delta-12 position of fatty acids in seeds of *Dimorphotheca sinuata* are microbial hosts. Microbial expression systems and expression vectors containing regulatory sequences that direct high level expression of foreign proteins are well known to those skilled in the art. Any of these could be used to construct chimeric genes for production of the instant fatty acid modifying enzymes associated with modification of the delta-12 position of fatty acids in seeds of *Dimorphotheca sinuata*. These chimeric genes could then be introduced into appropriate microorganisms via transformation to provide high level expression of the encoded fatty acid modifying enzymes associated with modification of the delta-12 position of a fatty acid in seeds *Dimorphotheca sinuata*. An example of a vector for high level expression of the instant fatty acid modifying enzymes associated with modification of the delta-12 position of fatty acids in seeds of *Dimorphotheca sinuata* in a bacterial host is discussed below in Example 8.

EXAMPLES

The present invention is further defined in the following Examples, in which all parts and percentages are by weight and degrees are Celsius, unless otherwise stated. It should be understood that these Examples, while indicating preferred embodiments of the invention, are given by way of illustration only. From the above discussion and these Examples, one skilled in the art can ascertain the essential characteristics of this invention, and without departing from the spirit and scope thereof, can make various changes and modifications of the invention to adapt it to various usages and conditions.

Example 1

Composition of cDNA Libraries; Isolation and Sequencing of cDNA Clones cDNA libraries representing mRNAs from developing seeds of *Calendula officinalis* were prepared. The seeds chosen were actively accumulating fatty acids with conjugated double bonds. The libraries were prepared using a Uni-ZAP™ XR kit according to the manufacturer's protocol (Stratagene Cloning Systems, La Jolla, Calif.), except that cDNAs were cloned into the EcoRI and XhoI sites of the bacterial vector pBluescript SK(−) rather than into a phage vector. Libraries were maintained in *E. coli* DH10B cells (Life Technologies, Gaithersburg, Md.). cDNA inserts from randomly picked bacterial colonies containing recombinant pBluescript plasmids were grown up and plasmid purified. cDNAs were sequenced using primers specific for vector sequences flanking the inserted cDNA sequences. Insert DNAs were sequenced in dye-primer sequencing reactions to generate partial cDNA sequences (expressed sequence tags or "ESTs"; see Adams, M. D. et al., (1991) *Science*

252:1651) using a Perkin Elmer Model 377 fluorescent sequencer. The resulting ESTs were analyzed using computational methods as described below.

Example 2

Identification and Characterization of cDNA Clones

ESTs encoding *Calendula officinalis* fatty acid modifying enzymes were identified by conducting BLAST (Basic Local Alignment Search Tool; Altschul, S. F., et al., (1993) *J. Mol. Biol.* 215:403–410) searches for similarity to sequences contained in the BLAST "nr" database (comprising all non-redundant GenBank coding sequence ["CDS"] translations, sequences derived from the 3-dimensional structure Brookhaven Protein Data Bank, the last major release of the SWISS-PROT protein sequence database, EMBL, and DDBJ databases). The cDNA sequences obtained in Example 1 were analyzed for similarity to all publicly available DNA sequences contained in the "nr" database using the BLASTN algorithm provided by the National Center for Biotechnology Information (NCBI). The DNA sequences were translated in all reading frames and compared for similarity to all publicly available protein sequences contained in the "nr" database using the BLASTX algorithm (Gish, W. and States, D. J. (1993) *Nature Genetics* 3:266–272) provided by the NCBI. For convenience, the P-value (probability) of observing a match of a cDNA sequence to a sequence contained in the searched databases merely by chance as calculated by BLAST are reported herein as "pLog" values, which represent the negative of the logarithm of the reported P-value. Accordingly, the greater the pLog value, the greater the likelihood that the cDNA sequence and the BLAST "hit" represent homologous proteins.

The BLASTX search using sequence information derived from the entire *Calendula officinalis* clone ecs1c.pk009.n14 (CalFad2-1) revealed strong similarity to the proteins encoded by cDNAs for omega-6 fatty acid desaturases from *Petroselinum crispum* (Genbank Accession No. gi2501790; pLog=133.00) and *Brassica juncea* (Genbank Accession No. gi3334184; pLog=127.00). The BLASTX search using sequence information derived from the entire *Calendula officinalis* clone ecs1c.pk008.a24 (CalFad2-2) revealed strong similarity to the proteins encoded by cDNAs for delta-12 fatty acid desaturases from *Borago officinalis* (Genbank Accession No. gi3417601; pLog=135.00) and *Brassica carinata* (Genbank Accession No. gi4378875; pLog=135.00). SEQ ID NO:1 shows the nucleotide sequence of the entire *Calendula officinalis* cDNA in clone ecs1c.pk009.n14; the deduced amino acid sequence is shown in SEQ ID NO:2. SEQ ID NO:3 shows the nucleotide sequence of the entire *Calendula officinalis* cDNA in clone ecs1c.pk008.a24; the deduced amino acid sequence is shown in SEQ ID NO:4. Sequence alignments and BLAST scores and probabilities indicate that the instant nucleic acid fragments encode *Calendula officinalis* proteins that is structurally related to the omega-6 and delta-12 class of fatty acid desaturases. The clones for these proteins were designated CalFad2-1 and CalFad2-2, respectively.

Example 3

Expression of CalFad2-1, a Diverged Calendula Fad2, in Tobacco Cells

To characterize the activity of the CalFad2-1 in transgenic plant cells, the cDNA (ecs1c.pk009.n14) encoding this enzyme was expressed in tobacco callus with the gene under control of the cauliflower mosaic virus 35S promoter. The open-reading frame of the cDNA for CalFad2-1 was amplified by PCR to generate flanking 5' BamHI and 3' SstI restriction enzyme sites for cloning into the plant expression vector. The sequence of the sense oligonucleotide used in the amplification reaction was 5'-tttgagctcTACACCTAGCTACGTACCATG-3' (SEQ ID NO:16), and the sequence of the antisense oligonucleotide was 5'-tttggatccTCACGGTACTGATGATGGCAC-3' (SEQ ID NO:17) [Note: the bases in lower case contain the added restriction sites, which are underlined, and flanking sequence to facilitate restriction enzyme digestion]. The design of the PCR primers was based on the sequence of the CalFad2-1 cDNA shown in SEQ ID NO:1. Thirty cycles of PCR amplification were conducted in a 100 μl volume using Pfu polymerase (Stratagene) and 25 ng of pBluescript SK(−) containing the CalFad2-1 cDNA. The product from this reaction was subcloned into pPCR-Script AMP (Stratagene). Following restriction digestion with BamHI and SstI, the PCR product was moved from pPCR-Script AMP into the corresponding sites of the plant expression vector pBI121 (Clontech). The vector pBI121 is used for constitutive expression of transgenes mediated by the cauliflower mosaic virus 35S promoter. This vector contains right and left border regions flanking the inserted gene fusion to facilitate stable Agrobacterium-mediated transformation of the host plant cell and also contains within the border regions a nopaline phosphotransferase II (NPTII) gene under control of the cauliflower mosaic virus 35S promoter to provide for selection of transformed plant cells by kanamycin resistance. The resulting construct containing the 35S promoter fused with CalFad2-1 cDNA was transformed into *Agrobacterium tumefaciens* LBA4404 cells. Cultures derived from these cells were used for transformation of tobacco (*Nicotiana tabacum* cv. Xanthi) leave disks according to the protocol described by Rogers, S. G., Horsch, R. B., and Fraley, R. T. (1986) *Methods Enzymol.* 118: 627–648.

Kanamycin-resistant tobacco callus that resulted from the transformation was examined for the presence of calendic acid arising from the activity of CalFad2-1. Fatty acid methyl esters were prepared by homogenization of the transgenic tobacco callus in 1% (w/v) sodium methoxide in methanol using methods described by Hitz et al. (1994) *Plant Physiol.* 105:635–641. The recovered fatty acid methyl esters were then analyzed using a Hewlett-Packard 6890 chromatograph fitted with an Omegawax 320 column (30 m×0.32 mm inner diameter; Supelco). The oven temperature was programmed from 220° C. (2 min hold) to 240° C. at a rate of 20° C./min. The retention time of methyl calendic acid in extracts of tobacco callus was compared with that of methyl calendic acid in seeds of *Calendula officinalis*. Gas chromatography-mass spectrometry (GC-MS) was also performed to confirm the identity of calendic acid in tobacco callus expressing CalFad2-1. Fatty acid methyl prepared from the transgenic tobacco callus was analyzed with an HP6890 interfaced with a HP5973 (Hewlett-Packard) mass selective detector. Compounds were resolved using HP-5 column (30 m×0.25 mm inner diameter) with the oven temperature programmed from 185° C. (2-min hold) to 215° C. at a rate of 5° C./min. The mass spectrum of methyl calendic acid from Calendula seed extracts is characterized by an abundant molecular ion of 292 m/z.

Figure 3:
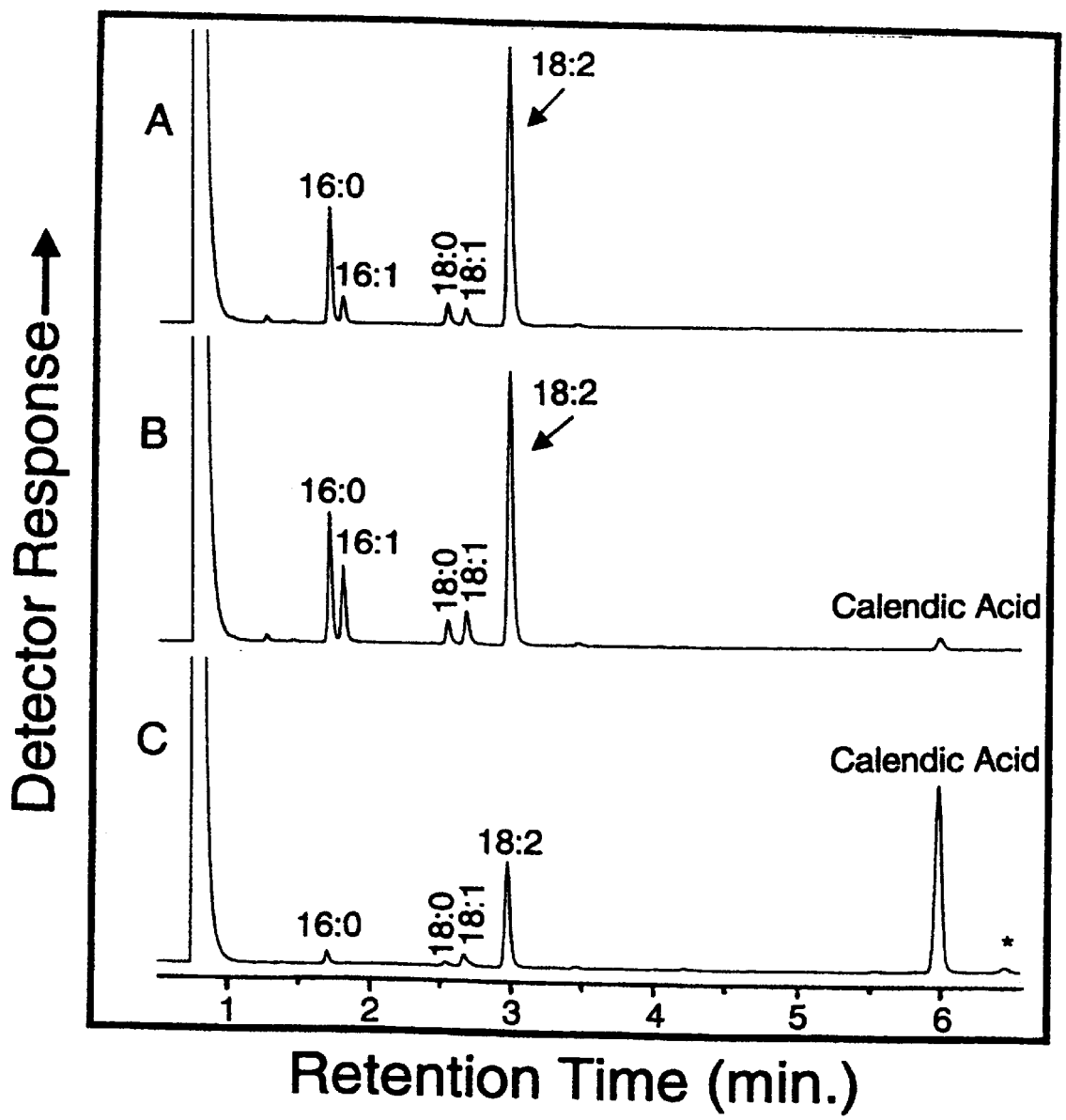

In fatty acid methyl esters prepared from the stably transformed tobacco callus, methyl calendic acid was detected in amounts of up to 11.4% of the total fatty acids (FIG. 3). The peak identified as methyl calendic acid in callus expressing CalFad2-1 had a retention time and mass spectrum that was identical to those of methyl calendic acid in *Calendula officinalis* seeds. No methyl calendic acid was detected in tobacco callus transformed with the vector lacking cDNA insert. These results further demonstrate the ability to produce calendic acid by transgenic expression of CalFad2-1.

Example 4

Expression of *Calendula officinalis* clones CalFad2-1 and CalFad2-2 in *Saccharomyces cerevisiae*

The *Calendula officinalis* clones CalFad2-1 and CalFad2-2 were digested with the restriction enzymes EcoRI and XhoI. The resulting DNA fragments containing the entire cDNA inserts were purified by agarose gel electrophoresis. The purified cDNAs were ligated into the EcoRI and XhoI sites of the *Saccharomyces cerevisiae* expression vector pYES2 (Invitrogen) using T4 DNA ligase (New England Biolabs). The resulting plasmids pYes2/CalFad2-1 and pYes2/CalFad2-2 were introduced into *Saccharomyces cerevisiae* INVSc1 (Invitrogen Corp.) cells by lithium acetate-mediated transformation [Sherman F, Fink G R, Hicks J B, *Methods in Yeast Genetics: A Laboratory Course Manual*, Cold Spring Harbor Lab. Press, Plainview, N.Y. (1987)]. Transformed cells were selected for their ability to grow in the absence of uracil. Individual colonies of transformed cells were then grown for 2 days at 30° C. in growth media lacking uracil [0.17% (w/v) yeast nitrogen base without amino acids (Difco), 0.5% (w/v) ammonium sulfate, and 0.18% SC-URA (Bio101)] supplemented with glycerol and glucose to a final concentration of 5% (v/v) and 0.5% (w/v), respectively. Cells were then washed twice in the growth media described above that was supplemented instead with galactose to a final concentration of 2% (w/v). The washed cells were then diluted to $O.D._{600} \sim 0.2$ in the galactose-containing growth media that also contained Tergitol NP-40 (Sigma) at a concentration of 0.2% (w/v). Aliquots of these cells were grown without exogenous fatty acids or with the addition of linoleic acid ($18:2\Delta^{9cis, 12cis}$) to a final concentration of 2 mM. Following 4 days of growth at 16° C., the *S. cerevisiae* cells were harvested and examined for the accumulation of fatty acids containing conjugated double bonds as described in Example 4. In cells grown in media containing linoleic acid, calendic acid ($18:3\Delta^{8tran, 10trans, 12cis}$) was detected in amounts of up to 2.9% (w/w) of the total fatty acids of cultures expressing CalFad2-1 (FIG. 3) and in amounts of up to 0.2% of the total fatty acids of cultures expressing CalFad2-2. The identity of calendic acid was established by comparison of the gas chromatographic retention time and mass spectrum of its methyl ester derivative with that of methyl calendic acid in extracts of Calendula seeds. No calendic acid was detected in cultures harboring the expression vector without a cDNA insert or in cells grown in the absence of exogenous linoleic acid. These data are consistent with linoleic acid serving as the substrate for calendic acid synthesis via the activity of the *Calendula officinalis* fatty acid modifying enzyme associated with conjugated double bond formation and modification of the delta-9 position of fatty acids. In this reaction, the delta-9 double bond of linoleic acid is converted by the activity of CalFad2-1 or CalFad2-2 to delta-8 and delta-10 double bonds. The resulting fatty acid, calendic acid, contains delta-8, delta-10, and delta-12 double bonds in conjugation. CalFad2-1 and CalFad2-2 are thus distinct from all previously reported Fad2-related polypeptides by their ability to modify the delta-9 rather than the delta-12 position of a fatty acid.

Example 5

Comparison of the Proteins from Calendula with Impatiens, Momordica, and Chrysobalanus Enzymes Involved in Conjugated Fatty acid Bond Formation, as well as Members of the Omega-6 Desaturase Class of Enzymes The deduced amino acid sequences from cDNA clones CalFad2-1, CalFad2-2, ImpFad2 H8, and MomFad2 were compared to the deduced amino acid sequences encoding (i) a known fatty acid desaturase from soybean (World Patent Publication No. WO94/11516) and (ii) a fatty acid hydroxylase from castor bean (van de Loo, F. J. et al. (1995) *Proc. Natl. Acad. Sci. U.S.A.* 92 (15):6743–6747) using the multiple sequence comparison program Megalign (v3.1.7) from the Lasergene□ software package (DNASTAR Inc., Madison, WI) and the Clustal method of alignment (default program parameters). The aligned sequences are shown in FIGS. 2A–2D. All seven sequences, including those of the proteins from *Calendula officinalis* are related by eight highly conserved histidine residues that are believed to be part of the binding site for the two-iron cluster that is required in the active site of this class of enzymes (Shanklin, J. et al. (1994) Biochemistry 33:12787–12793). These conserved residues are identified as boxed elements in FIGS. 2A–2D. The amino acid sequence encoded by the *Impatiens balsamina* cDNA clone ImpH8Fad2 is 57.0% identical to the soybean sequence and 55.2% identical to the castor sequence. The amino acid sequence encoded by the *Momordica charantia* cDNA clone MomFad2 is 56.7% identical to the soybean sequence and 53.5% identical to the castor sequence. Overall, the sequence similarity shared by the two *Calendula officinalis* proteins is 94.6%. CalFad2-1 is 45.5% identical to the soybean sequence and 44.1% identical to the castor sequence. CalFad2-2 is 46.8% identical to the soybean sequence and 44.1% identical to the castor sequence.

The residue immediately adjacent to the first histidine box in both Calendula enzymes is a glycine (as indicated by an asterisk in FIGS. 2A–2D). A glycine in this position is only observed in $\omega^6$-oleic acid desaturase-related enzymes that have diverged functionality, such as the castor oleic acid hydroxylase (van de Loo, F. J. et al. (1995) *Proc. Natl. Acad. Sci. U.S.A.* 92:6743–6747) and the *Crepis palaestina* epoxidase (Lee, M. et al. (1998) Science 280:915–918). Given this feature of its primary structure and its more distant relation to known $\omega^6$-oleic acid desaturases, it is believed that the polypeptides encoded by CalFad2-1 and CalFad2-2 are associated with conjugated double bond formation and are not conventional fatty acid desaturases (like the soybean sequence in FIGS. 2A–2D). The Impatiens enzyme (ImpFad2H8) is known to make eleostearic acid, a conjugated fatty acid, and also contains this glycine for alanine substitution.

Thus, changes in a comparatively small number of amino acid residues in conserved regions of the protein are sufficient to alter the activity in this class of enzymes from one of introducing a double bond (i.e., a desaturase) to one of introducing an hydroxyl group (i.e., a hydroxylase) or to one that is active in converting polyunsaturated fatty acids to fatty acids containing multiple conjugated double bonds.

Example 6

Expression of Chimeric Genes in Monocot Cells

The oil storing tissues of most grass seeds are the embryo and its attending tissues the scutellum and to some extent the aleurone. Promoter sequences such as those controlling expression of the storage proteins Globulin 1 (Belanger, S. C. and Kriz, A. L (1989) *Plant Physiol.* 91:636–643) and Globulin 2 (Wallace, N. H. and Kriz, A. L. (1991) *Plant Physiol.* 95:973–975) are appropriate for the expression of chimeric genes in these tissues.

A chimeric gene comprising a cDNA encoding fatty acid modifying enzymes associated with conjugated double bond synthesis comprising the delta-9 position in seeds of *Calendula officinalis* in sense orientation with respect to the maize Globulin 2 promoter that is located 5' to the cDNA fragment, and the Globulin 2, 3' end that is located 3' to the cDNA fragment, can be constructed. The cDNA fragment of this gene may be generated by polymerase chain reaction (PCR) of the cDNA clone using appropriate oligonucleotide primers. Cloning sites can be incorporated into the oligonucleotides to provide proper orientation of the DNA fragment when inserted into the correctly designed expression vector.

Such expression vectors should include genetic sequences elements conferring an origin of replication for the plasmid in its host, a gene capable of conferring a selectable trait such as autotrophy or antibiotic tolerance to the host cell carrying the plasmid and the promoter sequences for expression of desired genes in host plant cells. Further design features may include unique restriction endonuclease recognition sites between the elements of the plant gene promoter elements to allow convenient introduction genes to be controlled by those elements. Plants that can serve as suitable hosts include, but are not limited to, corn, rice, wheat, and palm.

The chimeric genes constructed as above can then be introduced into corn cells by the following procedure. Immature corn embryos can be dissected from developing caryopses derived from crosses of the inbred corn lines H99 and LH132. The embryos are isolated 10 to 11 days after pollination when they are 1.0 to 1.5 mm long. The embryos are then placed with the axis-side facing down and in contact with agarose-solidified N6 medium (Chu et al., (1975) *Sci. Sin. Peking* 18:659–668). The embryos are kept in the dark at 27°. Friable embryogenic callus consisting of undifferentiated masses of cells with somatic proembryoids and embryoids borne on suspensor structures proliferates from the scutellum of these immature embryos. The embryogenic callus isolated from the primary explant can be cultured on N6 medium and sub-cultured on this medium every 2 to 3 weeks.

The plasmid, p35S/Ac (obtained from Dr. Peter Eckes, Hoechst Ag, Frankfurt, Germany) may be used in transformation experiments in order to provide for a selectable marker. This plasmid contains the Pat gene (see European Patent Publication 0 242 236) which encodes phosphinothricin acetyl transferase (PAT). The enzyme PAT confers resistance to herbicidal glutamine synthetase inhibitors such as phosphinothricin. The pat gene in p35S/Ac is under the control of the 35S promoter from Cauliflower Mosaic Virus (Odell et al. (1985) *Nature* 313:810–812) and the 3' region of the nopaline synthase gene from the T-DNA of the Ti plasmid of *Agrobacterium tumefaciens*.

The particle bombardment method (Klein et al., (1987) *Nature* 327:70–73) may be used to transfer genes to the callus culture cells. According to this method, gold particles (1 µm in diameter) are coated with DNA using the following technique. Ten µg of plasmid DNAs are added to 50 µL of a suspension of gold particles (60 mg per mL). Calcium chloride (50 µL of a 2.5 M solution) and spermidine free base (20 µL of a 1.0 M solution) are added to the particles. The suspension is vortexed during the addition of these solutions. After 10 minutes, the tubes are briefly centrifuged (5 sec at 15,000 rpm) and the supernatant removed. The particles are resuspended in 200 µL of absolute ethanol, centrifuged again and the supernatant removed. The ethanol rinse is performed again and the particles resuspended in a final volume of 30 µL of ethanol. An aliquot (5 µL) of the DNA-coated gold particles can be placed in the center of a Kapton® flying disc (Bio-Rad Labs). The particles are then accelerated into the corn tissue with a Biolistic® PDS-1000/He (Bio-Rad Instruments, Hercules Calif.), using a helium pressure of 1000 psi, a gap distance of 0.5 cm and a flying distance of 1.0 cm.

For bombardment, the embryogenic tissue is placed on filter paper over agarose-solidified N6 medium. The tissue is arranged as a thin lawn and covered a circular area of about 5 cm in diameter. The petri dish containing the tissue can be placed in the chamber of the PDS-1000/He approximately 8 cm from the stopping screen. The air in the chamber is then evacuated to a vacuum of 28 inches of Hg. The macrocarrier is accelerated with a helium shock wave using a rupture membrane that bursts when the He pressure in the shock tube reaches 1000 psi.

Seven days after bombardment the tissue can be transferred to N6 medium that contains gluphosinate (2 mg per liter) and lacks casein or proline. The tissue continues to grow slowly on this medium. After an additional 2 weeks the tissue can be transferred to fresh N6 medium containing gluphosinate. After 6 weeks, areas of about 1 cm in diameter of actively growing callus can be identified on some of the plates containing the glufosinate-supplemented medium. Calli may continue to grow when sub-cultured on the selective medium.

Plants can be regenerated from the transgenic callus by first transferring clusters of tissue to N6 medium supplemented with 0.2 mg per liter of 2,4-D. After two weeks the tissue can be transferred to regeneration medium (Fromm et al., (1990) *Bio/Technology* 8:833–839).

Example 7

Expression of Chimeric Genes in Dicot Cells

Fatty acid modifying enzymes associated with conjugated double bond synthesis comprising the delta-9 position in seeds of *Calendula officinalis* can be expressed in cells of dicots that normally produce storage lipid by the construction of appropriate chimeric genes followed by stable introduction of those genes into the host plant. An example of this method is the seed specific expression in soybean of fatty acid modifying enzymes associated with conjugated double bond synthesis in seeds of *Calendula officinalis*. Other plants that can be used include, but are not limited to, oilseed Brassica species, peanut, sunflower, safflower, cotton, flax, and cocoa.

A plasmid pKS 18HH containing chimeric genes to allow expression of Hygromycin B Phosphotransferase in certain bacteria and in plant cells can be constructed from the following genetic elements: a) T7 Promoter+Shine-Delgarno/Hygromycin B Phosphotransferase (HPT)/T7 Terminator Sequence, b) 35S Promoter from cauliflower mosaic virus (CaMV)/Hygromycin B Phosphotransferase (HPT)/Nopaline Synthase (NOS3' from *Agrobacterium tumefaciens* T-DNA, and c) pSP72 plasmid vector [from Promega] with β-lactamase coding region (ampicillin resistance gene) removed.

The Hygromycin B Phosphotransferase gene can be amplified by PCR from *E. coli* strain W677, which contains a Klebsiella derived plasmid pJR225. Starting with the pSP72 vector the elements are assembled into a single plasmid using standard cloning methods (Maniatis).

Plasmid pKS 18HH thus contains the T7 promoter/HPT/T7 terminator cassette for expression of the HPT enzyme in certain strains of *E. coli,* such as NovaBlue(DE3) [from Novagen], that are lysogenic for lambda DE3 (which carries the T7 RNA Polymerase gene under lacV5 control). Plasmid pKS18HH also contains the 35S/HPT/NOS cassette for constitutive expression of the HPT enzyme in plants, such as soybean. These two expression systems allow selection for growth in the presence of hygromycin to be used as a means of identifying cells that contain the plasmid in both bacterial and plant systems.

pKS18HH also contains three unique restriction endonuclease sites suitable for the cloning of other chimeric genes into this vector.

A plasmid for expression of the cDNA encoding fatty acid modifying enzymes associated with conjugated double bond synthesis in seeds of *Calendula officinalis* is made to be under the control of a soybean β-conglycinin promoter (Beachy et al., (1985) *EMBO J.* 4:3047–3053). The construction of this vector is facilitated by the use of plasmids pCW109 and pML18, both of which have been described (see World Patent Publication No. WO94/11516).

A unique Not I site is introduced into the cloning region between the β-conglycinin promoter and the phaseolin 3' end in pCW109 by digestion with Nco I and Xba I followed by removal of the single stranded DNA ends with mung bean exonuclease. Not I linkers (New England Biochemical catalog number NEB 1125) are ligated into the linearized plasmid to produce plasmid pAW35. The single Not I site in pML18 is destroyed by digestion with Not I, filling in the single stranded ends with dNTP's and Klenow fragment followed by re-ligation of the linearized plasmid. The modified pML18 is then digested with Hind III and treated with CalFad intestinal phosphatase.

The β-conglycinin:Not I:phaseolin expression cassette in pAW35 is removed by digestion with Hind III and the 1.79 kB fragment is isolated by agarose gel electrophoresis. The isolated fragment is ligated into the modified and linearized pML18 construction described above. A clone with the desired orientation was identified by digestion with Not I and Xba I to release a 1.08 kB fragment indicating that the orientation of the β-conglycin transcription unit is the same as the selectable marker transcription unit. The resulting plasmid is given the name pBS19.

Hind III is one of the unique cloning sites available in pKS18HH. To assemble the final expression cassette pBS19 and pKS18HH are both digested with Hind III. The β-conglycinin containing fragment from pBS19 is isolated by gel electrophoresis and ligated into the digested pKS18HH which had been treated with CalFad alkaline phosphatase. The resulting plasmid is named pRB20.

The PCR products amplified from clones for the Calendula polypeptides (described in Example 3 above) are digested with restriction enzymes to cleave the sites designed into the PCR primers. Plasmid pRB20 is also digested in a manner compatible with conventional cloning sites for the introduction of the PCR fragments. After phosphatase treatment of the linearized pRB20, PCR products are ligated into pRB20 and the ligation mixtures are used to transform *E. coli* strain DH10B. Colonies are selected and grown in liquid media for preparation of plasmid DNA. Digestion of the plasmid DNAs with an enzyme diagnostic for correct orientation of the coding sequences relative to the β-conglycinin promoter identifies clones for use in soybean transformation.

Soybean embryos are then transformed with the expression vector comprising sequences encoding Calendula polypeptides described above. To induce somatic embryos, cotyledons, 3–5 mm in length dissected from surface sterilized, immature seeds of a soybean cultivar, such as A2872, can be cultured in the light or dark at 26° on an appropriate agar medium for 6–10 weeks. Somatic embryos which produce secondary embryos are then excised and placed into a suitable liquid medium. After repeated selection for clusters of somatic embryos that multiplied as early, globular staged embryos, the suspensions are maintained as described below.

Soybean embryogenic suspension cultures are maintained in 35 mL liquid media on a rotary shaker, 150 rpm, at 26° with fluorescent lights on a 16:8 hour day/night schedule. Cultures are subcultured every two weeks by inoculating approximately 35 mg of tissue into 35 mL of liquid medium.

Soybean embryogenic suspension cultures may then be transformed by the method of particle gun bombardment (Kline et al. (1987) Nature (London) 327:70, U.S. Pat. No. 4,945,050). A Du Pont Biolistic™ PDS 1000/HE instrument (helium retrofit) can be used for these transformations.

A selectable marker gene which can be used to facilitate soybean transformation is a chimeric gene composed of the 35S promoter from Cauliflower Mosaic Virus (Odell et al.(1985) *Nature* 313:810–812), the hygromycin phosphotransferase gene from plasmid pJR225 (from *E. coli;* Gritz et al.(1983) *Gene* 25:179–188) and the 3' region of the nopaline synthase gene from the T-DNA of the Ti plasmid of Agrobacterium tumefaciens. The seed expression cassette comprising the phaseolin 5' region, the fragment encoding the Calendula conjugated fatty acid modifying enzyme and the phaseolin 3' region can be isolated as a restriction fragment. This fragment can then be inserted into a unique restriction site of the vector carrying the marker gene.

To 50 μL of a 60 mg/mL 1 mm gold particle suspension is added (in order): 5 μL. DNA (1 μg/μL), 20 μL spermidine (0.1 M), and 50 μL CaCl$_2$ (2.5 M). The particle preparation is then agitated for three minutes, spun in a microfuge for 10 seconds and the supernatant removed. The DNA-coated particles are then washed once in 400 μL 70% ethanol and resuspended in 40 μL of anhydrous ethanol. The DNA/particle suspension can be sonicated three times for one second each. Five μL of the DNA-coated gold particles are then loaded on each macro carrier disk.

Approximately 300–400 mg of a two-week-old suspension culture is placed in an empty 60×15 mm petri dish and the residual liquid removed from the tissue with a pipette. For each transformation experiment, approximately 5–10 plates of tissue are normally bombarded. Membrane rupture pressure is set at 1100 psi and the chamber is evacuated to a vacuum of 28 inches mercury. The tissue is placed approximately 3.5 inches away from the retaining screen and bombarded three times. Following bombardment, the tissue can be divided in half and placed back into liquid and cultured as described above.

Five to seven days post bombardment, the liquid media may be exchanged with fresh media, and eleven to twelve days post bombardment with fresh media containing 50 mg/mL hygromycin. This selective media can be refreshed weekly. Seven to eight weeks post bombardment, green, transformed tissue may be observed growing from untransformed, necrotic embryogenic clusters. Isolated green tissue is removed and inoculated into individual flasks to generate new, clonally propagated, transformed embryogenic suspension cultures. Each new line may be treated as an independent transformation event. These suspensions can then be subcultured and maintained as clusters of immature embryos or regenerated into whole plants by maturation and germination of individual somatic embryos.

Using methods described in this Example, transformed soybean embryos with detectable levels of conjugated polyunsaturated fatty acids may be identified and propagated.

Example 8

Expression of Chimeric Genes in Microbial Cells

The cDNAs encoding the instant fatty acid modifying enzymes associated with conjugated double bond synthesis comprising the delta-9 position in seeds of *Calendula officinalis* can be inserted into the T7 *E. coli* expression vector pET24d (Novagen). For example, plasmid DNA containing a cDNA may be appropriately digested to release a nucleic acid fragment encoding the fatty acid modifying enzymes associated with conjugated double bond synthesis in seeds of *Calendula officinalis*. This fragment may then be purified on a 1% NuSieve GTG™ low melting agarose gel (FMC). Buffer and agarose contain 10 µg/ml ethidium bromide for visualization of the DNA fragment. The fragment can then be purified from the agarose gel by digestion with GELase™ (Epicentre Technologies) according to the manufacturer's instructions, ethanol precipitated, dried and resuspended in 20 µL of water. Appropriate oligonucleotide adapters may be ligated to the fragment using T4 DNA ligase (New England Biolabs, Beverly, Mass.). The fragment containing the ligated adapters can be purified from the excess adapters using low melting agarose as described above. The vector pET24d is digested, dephosphorylated with alkaline phosphatase (NEB) and deproteinized with phenol/chloroform as described above. The prepared vector pET24d and fragment can then be ligated at 16° for 15 hours followed by transformation into DH5 electrocompetent cells (GIBCO BRL). Transformants can be selected on agar plates containing 2×YT media and 50 µg/mL kanamycin. Transformants containing the gene are then screened for the correct orientation with respect to pET24d T7 promoter by restriction enzyme analysis.

Clones in the correct orientation with respect to the T7 promoter can be transformed into BL21(DE3) competent cells (Novagen) and selected on 2×YT agar plates containing 50 µg/ml kanamycin. A colony arising from this transformation construct can be grown overnight at 30° C. in 2×YT media with 50 µg/mL kanamycin. The culture is then diluted two fold with fresh media, allowed to re-grow for 1 h, and induced by adding isopropyl-thiogalactopyranoside to 1 mM final concentration. Cells are then harvested by centrifugation after 3 h and re-suspended in 50 µL of 50 mM Tris-HCl at pH 8.0 containing 0.1 mM DTT and 0.2 mM phenyl methylsulfonyl fluoride. A small amount of 1 mm glass, beads can be added and the mixture sonicated 3 times for about 5 seconds each time with a microprobe sonicator. The mixture is centrifuged and the protein concentration of the supernatant determined. One µg of protein from the soluble fraction of the culture can be separated by SDS-polyacrylamide gel electrophoresis. Gels can be observed for protein bands migrating at the expected molecular weight.

Example 9

Conjugated 18:3 Fatty Acids can Improve Carcass Quality when added to Animal Feed Experiments were conducted to evaluate the effects of feeding eleostearic (18:3) conjugated fatty acids on pig growth, carcass characteristics, and fat firmness. Twenty-four pigs (barrows, castrated males, from PIC genetics) with a capacity for high rates of daily lean growth and reduced back fat were randomly assigned by litter mates, weight, and block to three dietary treatments. Group one was fed normal corn feed, group two received normal corn feed supplemented with CLA, and the third group received normal corn feed supplemented with conjugated linolenic acids, i.e., ClnAs (18:3 conjugated fatty acids). Pigs were penned individually and identified by ear tattoo. The average initial weight of the barrows was 125 pounds. Pigs were placed on their respective test diets at 150 lb, after being fed a common diet.

Diets were fed in two phases: Phase 1 (150 to 200 lb), and Phase 2 (200 to 250 lb). Ingredient and nutrient compositions of the treatment diets are shown in Table 4 and Table 5, respectively. The diets were formulated to be isocaloric.

TABLE 4

Ingredient Composition of Diets

| Ingredient, % | NC[1] | NC + CLA | NC + ClnA |
|---|---|---|---|
| Grower Diets | | | |
| NC[1] | 69.826 | 69.826 | 69.826 |
| Soybean Meal, 48%[2] | 25.283 | 25.283 | 25.283 |
| A-V Fat[3] | 2.498 | 2.498 | 2.498 |
| L-Lysine-HCl[4] | 0.073 | 0.073 | 0.073 |
| Limestone[5] | 0.838 | 0.838 | 0.838 |
| Dical 21[6] | 0.761 | 0.761 | 0.761 |
| Choline CH, 60%[7] | 0.096 | 0.096 | 0.096 |
| TM & Vitamin Premix[8] | 0.250 | 0.250 | 0.250 |
| Salt[9] | 0.300 | 0.300 | 0.300 |
| Copper Sulfate[10] | 0.075 | 0.075 | 0.075 |
| Finisher Diets | | | |
| NC | 75.142 | 75.142 | 75.142 |
| Soybean Meal, 48% | 20.340 | 20.340 | 20.340 |
| A-V Fat | 2.564 | 2.564 | 2.564 |
| Limestone | 0.740 | 0.740 | 0.740 |
| Dical 21 | 0.525 | 0.525 | 0.525 |
| Choline CH, 60% | 0.065 | 0.065 | 0.065 |
| TM & Vitamin Premix | 0.250 | 0.250 | 0.250 |
| Salt | 0.300 | 0.300 | 0.300 |
| Copper Sulfate | 0.075 | 0.075 | 0.075 |

[1]normal hybrid corn, W677, from Wyffels, Atkinson, IL
[2]Perdue Farms, Inc., Greenville, NC
[3]Moyer Packing Co., Souderton, PA
[4]Archer Daniels Midland Co., Decatur, IL
[5]Akey, Inc. Lewisburg, OH
[6]Potash Company of Saskatchewan, Davenport, IA
[7]Akey, Inc. Lewisburg, OH
[8]Trace Minerals and Vitamin Premix, Young's, Greensboro, MD
[9]Akey, Inc. Lewisburg, OH
[10]Akey, Inc. Lewisburg, OH

TABLE 5

Calculated nutrient composition of treatment diets.

| Nutrient | Phase 1 (150–200 lb) | Phase 2 (200–250 lb) |
|---|---|---|
| Energy, kcal/lb | 1734 | 1756 |
| Energy, kcal/kg | 3823 | 3871 |
| Protein, mcal % | 18.00 | 16.00 |

TABLE 5-continued

Calculated nutrient composition of treatment diets.

| Nutrient | Phase 1 (150–200 lb) | Phase 2 (200–250 lb) |
|---|---|---|
| Lysine, mcal % | 1.05 | 0.86 |
| Methionine + Cysteine, mcal % | 0.64 | 0.61 |
| Calcium, % | 0.60 | 0.50 |
| Total Phosphorus | 0.55 | 0.49 |

The mixer used to prepare the diets was flushed with 300 lb corn prior to mixing and between each mix to prevent cross-contamination. Conjugated linoleic acid (CLA) was purchased from Conlinco, Inc. (Detroit Lakes, Minn.) as "Clareen™". Conjugated linolenic acid (ClnA) was from a commercial source of tung oil (Industrial Oil Products, Woodbury, N.Y.) that was approximately 65% α-eleostearic acid. To achieve a final conjugated fatty acid concentration of 0.50%, 0.83 lb CLA preparation/100 lb diet and 0.73 lb CLnA preparation/100 lb of diet were added. To minimize oxidation of the conjugated fatty acid, diets were prepared each 14 days and refrigerated until use. Feed was added to feeders in minimal amounts daily. The antibiotic bacitracin methylene disalicylate (BMD, Alpharma, Inc., Fort Lee, N.J.) was included in all diets (50 g/ton). Feed samples were collected for amino acid and fatty acid analysis.

Live weights were recorded to determine average daily gains Phase 1 (150 to 200 lbs), and Phase 2 (200 to 250 lbs). Feed weight data were also collected to determine feed efficiency. Animals were observed 2–3 times daily for access to feeders and waterers, house temperatures, and any abnormal health conditions. Pigs were not replaced during the trial. Any animals that died were necropsied to determine the cause of death. Dead animal body weights were used to correct feed efficiency.

When pigs reached 250 pounds body weight they were slaughtered, processed and standard carcass measurements were collected. Because of limitations on conjugated fatty acid, pigs fed CLA and CLnA were fed a common diet four days prior to slaughter. Bellies from the eight pigs in each study group were evaluated for fat firmness evaluated by measuring belly thickness before and after compression. Fat compression was achieved by placing a 50 lb weight on the fresh belly for one hour. Fat compression was quantified by subtracting the compressed belly thickness from the initial belly thickness. Belly thickness was measured using a micrometer. The results of the belly compression evaluation are shown in Table 6. Data were analyzed as a randomized complete block design using the GLM (General Linear Model) procedure of SAS (Statistical Analysis Systems). Table values represent the difference between compressed and uncompressed pork belly thickness. A smaller number indicates reduced compression (i.e. greater firmness) of pork bellies. Because a pork belly is greater than 50% fat, the belly compression test is an indicator of relative firmness of pork belly fat. Addition of either CLA or ClnA to NC diets resulted in greater fat firmness in pigs. The improved pork fat firmness resulting from dietary addition of CLA is consistent with results reported by others (Eggert, J. M., et al. (1999) *J. Anim. Sci.* 77(*Suppl*):53; Thiel, R. C., et al. (1998) *J. Anim. Sci.* 76(*Supp*):13; Wiegand, B. R., F. C. Parrrish Jr and J. C. Sparks (1999) *J. Anim. Sci.* 77(*Suppl*):19; U.S. Pat. No. 5,554,646; and U.S. Pat. No. 5,851,572). Improved fat firmness resulting from dietary CLnA inclusion has not been previously reported. Based on the results of this experiment, addition of conjugated linoleic acid (CLA) or conjugated linolenic acid (ClnA) to pig diets results in improved fat firmness.

TABLE 6

Results of Fat Compression Test

| Measurement | NC | NC + CLA | NC + CLnA | SEM[1] |
|---|---|---|---|---|
| Pork Belly Compression, mm | 33.2[2] | 28.0 | 30.8 | 0.68 |

[1]Standard Error of the Mean
[2]All three test sample means were statistically different ($P < 0.05$)

Example 10

Production of Calendic Acid in Somatic Soybean Embryos

The *Calendula officinalis* clones CalFad2-1 and CalFad2-2 were expressed in somatic soybean embryos in order to examine their activity in a crop species.

The open-reading frames of these cDNAs were amplified by PCR in order generate the appropriate flanking restriction enzyme sites for cloning into the soybean expression vector. The oligonucleotide primers used for amplification of the CalFad2-1 open-reading frame were: 5'-ttgcggccgcTACACCTAGCTACGTACCATG-3' (sense, SEQ ID NO:18) and 5'-ttgcggccgTCACGGTACTGATGATGGCAC-3' (antisense, SEQ ID NO:19). The oligonucleotide primers used for amplification of the CalFad2-2 coding sequence were: 5'-agcggccgcTATACCATGGGCAAG-3' (sense, SEQ ID NO:20) and 5'-tgcggccgcTATGTTAAACTTC-3' (antisense, SEQ ID NO:21). [Note: The sequences shown in lower case contain an added NotI site along with additional bases to facilitate restriction enzyme digestion.] The template was the cDNA corresponding to either EST ecs1c.pk009.n14 (CalFad2-1) or EST ecs1c.pk008.a24 (CalFad2-2), and Pfu polymerase (Stratagene) was used for the amplification reactions. The resulting PCR products were subcloned into the intermediate vector pCR-Script AMP SK(+) (Stratagene) according to the manufacturer's protocol. The amplified CalFad2-1 and CalFad2-2 coding sequences were then released with NotI digestion and then subcloned into the corresponding site of the soybean expression vector pKS67.

Vector pKS67 contains the promoter of the gene for the α' subunit of β-conglycinin [Beachy et al., (1985) *EMBO J.* 4:3047–3053], which allows for strong seed-specific expression of transgenes. This vector was constructed as follows. A plasmid pZBL100 containing chimeric genes to allow expression of hygromycin B phosphotransferase in certain bacteria and in plant cells was constructed from the following genetic elements: a.) T7 promoter+Shine-Delgarno/hygromycin B phosphotransferase (HPT)/T7 terminator sequence, b.) 35S promoter from cauliflower mosaic virus (CaMV)/hygromycin B phosphotransferase (HPT)/nopaline synthase (NOS3' from Agrobacterium tumefaciens T-DNA, and c.) pSP72 plasmid vector (Promega) with β-lactamase coding region (ampicillin resistance gene) removed.

The hygromycin B phosphotransferase gene was amplified by PCR from *E. coli* strain W677 (Gritz, L. and Davies, J (1983) *Gene* 25:179–188 which contained a Klebsiella derived plasmid pJR225 (Gritz, L. and Davies, J (1983) *Gene* 25:179–188. Starting with the pSP72 vector (Promega) the elements were assembled into a single plasmid using standard cloning methods (Maniatis).

Plasmid pZBL100 thus contains the T7 promoter/HPT/T7 terminator cassette for expression of the HPT enzyme in certain strains of *E. coli*, such as NovaBlue (DE3) (Novagen), that are lysogenic for lambda DE3 (which carries the T7 RNA Polymerase gene under lacUV5 control). Plasmid pZBL100 also contains the 35S/HPT/NOS cassette for constitutive expression of the HPT enzyme in plants, such as soybean. These two expression systems allow selection for growth in the presence of hygromycin to be used as a means of identifying cells that contain the plasmid in both bacterial and plant systems.

PZBL100 also contains three unique restriction endonuclease sites suitable for the cloning of other chimeric genes into this vector.

The construction of a plasmid for expression of the CalFad2-1 and CalFad2-2 coding sequences under control of the soybean β-conglycinin α' subunit promoter (Beachy et al., (1985) *EMBO J.* 4:3047–3053) was facilitated by the use of plasmids pCW109 and pML18, both of which have been described (see World Patent Publication No. WO94/11516).

A unique NotI site was introduced into the cloning region between the β-conglycinin promoter and the phaseolin 3' end in pCW109 by digestion with NcoI and XbaI followed by removal of the single stranded DNA ends with mung bean exonuclease. NotI linkers (New England Biolabs) were ligated into the linearized plasmid to produce plasmid pAW35. The single NotI site in pML18 was destroyed by digestion with NotI, filling in the single stranded ends with dNTPs and Klenow fragment followed by re-ligation of the linearized plasmid. The modified pML18 was then digested with HindIII and treated with calf intestinal phosphatase.

The β-conglycinin:NotI:phaseolin expression cassette in pAW35 was removed by digestion with Hind III and the 1.8 kB fragment was isolated by agarose gel electrophoresis. The isolated fragment was ligated into the modified and linearized pML18 construction described above. A clone with the desired orientation was identified by digestion with NotI and XbaI to release a 1.08 kB fragment indicating that the orientation of the β-conglycinin transcription unit was the same as the selectable marker transcription unit. The resulting plasmid was given the name pBS19.

HindIII is one of the unique cloning sites available in pZBL100. To assemble the final expression cassette, pBS19 and pZBL100, were both digested with HindIII. The β-conglycinin containing fragment from pBS19 was isolated by gel electrophoresis and ligated into the digested pZBL100, which had been treated with calf alkaline phosphatase. The resulting plasmid was named pKS67.

The PCR amplified coding sequences of CalFad2-1 and CalFa2-2 were fused with the β-conglycinin promoter and phaseolin termination sequences in vector pKS67 was transformed into somatic soybean embryos as follows. To induce somatic embryos, cotyledons, 3–5 mm in length dissected from surface sterilized, immature seeds of a soybean cultivar A2872 or JACK-910 were cultured in the light or dark at 26° C. on an appropriate agar medium for 6–10 weeks. Somatic embryos that produce secondary embryos were then excised and placed into a suitable liquid medium. After repeated selection for clusters of somatic embryos that multiplied as early, globular staged embryos, the suspensions were maintained as described below.

Soybean embryogenic suspension cultures were maintained in 35 mL liquid media on a rotary shaker, 150 rpm, at 26° C. with florescent lights on a 16:8 hour day/night schedule. Cultures were subcultured every two weeks by inoculating approximately 35 mg of tissue into 35 mL of liquid medium.

Soybean embryogenic suspension cultures were then transformed with the vector pKS67 containing the coding sequence for CalFad2-1 and CalFad2-2 by the method of particle gun bombardment (Klein et al. (1987) *Nature* (London) 327:70, U.S. Pat. No. 4,945,050). A Du Pont Biolistica PDS1000/HE instrument (helium retrofit) was used for these transformations.

To 50 mL of a 60 mg/mL 1 mm gold particle suspension were added (in order): 5 mL DNA (1 mg/mL), 20 ml spermidine (0.1 M), and 50 mL $CaCl_2$ (2.5 M). The particle preparation was then agitated for three minutes, spun in a microfuge for 10 seconds and the supernatant removed. The DNA-coated particles were then washed once in 400 mL 70% ethanol and resuspended in 40 mL of anhydrous ethanol. The DNA/particle suspension was sonicated three times for one second each. Five mL of the DNA-coated gold particles was then loaded on each macro carrier disk.

Approximately 300–400 mg of a two-week-old suspension culture was placed in an empty 60×5-mm petri dish and the residual liquid removed from the tissue with a pipette. For each transformation experiment, approximately 5 to 10 plates of tissue were bombarded. Membrane rupture pressure was set at 1100 psi and the chamber was evacuated to a vacuum of 28 inches mercury. The tissue was placed approximately 3.5 inches away from the retaining screen and bombarded three times. Following bombardment, the tissue was divided in half and placed back into liquid and cultured as described above.

Five to seven days post bombardment, the liquid media was exchanged with fresh media, and eleven to twelve days post bombardment with fresh media containing 50 mg/mL hygromycin. This selective media was refreshed weekly. Seven to eight weeks post bombardment, green, transformed tissue was observed growing from untransformed, necrotic embryogenic clusters. Isolated green tissue was removed and inoculated into individual flasks to generate new, clonally propagated, transformed embryogenic suspension cultures. Each new line was treated as an independent transformation event. These suspensions were then subcultured and maintained as clusters of immature embryos. Immature embryos at this stage produce storage products, including storage lipids that are similar in composition to zygotic embryos at a similar stage of development (see World Patent Publication No. WO94/11516).

Figure 5:
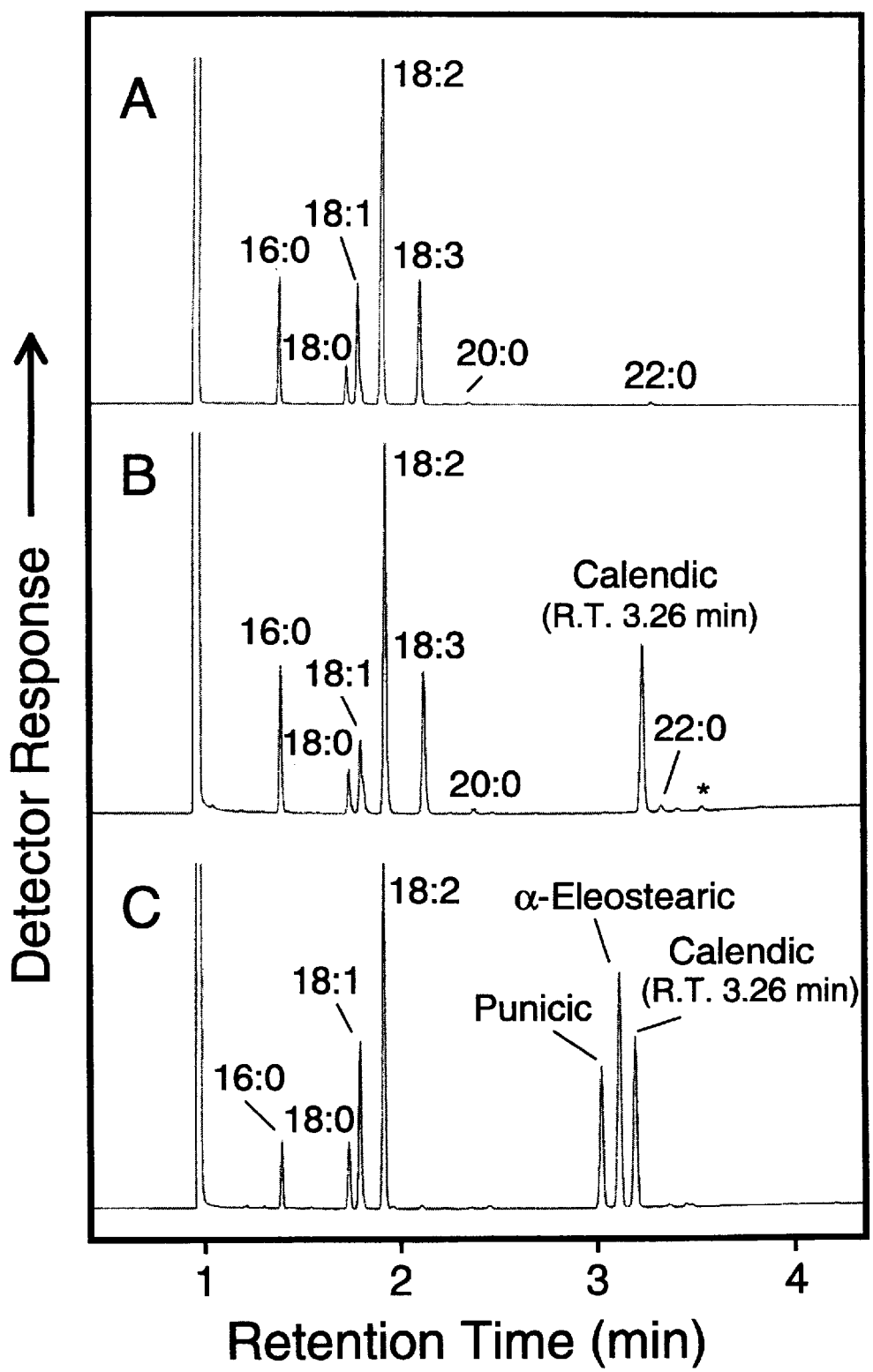
Figure 6:
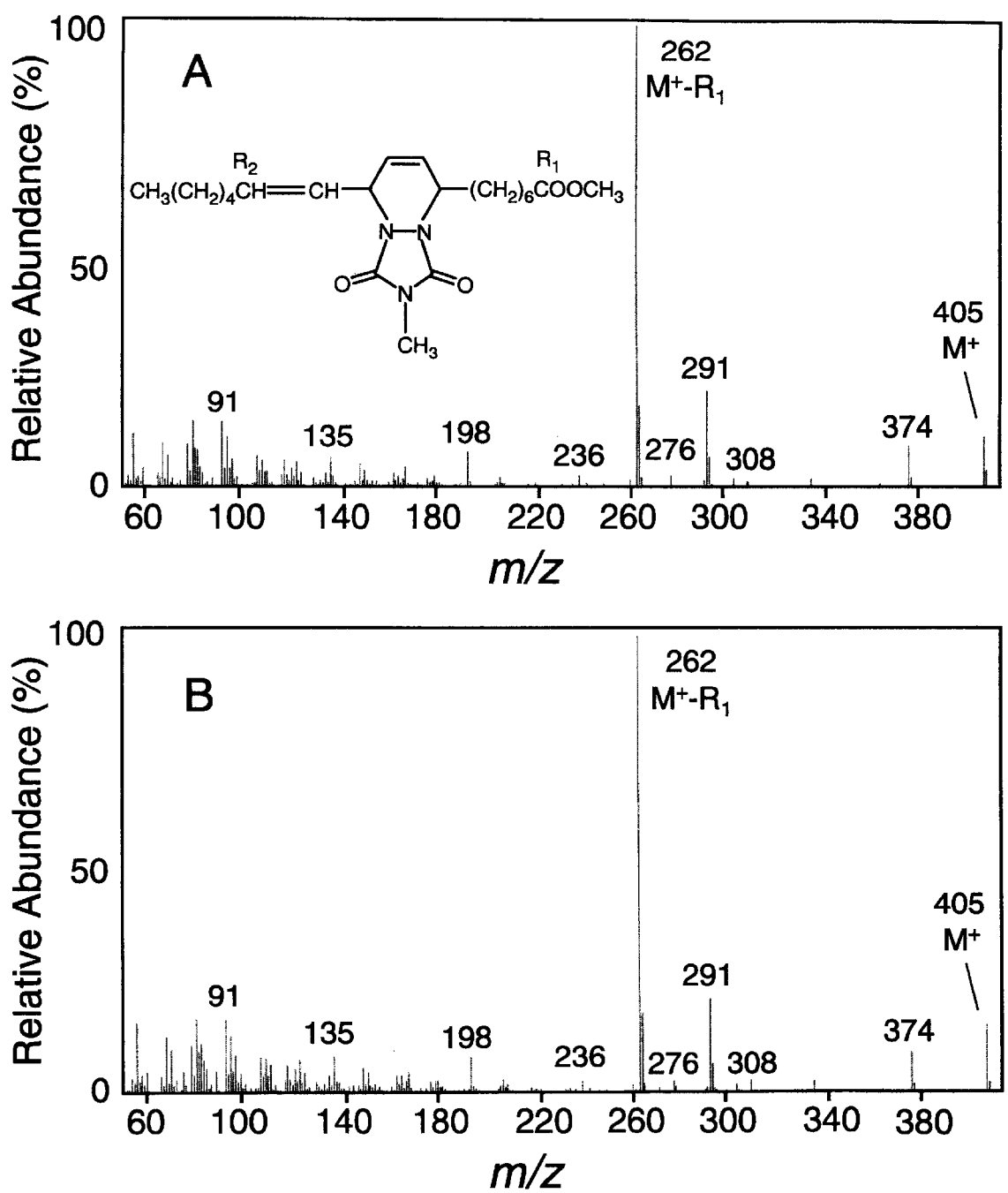

Transgenic soybean embryos selected and maintained in this manner were analyzed for calendic acid content using gas chromatography (GC) or gas chromatography-mass spectrometry (GC-MS). Individual embryos expressing either CalFad2-1 or CalFad2-2 were homogenized in 1% (w/v) sodium methoxide in methanol. Fatty acid methyl esters resulting from this transesterification step were analyzed by GC and GC-MS using methods described in Example 3. In somatic embryos expressing either cDNA, a fatty acid methyl ester with retention time and mass spectrum equivalent to that of methyl calendic acid from *Calendula officinalis* seed extracts was detected (FIG. 5). This fatty acid methyl ester was not detected in extracts from untransformed embryos. To further confirm the identity of methyl calendic acid in soybean embryos expressing CalFad2-1 and CalFad2-2, fatty acid methyl; esters from the transgenic tissue was reacted with 4-methyl-1,2,4-triazoline-3,5-dione (MTAD) [Dobson, G. (1998) *J. Am. Oil Chem. Soc.* 75:137–142] and the resulting derivatives were analyzed by GC-MS. (This reagent reacts primarily with conjugated trans-double bonds to form Diels-Alder adducts with MTAD.) A Hewlett-Packard 6890 GC linked to a Hewlett-Packard 5973 mass selective detector was used for these analyses. Samples were resolved with a DB1-Ht column (15 m×0.25 mm I.D.) (J&W Scientific), and the oven temperature was programmed from 185° C. (3-min hold) to 285° C. at a rate of 2° C./min. The mass spectrum of the MTAD derivative of the novel fatty acid methyl ester in the transgenic soybean embryos expressing CalFad2-1 and CalFad2-2 was identical to that of the MTAD derivative of methyl calendic acid from *Calendula officinalis* seed extracts (FIG. 6). These mass spectra were characterized by a molecular ion of 405 m/z and also by a major diagnostic ion of 262 m/z. These results thus confirm that somatic soybean embryos expressing either CalFad2-1 or CalFad2-2 produce calendic acid.

Table 7 shows a comparison of the fatty acid compositions of untransformed somatic soybean embryos and embryos from transgenic lines MSE 284-2-6 and MSP 425-12-2 that are transformed with the CalFad2-1 and CalFad2-2 cDNAs, respectively, behind the seed-specific β-conglycinin α' subunit promoter (as described above).

TABLE 7

Somatic Embryo Fatty Acid Compositions From Soybean Transgenic Lines MSE 284-2-6 and MSP 425-12-2 Expressing the CalFad2-1 and CalFad2-2 cDNAs Associated with Calendic Acid Synthesis

| Fatty Acid Weight %[1]: | Untransformed (n = 5)[2] | MSE 284-2-6 (CalFad2-1) (n = 5) | MSP 425-12-2 (CalFad2-2) (n = 5) |
|---|---|---|---|
| 16:0 | 14.2 ± 0.8 | 12.2 ± 1.0 | 12.3 ± 1.1 |
| 18:0 | 2.9 ± 0.4 | 3.5 ± 0.9 | 3.3 ± 0.5 |
| 18:1 | 7.2 ± 1.0 | 9.0 ± 1.5 | 8.6 ± 2.1 |
| 18:2 | 53.5 ± 3.2 | 52.2 ± 2.4 | 38.2 ± 3.4 |
| 18:3 | 20.6 ± 2.5 | 18.8 ± 3.0 | 17.7 ± 3.5 |
| Calendic Acid | N.D.[3] | 3.1 ± 1.0 | 18.1 ± 3.6 |
| Other | ≦1.6 | ≦1.3 | ≦1.7 |

[1]The fatty acid compositions are given as the weight percentage of total fatty acids of somatic soybean embryos measured by gas chromatography as described above.
[2]Values were obtained from five separate measurements (± standard deviation) of single embryos
[3]N.D., Not detected.

Example 11

Production of Dimorphecolic Acid in Transgenic Somatic Soybean Embryos

The seed oil of Dimorphotheca species including *Dimorphotheca sinuata* is enriched in the unusual $C_{18}$ fatty acid dimorphecolic acid (9-OH-18:2$\Delta^{10trans,\ 12trans}$), which contains two conjugated trans-double bonds between the $\Delta^{10}$ and $\Delta^{11}$ and between the $\Delta^{12}$ and $\Delta^{13}$ carbon atoms as well as a hydroxyl group on the $\Delta^9$ carbon atom [Binder, R. G. et al., (1964) *J. Am. Oil Chem. Soc.* 41:108–111; Morris, L. J. et al., (1960) *J. Am. Oil Chem. Soc.* 37:323–327]. From the results described below, it is believed that dimorphecolic acid is produced in a biosynthetic pathway involving the activities of two diverged forms of the $\Delta^{12}$-oleic acid desaturase (Fad2) from Dimorphotheca, designated DMFad2-1 and DMFad2-2 (FIG. 7). Expression data from transgenic somatic soybean embryos (as described below) is consistent with DMFad2-1 catalyzing the formation of a $\Delta^{12trans}$ double-bond in oleic acid to form 18:2$\Delta^{9cis,\ 12trans}$. The $\Delta^{9cis}$ double bond of this fatty acid intermediate is then modified by DMFad2-2 to form 9-OH and a $\Delta^{10trans}$ double bond. Therefore, the hydroxylation of the $\Delta^9$-position by DMFad2-2 leads to the formation of conjugated double-bonds. The product of these two steps is dimorphecolic acid.

The cDNAs for DMFad2-1 and DMFad2-2 were derived from ESTs for diverged Fad2s that were identified among pools of ESTs from a *Dimorphotheca sinuata* seed cDNA library (dms2c.pk006.d7, SEQ ID NO:10; and dms2c.pk001.I13, SEQ ID NO:12). It is notable that the amino acid sequence corresponding to DMFad2-2 (SEQ ID NO:13) is most related to those of CalFad2-1 (SEQ ID NO:2) and CalFad2-2 (SEQ ID NO: 4), which have been demonstrated to catalyze the formation of conjugated double bonds by modification of the delta-9 position of linoleic acid (Examples 3, 4, and 10). Using the multiple sequence comparison program Megalign (v3.1.7) from the Lasergene□ software package (DNASTAR Inc., Madison, WI) and the Clustal method of alignment (default program parameters), the amino acid sequence of DMFad2-2 (SEQ ID NO:13) shares 72.5% identity with the amino acid sequence of CalFad2-1 (SEQ ID NO:2) and 74.0% identity with the amino acid sequence of CalFad2-2 (SEQ ID NO:4). In contrast, the amino acid sequence of DMFad2-2 (SEQ ID NO: 3) shares less than 52% identity with any of the other Fad2-related polypeptides shown in FIGS. 2A–2D including those of the castor hydroxylase and conventional $\omega^6$-oleic acid desaturases like the soybean, borage, and sunflower polypeptides. Therefore, given its close relation to CalFad2-1 and CalFad2-2, it is believed that DMFad2-2 is associated with the modified delta-9 position that is present in dimorphecolic acid. It is also notable that the residue immediately adjacent to the first histidine box in the amino acid sequences of DMFad2-1 and DMFad2-2 is a glycine (as indicated by an asterisk in FIGS. 2A–2D). A glycine in this position is only observed in $\omega^6$-oleic acid desaturase-related enzymes that have diverged functionality, such as the castor oleic acid hydroxylase (van de Loo, F. J. et al. (1995) *Proc. Natl. Acad. Sci. U.S.A.* 92:6743–6747) and the *Crepis palaestina* epoxidase (Lee, M. et al. (1998) *Science* 280:915–918). Given this feature of their primary structures, it is believed that the polypeptides encoded by DMFad2-1 and DMFad2-2 are associated with dimorphecolic acid synthesis and are not conventional $\omega^6$-oleic acid desaturases involved in standard fatty acid synthesis.

Initially, the open-reading frames of cDNAs for DMFad2-1 and DMFad2-2 were amplified by PCR using Pfu polymerase (Stratagene) to generate the appropriate restriction enzyme sites for cloning into the soybean expression vector. For amplification of the open-reading frame of the DMFad2-1 cDNA, EST dms2c.pk006.d7 (SEQ ID NO:10 for the nucleotide sequence, and SEQ ID NO:11 for the polypeptide translation product) was used as the template, and the oligonucleotide primers were: 5'-tatgcggccgcAAATGGGAGCAGGAGGTTG-3' (sense, SEQ ID NO:22) and 5'-tttgcggccgcATTACATCTTATTCTTGTACC-3' (antisense, SEQ ID NO:23). For amplification of the open-reading frame of the DMFad2-2 cDNA, EST dms2c.pk001.I13 (SEQ ID NO:12 for the nucleotide sequence, and SEQ ID NO:13 for the polypeptide translation product) was used as the template, and the oligonucleotide primers were: 5'-tgcggccgcAATGGGTGGAGGGATGGGAGCATCT GAG-3' (sense, SEQ ID NO:24) and 5'-tagcggccgcTGATTAATCAAGTCTTAG-3' (antisense, SEQ ID NO:25). The nucleotides shown in lower case are not Dimorphotheca sequences, but instead encode an added NotI site along with additional bases to facilitate restriction enzyme digestion. The resulting PCR products were subcloned into the intermediate vector pCR-Script AMP SK(+) (Stratagene) according to the manufacturer's protocol. The DMFad2-1 and DMFad2-2 PCR products were then moved as NotI fragments into corresponding site of the soybean expression vector pKS67 behind the promoter of the gene for the α' subunit of β-conglycinin. The construction of vector pKS67 is described in Example 10. The DMFad2-1 NotI fragment was also subcloned into the soybean expression vector pKS17, which is equivalent to vector pKS67 except that it lacks the 35S/hygromycin phosphotransferase (HPT)INOS cassette for constitutive expression of the HPT enzyme in plants.

The expression constructs containing the DMFad2-1 and DMFad2-2 coding sequences in vector pKS67 were transformed into somatic soybean embryos using the biolistic method as described in Example 10. To determine their functions, DMFad2-1 and DMFad2-2 were expressed individually or co-expressed in somatic soybean embryos. The fatty acid compositions of the resulting transgenic soybean embryos were then assessed for the presence of novel fatty acid structures. The individual transformation experiments were MSE331 (DMFad2-1) and MSE229 (DMFad2-2). The co-expression transformation experiment (MSE 330) was conducted in which the DMFad2-2 coding sequence in vector pKS67 was co-transformed with the DMFad2-1 coding sequence in vector pKS17 in somatic soybean embryos, using a molar ratio of 1:10 of the two expression constructs for the transformation (using methods described in Example 10). The resulting transgenic soybean embryos selected for hygromycin resistance were analyzed for alterations in fatty acid content relative to untransformed embryos. Fatty acid methyl esters were prepared by homogenization of untransformed and transgenic somatic soybean embryos in 1% (w/v) sodium methoxide in methanol using methods described by Hitz et al. (1994) *Plant Physiol.* 105:635–641. Fatty acid methyl esters were dried under nitrogen and reacted with 50–100 µl of the silylating reagent bis (trimethylsilyl)trifluoroacetamide:trimethylchlorosilane (99:1 v/v) (Supelco) in order to convert the hydroxyl group of dimorphecolic acid to a trimethylsilyl (TMS) ether derivative for gas chromatography (GC) and gas chromatography-mass spectrometry (GC-MS) analysis. The recovered fatty acid methyl esters and derivatives were then analyzed using a Hewlett-Packard 6890 chromatograph fitted with an Omegawax 320 column (30 m×0.32 mm inner diameter; Supelco). The oven temperature was programmed from 185° C. (4 min hold) to 215° C. at a rate of 5° C./min and then to 240° C. at 20° C./min (1 min hold). Fatty acid methyl esters were also analyzed by GC-MS an HP6890 interfaced with a HP5973 (Hewlett-Packard) mass selective detector. Compounds were resolved using an HP-INNOWax column (30 m×0.25 mm inner diameter) with the oven temperature programmed from 180° C. (3.5-min hold) to 215° C. at a rate of 2° C./min (2-min hold) and then to 230° C. at 10° C./min.

GC analysis of fatty acid methyl esters from transgenic soybean embryos expressing DMFad2-1 (transformation experiment MSE 331) indicated the presence of a peak that eluted immediately after methyl linoleic acid ($18:2\Delta^{9cis,\ 12cis}$) (FIG. 8), but was absent from untransformed embryos. This peak had the same retention time and mass spectrum as the methyl ester of $18:2\Delta^{9cis,\ 12trans}$ that is found in the developing *Dimorphotheca sinuata* seeds. The novel fatty acid resulting from DMFad2-1 expression in transgenic soybean embryos is thus identified as $18:2\Delta^{9cis,\ 12trans}$. Amounts of this fatty acid measured in single soybean embryos from experiment MSE 331 ranged from 0 to 21 wt % of the total fatty acids. Based on these results, DMFad2-1 was identified as a fatty acid modifying enzyme associated with the synthesis of the trans-$\Delta^{12}$ double bond of $18:2\Delta^{9cis,\ 12trans}$.

Fatty acid methyl esters from transgenic soybean embryos expressing DMFad2-2 (transformation experiment MSE 229) were analyzed by GC-MS using a selected ion scan for ion 225 m/z, which is the most abundant ion in the mass spectrum of the TMS derivative of methyl dimorphecolic acid. In these selected ion chromatograms, two peaks were detected that displayed mass spectra equivalent to that of the TMS derivative of methyl dimorphecolic acid. The less abundant of these peaks had the same retention time as that of the TMS derivative of methyl dimorphecolic acid from *Dimorphotheca sinuata* seeds. However, the larger of the two peaks displayed a shorter retention time and is tentatively identified as the cis-$\Delta^{12}$ isomeric form of dimorphecolic acid (9-OH-$18:2\Delta^{9cis,\ 12cis}$), which has previously been reported to occur in trace amounts in the seed oil of Dimorphotheca species [Morris, L. J., et al., (1960) *J. Am. Oil Chem. Soc.* 37:323–327]. This isomeric form of dimorphecolic acid likely arises from the modification of the $\Delta^9$ double bond of linoleic acid ($18:2\Delta^{9cis,\ 12cis}$) by DMFad2-2. The dimorphecolic acid isomers detected in soybean embryos expressing DMFad2-2 accounted for <0.1% of the total fatty acids.

Figure 9:
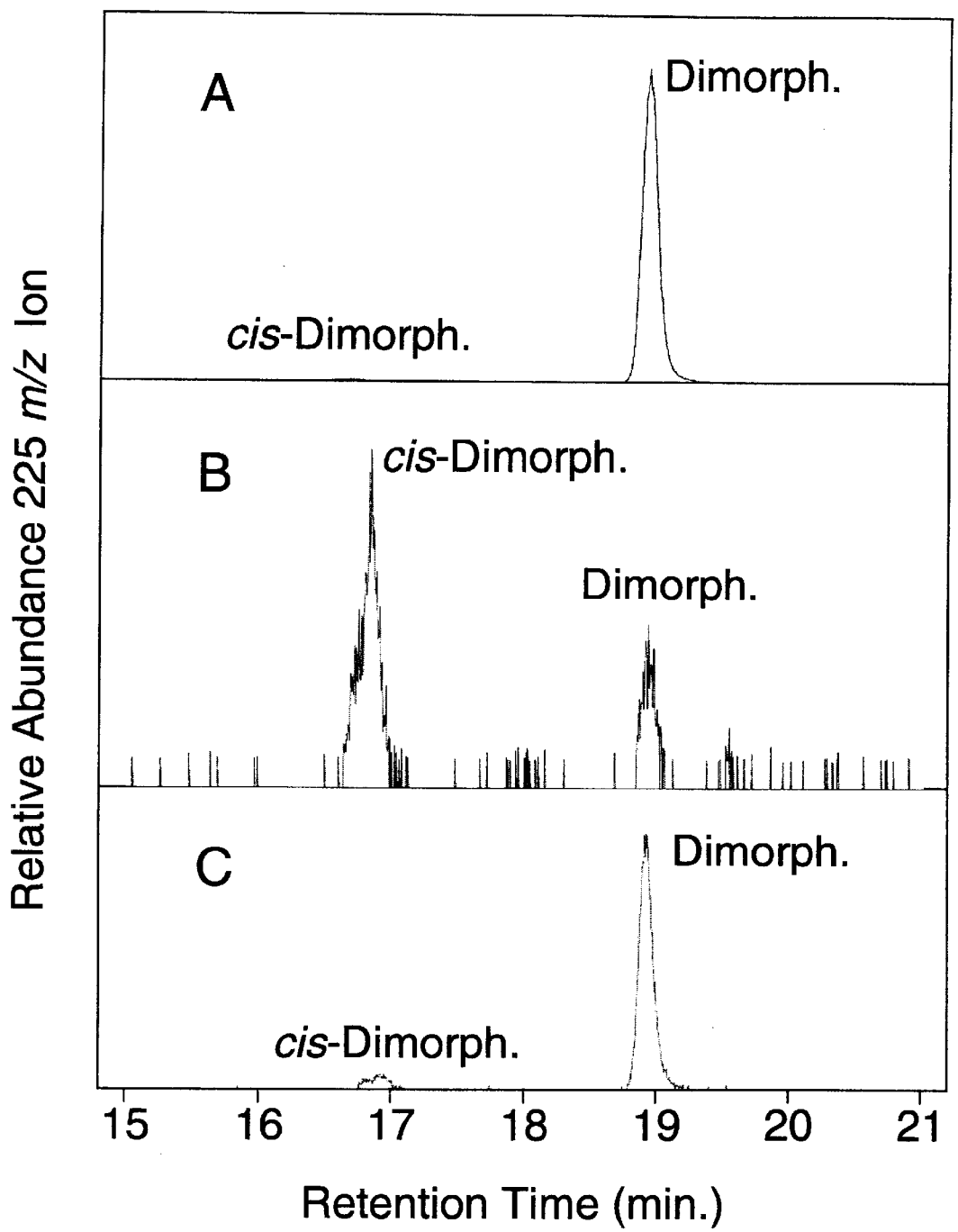
Figure 10:
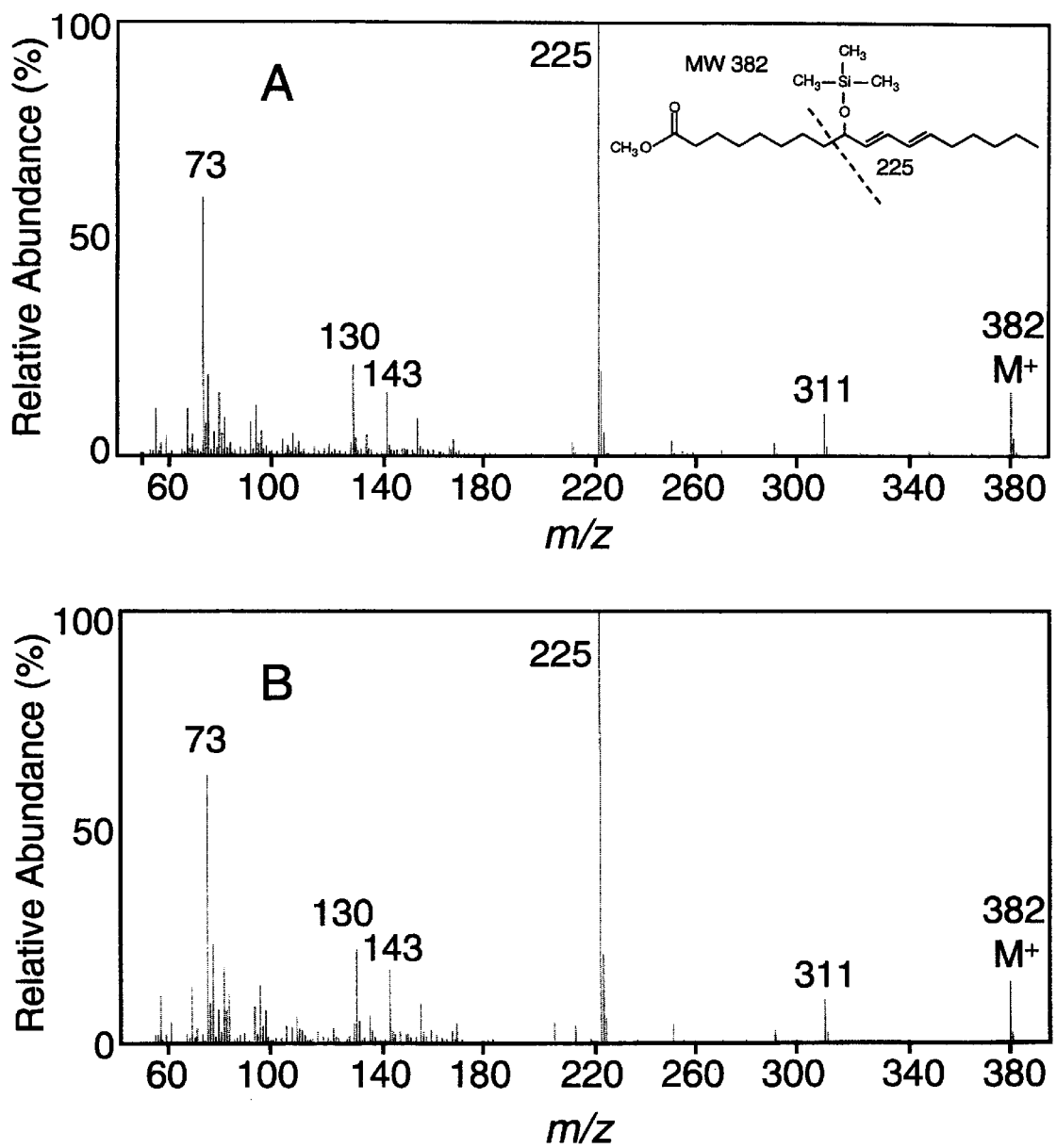

Results from expression of DMFad2-2 alone suggested that a limiting factor in the synthesis of dimorphecolic acid is the lack of a significant substrate pool of the trans-$\Delta^{12}$ isomer of linoleic acid ($18:2\Delta^{9cis,\ 12trans}$) in somatic soybean embryos. As described above, this fatty acid is the product of DMFad2-1. Therefore, in an attempt to increase amounts of dimorphecolic acid in transgenic embryos, DMFad2-1 and DMFad2-2 were co-expressed in somatic soybean embryos (transformation experiment MSE 330). The resulting embryos accumulated both $18:2\Delta^{9cis,\ 12trans}$ and the predominant form of dimorphecolic acid (9-OH-$18:2\Delta^{9cis,\ 12trans}$) which are also found in the seed oil of *Dimorphotheca sinuata* (FIG. 9 and 10). In these embryos, dimorphecolic acid accounted for 0.5 to 1 wt % of the total fatty acids compared to accumulations of less than 0.1% in "DMFad2-2 alone" transformants. In addition, the primary form of dimorphecolic acid detected in the "DMFad2-2 alone" transformations was the tentatively identified as the $\Delta^{12cis}$ isomer of dimorphecolic acid (9-OH-$18:2\Delta^{9cis,\ 12cis}$, see FIGS. 7 and 9). These results are thus consistent with a biosynthetic pathway for dimorphecolic acid involving the initial activity of DMFad2-1 that generates $18:2\Delta^{9cis,\ 12trans}$. The $\Delta^9$ double bond of this fatty acid is then modified to a 9-hydroxy and $\Delta^{10trans}$ double bond by DMFad2-2 to yield dimorphecolic acid (FIG. 7).

Example 12

Characterization of the Trans-Linoleic Product of DMFad2-1

To further characterize the structure of the putative $18:2\times^{9cis,\ 12trans}$ isomer from soybean embryos expressing DMFad2-1, the methyl ester of this fatty acid is purified to near homogeneity from the transgenic embryos and analyzed by $^1$H-$^{13}$C NMR two-dimensional correlation NMR. The methyl ester of the putative $18:2\Delta^{9cis,\ 12trans}$ is purified from extracts of transgenic soybean embryos using a combination of reverse-phase and argentation thin layer chromatography (TLC). Fatty acid methyl esters from soybean embryos expressing DMFad2-1 are initially resolved by reverse phase TLC using a solvent system of methanol:acetonitrile:water (60:40:1 v/v/v) and 20 cm×20 cm RP18 TLC plates (Merck). TLC plates containing the crude fatty acid methyl esters are developed sequentially to 10-cm, 15-cm and finally to the full-length of the plate. TLC plates are dried under nitrogen between developments. A band containing a mixture of methyl 18:2Δ$^{9cis, 12cis}$ and putative 18:2Δ$^{9cis, 12trans}$ is identified by light staining with iodine vapor and then recovered from the scraped TLC matrix using hexane:isopropanol (7:2 v/v). These two isomers are then resolved using argentation TLC with 10-cm×20-cm silica gel K60 plates (Whatman) that are saturated with a solution of 5% (w/v) silver nitrate in acetonitrile. The methyl 18:2Δ$^{9cis, 12cis}$ and putative 18:2Δ$^{9cis, 12trans}$ isomers are then separated on the argentation plates using a solvent system of hexane:ethyl ether (80:20 v/v) and sequential developments as described above. The putative methyl 18:2Δ$^{9cis, 12trans}$ isomer, which displays a higher mobility than methyl 18:2Δ$^{9cis, 12cis}$, is identified by ultraviolet absorbance after spraying the plate with 0.1% (w/v) 2,7-dichlorofluorescein in methanol. The putative methyl 18:2Δ$^{9cis, 12trans}$ isomer is then recovered from the scraped TLC matrix with hexane:ethyl ether (50:50 v/v), and residual dichlorofluorescein is removed by washing the organic layer with 1 M Tris (pH9.0). The sample is finally passed over a silica column and eluted with, hexane:ethyl ether (80:20 v/v) to remove any impurities.

The purified putative methyl 18:2Δ$^{9cis, 12trans}$ isomer derived from the transgenic soybean embryos is then analyzed by $^1$H-$^{13}$C two-dimensional correlation NMR. The spectrum shows vinyl proton (protons associated with carbon double-bonds) chemical shifts that differ when the protons are in the cis versus trans orientation. For instance, vinyl proton chemical shifts from a methyl 18:2Δ$^{9cis, 12cis}$ standard are 5.396, 5.380, 5.348, and 5.340 ppm (one reading for each proton in the two double bonds), compared to a methyl 18:2Δ$^{9trans, 12trans}$ standard that has chemical shifts of 5.400, 5.392, 5.434, and 5.434 ppm. The fatty acids from transgenic soybean are analyzed in a comparable experiment and compared to the known methyl 18:2Δ$^{9cis, 12trans}$ isomer isolated form Dimorphotheca seed oil (Morris, et al., (1960) *J. Am. Oil Chem. Soc.* 37:323–327; Morris and Marshall (1966) *Chem & Ind* 1493–1494).

What is claimed is:

1. A chimeric gene comprising an isolated nucleic acid fragment encoding a plant fatty acid modifying enzyme associated with conjugated double bond formation comprising a delta-9 position of fatty acids having an amino acid identity of at least 72.5% based on the Clustal method of alignment when compared to a polypeptide of SEQ ID NO:2 or 4 wherein said fragment or a functionally equivalent subfragment thereof or a complement thereof is operably linked to suitable regulatory sequences.

2. The chimeric gene of claim 1 wherein the nucleic acid fragment is isolated from *Calendula officinalis*.

3. The chimeric gene of claim 1 wherein the plant fatty acid modifying enzyme is associated with the formation of calendic acid.

4. A transformed host cell or plant comprising in its genome the chimeric gene of claim 1.

5. A transformed host cell or plant comprising in its genome the chimeric gene of claim 2.

6. A transformed host cell or plant comprising in its genome the chimeric gene of claim 3.

7. A method of altering the level of fatty acids in a host cell or plant wherein said fatty acids comprise a modification at a delta-9 position, said method comprising:
(a) transforming a host cell or plant with the chimeric gene of claim 1;
(b) growing the transformed host cell or plant under conditions suitable for the expression of the chimeric gene; and
(c) selecting those transformed host cells or plants having altered levels of fatty acids comprising a modified delta-9 position.

8. A method of altering the level of fatty acids in a host cell or plant wherein said fatty acids comprise a modification at a delta-9 position, said method comprising:
(a) transforming a host cell or plant with the chimeric gene of claim 2;
(b) growing the transformed host cell or plant under conditions suitable for the expression of the chimeric gene; and
(c) selecting those transformed host cells or plants having altered levels of fatty acids comprising a modified delta-9 position.

9. A method of altering the level of fatty acids in a host cell or plant wherein said fatty acids comprise a modification at a delta-9 position, said method comprising:
(a) transforming a host cell or plant with the chimeric gene of claim 3;
(b) growing the transformed host cell or plant under conditions suitable for the expression of the chimeric gene; and (c) selecting those transformed host cells or plants having altered levels of fatty acids comprising a modified delta-9 position.

10. The method of claim 7, 8, or 9 wherein the host cell or plant is selected from the group consisting of plant cells and microorganisms.

11. The method of claim 7, 8, or 9 and wherein the level of calendic acid is altered.

12. A method for producing fatty acid modifying enzymes associated with modification of a delta-9 position of fatty acids which comprises:
   (a) transforming a microbial host cell with the chimeric gene of claim 1;
   (b) growing the transformed host cell under conditions suitable for the expression of the chimeric gene; and
   (c) selecting those transformed host cells containing altered levels of protein encoded by the chimeric gene.

13. A method for producing fatty acid modifying enzymes associated with modification of a delta-9 position of fatty acids which comprises:
   (a) transforming a microbial host cell with the chimeric gene of claim 2;
   (b) growing the transformed host cell under conditions suitable for the expression of the chimeric gene; and
   (c) selecting those transformed host cells containing altered levels of protein encoded by the chimeric gene.

14. A method for producing fatty acid modifying enzymes associated with modification of a delta-9 position of fatty acids which comprises:
   (a) transforming a microbial host cell with the chimeric gene of claim 3;
   (b) growing the transformed host cell under conditions suitable for the expression of the chimeric gene; and
   (c) selecting those transformed host cells containing altered levels of protein encoded by the chimeric gene.

15. The method of claim 12, 13, or 14 wherein the fatty acid modifying enzyme is associated with the formation of calendic acid or dimorphecolic acid.

* * * * *

SEQUENCE LISTING

<160> NUMBER OF SEQ ID NOS: 25

<210> SEQ ID NO 1
<211> LENGTH: 1457
<212> TYPE: DNA
<213> ORGANISM: Calendula officinalis
<220> FEATURE:
<221> NAME/KEY: CDS
<222> LOCATION: (31)..(1152)

<400> SEQUENCE: 1

```
aaaccactat actacaccta gctacgtacc atg ggc aaa gga gca tca aac aag      54
                                 Met Gly Lys Gly Ala Ser Asn Lys
                                  1               5 aag gtt ttg gaa cga gtt cca atc aca aaa ccg cca ttc gaa tac aat     102
Lys Val Leu Glu Arg Val Pro Ile Thr Lys Pro Pro Phe Glu Tyr Asn
             10                  15                  20 gat ctg aag aaa gca gta cca cca cat tgt ttt tca cga cca ctt ttc     150
Asp Leu Lys Lys Ala Val Pro Pro His Cys Phe Ser Arg Pro Leu Phe
 25                  30                  35                  40 cgt tcg ttt tat ttc cta ctt cac gac att att gta aca tgt atc ctt     198
Arg Ser Phe Tyr Phe Leu Leu His Asp Ile Ile Val Thr Cys Ile Leu
                 45                  50                  55 ttc tac gta gca tca aac tac att cct atg ctc cct ggt ttc ctt tcc     246
Phe Tyr Val Ala Ser Asn Tyr Ile Pro Met Leu Pro Gly Phe Leu Ser
             60                  65                  70 tac att gta tgg cct gtt tac tgg atc tcc caa gga gtt ttt ctt ggc     294
Tyr Ile Val Trp Pro Val Tyr Trp Ile Ser Gln Gly Val Phe Leu Gly
         75                  80                  85 aga ttg tgg atg att ggc cat gaa tgc ggc cat cat agt ttt agt aat     342
Arg Leu Trp Met Ile Gly His Glu Cys Gly His His Ser Phe Ser Asn
     90                  95                 100 tac cgt tgg gtc gac gat agt gtt ggt ttt tta atc cat acg gcc acc     390
Tyr Arg Trp Val Asp Asp Ser Val Gly Phe Leu Ile His Thr Ala Thr
105                 110                 115                 120 ctc act ccc tat ttt tcc ttc aaa tat agt cac cgt aat cac cat gca     438
Leu Thr Pro Tyr Phe Ser Phe Lys Tyr Ser His Arg Asn His His Ala
                125                 130                 135 cac acc aat tcc atg gaa tat gac gaa gtt cat atc ccg aaa cgc aaa     486
His Thr Asn Ser Met Glu Tyr Asp Glu Val His Ile Pro Lys Arg Lys
            140                 145                 150
```

```
tcc gaa gct cta gat ctc tac ttt gaa ttt ctc ggc aac aac ccg atg      534
Ser Glu Ala Leu Asp Leu Tyr Phe Glu Phe Leu Gly Asn Asn Pro Met
            155                 160                 165 ggg tta atg atc acc atg tta tgt aaa ctc act ttt gga tat gca gct      582
Gly Leu Met Ile Thr Met Leu Cys Lys Leu Thr Phe Gly Tyr Ala Ala
        170                 175                 180 tac att atg ttc aat tat aca ggc aag aag cac aaa tct ggg ggt tta      630
Tyr Ile Met Phe Asn Tyr Thr Gly Lys Lys His Lys Ser Gly Gly Leu
185                 190                 195                 200 gca agt cac ttc tac cca caa agc cct ctc ttt aac gac agc gaa cgt      678
Ala Ser His Phe Tyr Pro Gln Ser Pro Leu Phe Asn Asp Ser Glu Arg
            205                 210                 215 aat cat gtt ttg ttc tct gat gtc ggg att tgc atc gtc ttg tac gca      726
Asn His Val Leu Phe Ser Asp Val Gly Ile Cys Ile Val Leu Tyr Ala
        220                 225                 230 tgt tac cgt att gtg atg gtc aca ggg gca atg tcg gca ttt tat gtg      774
Cys Tyr Arg Ile Val Met Val Thr Gly Ala Met Ser Ala Phe Tyr Val
    235                 240                 245 tac ggc att cct tgg gtt ata atg agt gct att ctc ttt gca gca act      822
Tyr Gly Ile Pro Trp Val Ile Met Ser Ala Ile Leu Phe Ala Ala Thr
        250                 255                 260 tat tta caa cac act cat cct tcg atc cct cat tat gat aca act gag      870
Tyr Leu Gln His Thr His Pro Ser Ile Pro His Tyr Asp Thr Thr Glu
265                 270                 275                 280 tgg aac tgg ctt aga ggg gca tta tcg aca att gat aga gat tta ggg      918
Trp Asn Trp Leu Arg Gly Ala Leu Ser Thr Ile Asp Arg Asp Leu Gly
            285                 290                 295 ttc ttc aac atg aac aaa aca cat tat cat gtt atc cac cat tta ttt      966
Phe Phe Asn Met Asn Lys Thr His Tyr His Val Ile His His Leu Phe
        300                 305                 310 cct gtc att ccg gaa tac cat gca caa gag gca act gag gcc atc aag     1014
Pro Val Ile Pro Glu Tyr His Ala Gln Glu Ala Thr Glu Ala Ile Lys
    315                 320                 325 ccc atc tta ggt caa tat tac aag tat gat ggt act ccg ttt tta aag     1062
Pro Ile Leu Gly Gln Tyr Tyr Lys Tyr Asp Gly Thr Pro Phe Leu Lys
        330                 335                 340 gcg ttg tgg aga gaa atg aag gac tgt att tat gta gaa tcc gat caa     1110
Ala Leu Trp Arg Glu Met Lys Asp Cys Ile Tyr Val Glu Ser Asp Gln
345                 350                 355                 360 ggt cag aag aaa caa ggt att tac tgg ttc aag aat aag att              1152
Gly Gln Lys Lys Gln Gly Ile Tyr Trp Phe Lys Asn Lys Ile
            365                 370 tgaagtttca aataatctgg actacgttta attttgtgcc atcatcagta ccgtgaatta    1212
gttttgttgt ggagagaaat gaaggactgt atttatgtag aatccgatca aggtcagaag    1272
aaacaaggta tttactggtt caagaataag atttgaagtt tcaaataatc tggactacgt    1332
ttaattttgt gccatcatca gtaccgtgaa ttagttttgt tgtgttttta attttaattt    1392
cgtgtgatgg tgtaatgtaa tataattcag tataataaag gcgttatcct ttcatgggtt    1452
taaaa                                                               1457
```

<210> SEQ ID NO 2
<211> LENGTH: 374
<212> TYPE: PRT
<213> ORGANISM: Calendula officinalis

<400> SEQUENCE: 2

```
Met Gly Lys Gly Ala Ser Asn Lys Lys Val Leu Glu Arg Val Pro Ile
  1               5                  10                  15
```

-continued

Thr Lys Pro Pro Phe Glu Tyr Asn Asp Leu Lys Lys Ala Val Pro Pro
            20                  25                  30

His Cys Phe Ser Arg Pro Leu Phe Arg Ser Tyr Phe Leu Leu His
        35                  40                  45

Asp Ile Ile Val Thr Cys Ile Leu Phe Tyr Val Ala Ser Asn Tyr Ile
        50                  55                  60

Pro Met Leu Pro Gly Phe Leu Ser Tyr Ile Val Trp Pro Val Tyr Trp
65                  70                  75                  80

Ile Ser Gln Gly Val Phe Leu Gly Arg Leu Trp Met Ile Gly His Glu
                85                  90                  95

Cys Gly His His Ser Phe Ser Asn Tyr Arg Trp Val Asp Asp Ser Val
            100                 105                 110

Gly Phe Leu Ile His Thr Ala Thr Leu Thr Pro Tyr Phe Ser Phe Lys
        115                 120                 125

Tyr Ser His Arg Asn His Ala His Thr Asn Ser Met Glu Tyr Asp
        130                 135                 140

Glu Val His Ile Pro Lys Arg Lys Ser Glu Ala Leu Asp Leu Tyr Phe
145                 150                 155                 160

Glu Phe Leu Gly Asn Asn Pro Met Gly Leu Met Ile Thr Met Leu Cys
                165                 170                 175

Lys Leu Thr Phe Gly Tyr Ala Ala Tyr Ile Met Phe Asn Tyr Thr Gly
            180                 185                 190

Lys Lys His Lys Ser Gly Gly Leu Ala Ser His Phe Tyr Pro Gln Ser
        195                 200                 205

Pro Leu Phe Asn Asp Ser Glu Arg Asn His Val Leu Phe Ser Asp Val
        210                 215                 220

Gly Ile Cys Ile Val Leu Tyr Ala Cys Tyr Arg Ile Val Met Val Thr
225                 230                 235                 240

Gly Ala Met Ser Ala Phe Tyr Val Tyr Gly Ile Pro Trp Val Ile Met
                245                 250                 255

Ser Ala Ile Leu Phe Ala Ala Thr Tyr Leu Gln His Thr His Pro Ser
            260                 265                 270

Ile Pro His Tyr Asp Thr Thr Glu Trp Asn Trp Leu Arg Gly Ala Leu
        275                 280                 285

Ser Thr Ile Asp Arg Asp Leu Gly Phe Phe Asn Met Asn Lys Thr His
        290                 295                 300

Tyr His Val Ile His His Leu Phe Pro Val Ile Pro Glu Tyr His Ala
305                 310                 315                 320

Gln Glu Ala Thr Glu Ala Ile Lys Pro Ile Leu Gly Gln Tyr Tyr Lys
                325                 330                 335

Tyr Asp Gly Thr Pro Phe Leu Lys Ala Leu Trp Arg Glu Met Lys Asp
            340                 345                 350

Cys Ile Tyr Val Glu Ser Asp Gln Gly Gln Lys Lys Gln Gly Ile Tyr
        355                 360                 365

Trp Phe Lys Asn Lys Ile
        370

<210> SEQ ID NO 3
<211> LENGTH: 1311
<212> TYPE: DNA
<213> ORGANISM: Calendula officinalis
<220> FEATURE:
<221> NAME/KEY: CDS
<222> LOCATION: (39)..(1154)

```
<400> SEQUENCE: 3
aggaattcgg caccagccaa aaccaaagcc actatacc atg ggc aag gca gca tca        56
                                          Met Gly Lys Ala Ala Ser
                                          1               5 gcc aag aag gtt ttg gag cga gtt cca atc tca aaa ccg cca ttc gaa        104
Ala Lys Lys Val Leu Glu Arg Val Pro Ile Ser Lys Pro Pro Phe Glu
            10                  15                  20 tac aat gat ctg aag aaa gca gta cca cca cat tgt ttt tca cga cca        152
Tyr Asn Asp Leu Lys Lys Ala Val Pro Pro His Cys Phe Ser Arg Pro
        25                  30                  35 ctt tcc cga tcc ttg tat ttc ctc ttt cac gac att att gta aca tgt        200
Leu Ser Arg Ser Leu Tyr Phe Leu Phe His Asp Ile Ile Val Thr Cys
    40                  45                  50 atc ctt ttc tac gta gca tca aac tac att cat atg ctc cct cgt ttc        248
Ile Leu Phe Tyr Val Ala Ser Asn Tyr Ile His Met Leu Pro Arg Phe
55                  60                  65                  70 ctt tcc tgc atc gta tgg cct gtt tac tgg atc tcc caa gga gtt ttt        296
Leu Ser Cys Ile Val Trp Pro Val Tyr Trp Ile Ser Gln Gly Val Phe
                75                  80                  85 ctc ggc aga ttg tgg atg atc ggc cac gaa tgc ggt cat cat agc ttc        344
Leu Gly Arg Leu Trp Met Ile Gly His Glu Cys Gly His His Ser Phe
            90                  95                 100 agt aat tac cgt tgg gtc gac gat aca gtc ggt ttt cta atc cat acg        392
Ser Asn Tyr Arg Trp Val Asp Asp Thr Val Gly Phe Leu Ile His Thr
        105                 110                 115 gcc acc ctc act ccc tat ttt tcc ttc aaa tat agc cac cgt aat cac        440
Ala Thr Leu Thr Pro Tyr Phe Ser Phe Lys Tyr Ser His Arg Asn His
    120                 125                 130 cat gca cac acc aat tcc atg gaa tac gac gag gtt cat atc ccg aaa        488
His Ala His Thr Asn Ser Met Glu Tyr Asp Glu Val His Ile Pro Lys
135                 140                 145                 150 cgc aaa tca gaa gct ctc tac ttt gaa ttt ctg ggc aac aac cca atc        536
Arg Lys Ser Glu Ala Leu Tyr Phe Glu Phe Leu Gly Asn Asn Pro Ile
                155                 160                 165 ggc tta atg atc acc atg cta tgt aaa ctg act ttc gga tat gca gct        584
Gly Leu Met Ile Thr Met Leu Cys Lys Leu Thr Phe Gly Tyr Ala Ala
            170                 175                 180 tac att atg ttc aat tac aca ggt aag aag cac aaa tct ggg ggc tta        632
Tyr Ile Met Phe Asn Tyr Thr Gly Lys Lys His Lys Ser Gly Gly Leu
        185                 190                 195 gcg agc cac ttc tac cca caa agc cct ctc ttt aac gac agc gaa cgt        680
Ala Ser His Phe Tyr Pro Gln Ser Pro Leu Phe Asn Asp Ser Glu Arg
    200                 205                 210 aac cat gtt ttg ttc tct gac atc ggg att tgc atc gtc ttg tac gcg        728
Asn His Val Leu Phe Ser Asp Ile Gly Ile Cys Ile Val Leu Tyr Ala
215                 220                 225                 230 tgt tac cgt att gtg acg gtc aca ggg gca atg ccg gca ttt tat gtg        776
Cys Tyr Arg Ile Val Thr Val Thr Gly Ala Met Pro Ala Phe Tyr Val
                235                 240                 245 tac ggt att cct tgg gtt ata atg agt gct att ctc ttt gca gca act        824
Tyr Gly Ile Pro Trp Val Ile Met Ser Ala Ile Leu Phe Ala Ala Thr
            250                 255                 260 tat tta caa cac act cat cct tca atc cct cat tat gat aca acg gag        872
Tyr Leu Gln His Thr His Pro Ser Ile Pro His Tyr Asp Thr Thr Glu
        265                 270                 275 tgg aac tgg ctt aga ggg gct tta tcg aca att gat aga gat tta ggg        920
Trp Asn Trp Leu Arg Gly Ala Leu Ser Thr Ile Asp Arg Asp Leu Gly
    280                 285                 290 ttc ttc aac atg aac aaa aca cat tat cat gtt atc cac cat ttg ttt        968
```

```
Phe Phe Asn Met Asn Lys Thr His Tyr His Val Ile His His Leu Phe
295                 300                 305                 310 cct gtc att ccg gaa tac cat gca caa gag gca acc gag gcc atc aag      1016
Pro Val Ile Pro Glu Tyr His Ala Gln Glu Ala Thr Glu Ala Ile Lys
                315                 320                 325 ccc atc tta ggt caa tat tac aag tat gat ggt act ccg ttt cta aag      1064
Pro Ile Leu Gly Gln Tyr Tyr Lys Tyr Asp Gly Thr Pro Phe Leu Lys
            330                 335                 340 gcc ttg tgg aga gaa atg aag gag tgt att tat gta gaa tcc gat gaa      1112
Ala Leu Trp Arg Glu Met Lys Glu Cys Ile Tyr Val Glu Ser Asp Glu
        345                 350                 355 ggt cag aag aaa caa ggt att tat tgg ttt aaa aat aag act              1154
Gly Gln Lys Lys Gln Gly Ile Tyr Trp Phe Lys Asn Lys Thr
    360                 365                 370 tgaagtttaa cataatctgg actacgttta attttgtgcc atcagtacgt acggtgttag    1214
ttttgttgtg ttttcatttt tcgtattttg tgtgatggtg taatgtaata taattcagta    1274
taataaagga gttatccttt gatgggttta aaaaaaa                             1311
```

<210> SEQ ID NO 4
<211> LENGTH: 372
<212> TYPE: PRT
<213> ORGANISM: Calendula officinalis

<400> SEQUENCE: 4

```
Met Gly Lys Ala Ala Ser Ala Lys Lys Val Leu Glu Arg Val Pro Ile
1               5                   10                  15

Ser Lys Pro Pro Phe Glu Tyr Asn Asp Leu Lys Lys Ala Val Pro Pro
            20                  25                  30

His Cys Phe Ser Arg Pro Leu Ser Arg Ser Leu Tyr Phe Leu Phe His
        35                  40                  45

Asp Ile Ile Val Thr Cys Ile Leu Phe Tyr Val Ala Ser Asn Tyr Ile
    50                  55                  60

His Met Leu Pro Arg Phe Leu Ser Cys Ile Val Trp Pro Val Tyr Trp
65                  70                  75                  80

Ile Ser Gln Gly Val Phe Leu Gly Arg Leu Trp Met Ile Gly His Glu
                85                  90                  95

Cys Gly His His Ser Phe Ser Asn Tyr Arg Trp Val Asp Asp Thr Val
            100                 105                 110

Gly Phe Leu Ile His Thr Ala Thr Leu Thr Pro Tyr Phe Ser Phe Lys
        115                 120                 125

Tyr Ser His Arg Asn His His Ala His Thr Asn Ser Met Glu Tyr Asp
    130                 135                 140

Glu Val His Ile Pro Lys Arg Lys Ser Glu Ala Leu Tyr Phe Glu Phe
145                 150                 155                 160

Leu Gly Asn Asn Pro Ile Gly Leu Met Ile Thr Met Leu Cys Lys Leu
                165                 170                 175

Thr Phe Gly Tyr Ala Ala Tyr Ile Met Phe Asn Tyr Thr Gly Lys Lys
            180                 185                 190

His Lys Ser Gly Gly Leu Ala Ser His Phe Tyr Pro Gln Ser Pro Leu
        195                 200                 205

Phe Asn Asp Ser Glu Arg Asn His Val Leu Phe Ser Asp Ile Gly Ile
    210                 215                 220

Cys Ile Val Leu Tyr Ala Cys Tyr Arg Ile Val Thr Val Thr Gly Ala
225                 230                 235                 240

Met Pro Ala Phe Tyr Val Tyr Gly Ile Pro Trp Val Ile Met Ser Ala
```

```
                    245                 250                 255
Ile Leu Phe Ala Ala Thr Tyr Leu Gln His Thr His Pro Ser Ile Pro
                260                 265                 270

His Tyr Asp Thr Thr Glu Trp Asn Trp Leu Arg Gly Ala Leu Ser Thr
            275                 280                 285

Ile Asp Arg Asp Leu Gly Phe Phe Asn Met Asn Lys Thr His Tyr His
        290                 295                 300

Val Ile His His Leu Phe Pro Val Ile Pro Glu Tyr His Ala Gln Glu
305                 310                 315                 320

Ala Thr Glu Ala Ile Lys Pro Ile Leu Gly Gln Tyr Tyr Lys Tyr Asp
                325                 330                 335

Gly Thr Pro Phe Leu Lys Ala Leu Trp Arg Glu Met Lys Glu Cys Ile
            340                 345                 350

Tyr Val Glu Ser Asp Glu Gly Gln Lys Lys Gln Gly Ile Tyr Trp Phe
        355                 360                 365

Lys Asn Lys Thr
        370

<210> SEQ ID NO 5
<211> LENGTH: 387
<212> TYPE: PRT
<213> ORGANISM: Glycine max

<400> SEQUENCE: 5

Met Gly Leu Ala Lys Glu Thr Thr Met Gly Gly Arg Gly Arg Val Ala
1               5                   10                  15

Lys Val Glu Val Gln Gly Lys Lys Pro Leu Ser Arg Val Pro Asn Thr
            20                  25                  30

Lys Pro Pro Phe Thr Val Gly Gln Leu Lys Lys Ala Ile Pro Pro His
        35                  40                  45

Cys Phe Gln Arg Ser Leu Leu Thr Ser Phe Ser Tyr Val Val Tyr Asp
    50                  55                  60

Leu Ser Phe Ala Phe Ile Phe Tyr Ile Ala Thr Thr Tyr Phe His Leu
65                  70                  75                  80

Leu Pro Gln Pro Phe Ser Leu Ile Ala Trp Pro Ile Tyr Trp Val Leu
                85                  90                  95

Gln Gly Cys Leu Leu Thr Gly Val Trp Val Ile Ala His Glu Cys Gly
            100                 105                 110

His His Ala Phe Ser Lys Tyr Gln Trp Val Asp Asp Val Val Gly Leu
        115                 120                 125

Thr Leu His Ser Thr Leu Leu Val Pro Tyr Phe Ser Trp Lys Ile Ser
130                 135                 140

His Arg Arg His His Ser Asn Thr Gly Ser Leu Asp Arg Asp Glu Val
145                 150                 155                 160

Phe Val Pro Lys Pro Lys Ser Lys Val Ala Trp Phe Ser Lys Tyr Leu
                165                 170                 175

Asn Asn Pro Leu Gly Arg Ala Val Ser Leu Leu Val Thr Leu Thr Ile
            180                 185                 190

Gly Trp Pro Met Tyr Leu Ala Phe Asn Val Ser Gly Arg Pro Tyr Asp
        195                 200                 205

Ser Phe Ala Ser His Tyr His Pro Tyr Ala Pro Ile Tyr Ser Asn Arg
    210                 215                 220

Glu Arg Leu Leu Ile Tyr Val Ser Asp Val Ala Leu Phe Ser Val Thr
225                 230                 235                 240
```

```
Tyr Ser Leu Tyr Arg Val Ala Thr Leu Lys Gly Leu Val Trp Leu Leu
                245                 250                 255

Cys Val Tyr Gly Val Pro Leu Leu Ile Val Asn Gly Phe Leu Val Thr
            260                 265                 270

Ile Thr Tyr Leu Gln His Thr His Phe Ala Leu Pro His Tyr Asp Ser
        275                 280                 285

Ser Glu Trp Asp Trp Leu Lys Gly Ala Leu Ala Thr Met Asp Arg Asp
    290                 295                 300

Tyr Gly Ile Leu Asn Lys Val Phe His His Ile Thr Asp Thr His Val
305                 310                 315                 320

Ala His His Leu Phe Ser Thr Met Pro His Tyr His Ala Met Glu Ala
                325                 330                 335

Thr Asn Ala Ile Lys Pro Ile Leu Gly Glu Tyr Tyr Gln Phe Asp Asp
            340                 345                 350

Thr Pro Phe Tyr Lys Ala Leu Trp Arg Glu Ala Arg Glu Cys Leu Tyr
        355                 360                 365

Val Glu Pro Asp Glu Gly Thr Ser Glu Lys Gly Val Tyr Trp Tyr Arg
    370                 375                 380

Asn Lys Tyr
385

<210> SEQ ID NO 6
<211> LENGTH: 387
<212> TYPE: PRT
<213> ORGANISM: Ricinus communis

<400> SEQUENCE: 6

Met Gly Gly Gly Arg Met Ser Thr Val Ile Thr Ser Asn Asn Ser
1               5                   10                  15

Glu Lys Lys Gly Gly Ser Ser His Leu Lys Arg Ala Pro His Thr Lys
            20                  25                  30

Pro Pro Phe Thr Leu Gly Asp Leu Lys Arg Ala Ile Pro Pro His Cys
        35                  40                  45

Phe Glu Arg Ser Phe Val Arg Ser Phe Ser Tyr Val Ala Tyr Asp Val
    50                  55                  60

Cys Leu Ser Phe Leu Phe Tyr Ser Ile Ala Thr Asn Phe Phe Pro Tyr
65                  70                  75                  80

Ile Ser Ser Pro Leu Ser Tyr Val Ala Trp Leu Val Tyr Trp Leu Phe
                85                  90                  95

Gln Gly Cys Ile Leu Thr Gly Leu Trp Val Ile Gly His Glu Cys Gly
            100                 105                 110

His His Ala Phe Ser Glu Tyr Gln Leu Ala Asp Asp Ile Val Gly Leu
        115                 120                 125

Ile Val His Ser Ala Leu Leu Val Pro Tyr Phe Ser Trp Lys Tyr Ser
    130                 135                 140

His Arg Arg His His Ser Asn Ile Gly Ser Leu Glu Arg Asp Glu Val
145                 150                 155                 160

Phe Val Pro Lys Ser Lys Ser Lys Ile Ser Trp Tyr Ser Lys Tyr Ser
                165                 170                 175

Asn Asn Pro Pro Gly Arg Val Leu Thr Leu Ala Ala Thr Leu Leu Leu
            180                 185                 190

Gly Trp Pro Leu Tyr Leu Ala Phe Asn Val Ser Gly Arg Pro Tyr Asp
        195                 200                 205

Arg Phe Ala Cys His Tyr Asp Pro Tyr Gly Pro Ile Phe Ser Glu Arg
    210                 215                 220
```

```
Glu Arg Leu Gln Ile Tyr Ile Ala Asp Leu Gly Ile Phe Ala Thr Thr
225                 230                 235                 240

Phe Val Leu Tyr Gln Ala Thr Met ala Lys Gly Leu Ala Trp Val Met
            245                 250                 255

Arg Ile Tyr Gly Val Pro Leu Leu Ile Val Asn Cys Phe Leu Val Met
            260                 265                 270

Ile Thr Tyr Leu Gln His Thr His Pro Ala Ile Pro Arg Tyr Gly Ser
            275                 280                 285

Ser Glu Trp Asp Trp Leu Arg Gly Ala Met Val Thr Val Asp Arg Asp
    290                 295                 300

Tyr Gly Val Leu Asn Lys Val Phe His Asn Ile Ala Asp Thr His Val
305                 310                 315                 320

Ala His His Leu Phe Ala Thr Val Pro His Tyr His Ala Met Glu Ala
            325                 330                 335

Thr Lys Ala Ile Lys Pro Ile Met Gly Glu Tyr Tyr Arg Tyr Asp Gly
            340                 345                 350

Thr Pro Phe Tyr Lys Ala Leu Trp Arg Glu Ala Lys Glu Cys Leu Phe
            355                 360                 365

Val Glu Pro Asp Glu Gly Ala Pro Thr Gln Gly Val Phe Trp Tyr Arg
    370                 375                 380

Asn Lys Tyr
385

<210> SEQ ID NO 7
<211> LENGTH: 383
<212> TYPE: PRT
<213> ORGANISM: Impatiens balsamina

<400> SEQUENCE: 7

Met Gly Glu Val Gly Pro Thr Asn Arg Thr Lys Thr Lys Leu Asp Lys
1               5                   10                  15

Gln Gln Glu Ser Glu Asn Arg Val Pro His Glu Pro Pro Phe Thr
            20                  25                  30

Leu Ser Asp Leu Lys Lys Ala Ile Pro Pro His Cys Phe Glu Arg Ser
            35                  40                  45

Leu Val Lys Ser Phe Tyr His Val Ile His Asp Ile Ile Ile Leu Ser
    50                  55                  60

Phe Phe Tyr Tyr Val Ala Ala Asn Tyr Ile Pro Met Leu Pro Gln Asn
65                  70                  75                  80

Leu Arg Tyr Val Ala Trp Pro Ile Tyr Trp Ala Ile Gln Gly Cys Val
            85                  90                  95

Gln Leu Gly Ile Leu Val Leu Gly His Glu Cys Gly His His Ala Phe
            100                 105                 110

Ser Asp Tyr Gln Trp Val Asp Asp Met Val Gly Phe Val Leu His Ser
            115                 120                 125

Ser Gln Leu Ile Pro Tyr Phe Ser Trp Lys His Ser His Arg Arg His
    130                 135                 140

His Ser Asn Thr Ala Ser Ile Glu Arg Asp Glu Val Tyr Pro Pro Ala
145                 150                 155                 160

Tyr Lys Asn Asp Leu Pro Trp Phe Ala Lys Tyr Leu Arg Asn Pro Val
            165                 170                 175

Gly Arg Phe Leu Met Ile Phe Gly Ala Leu Leu Phe Gly Trp Pro Ser
            180                 185                 190

Tyr Leu Leu Phe Asn Ala Asn Gly Arg Leu Tyr Asp Arg Phe Ala Ser
```

-continued

```
                195                 200                 205
His Tyr Asp Pro Gln Ser Pro Ile Phe Asn Asn Arg Glu Arg Leu Gln
    210                 215                 220

Val Ile Ala Ser Asp Val Gly Leu Val Phe Ala Tyr Phe Val Leu Tyr
225                 230                 235                 240

Lys Ile Ala Leu Ala Lys Gly Phe Val Trp Leu Ile Cys Val Tyr Gly
                245                 250                 255

Val Pro Tyr Val Ile Leu Asn Gly Leu Ile Val Leu Ile Thr Phe Leu
                260                 265                 270

Gln His Thr His Pro Asn Leu Pro Arg Tyr Asp Leu Ser Glu Trp Asp
                275                 280                 285

Trp Leu Arg Gly Ala Leu Ser Thr Val Asp Arg Asp Tyr Gly Met Leu
    290                 295                 300

Asn Lys Val Phe His Asn Val Thr Asp Thr His Leu Val His His Leu
305                 310                 315                 320

Phe Thr Thr Met Pro His Tyr Arg Ala Lys Glu Ala Thr Glu Val Ile
                325                 330                 335

Lys Pro Ile Leu Gly Asp Tyr Tyr Lys Phe Asp Thr Pro Phe Leu
                340                 345                 350

Lys Ala Leu Trp Lys Asp Met Gly Lys Cys Ile Tyr Val Glu Ser Asp
                355                 360                 365

Val Pro Gly Lys Asn Lys Gly Val Tyr Trp Tyr Asn Asn Asp Ile
                370                 375                 380

<210> SEQ ID NO 8
<211> LENGTH: 399
<212> TYPE: PRT
<213> ORGANISM: Momordica charantia

<400> SEQUENCE: 8

Met Gly Gly Arg Gly Ala Ile Gly Val Leu Arg Asn Gly Gly Gly Pro
 1               5                  10                  15

Lys Lys Lys Met Gly Pro Gly Gln Gly Leu Gly Pro Gly Glu Arg Ile
                20                  25                  30

Thr His Ala Arg Pro Pro Phe Ser Ile Ser Gln Ile Lys Lys Ala Ile
            35                  40                  45

Pro Pro His Cys Phe Gln Arg Ser Leu Arg Arg Ser Phe Ser Tyr Leu
        50                  55                  60

Leu Ser Asp Ile Ala Leu Val Ser Ala Phe Tyr Tyr Val Ala Asp Thr
65                  70                  75                  80

Tyr Phe His Arg Leu Pro His Pro Leu Leu His Tyr Leu Ala Trp Pro
                85                  90                  95

Val Tyr Trp Phe Cys Gln Gly Ala Val Leu Thr Gly Met Trp Gly Ile
                100                 105                 110

Ala His Asp Cys Gly His His Ala Phe Ser Asp Tyr Gln Leu Val Asp
            115                 120                 125

Asp Val Val Gly Phe Leu Ile His Ser Leu Val Phe Val Pro Tyr Phe
        130                 135                 140

Ser Phe Lys Ile Ser His Arg Arg His His Ser Asn Thr Ser Ser Val
145                 150                 155                 160

Asp Arg Asp Glu Val Phe Val Pro Lys Pro Lys Ala Lys Met Pro Trp
                165                 170                 175

Tyr Phe Lys Tyr Leu Thr Asn Pro Pro Ala Arg Val Phe Ile Ile Phe
                180                 185                 190
```

```
Ile Thr Leu Thr Leu Gly Trp Pro Met Tyr Leu Thr Phe Asn Ile Ser
            195                 200                 205

Gly Arg Tyr Tyr Gly Arg Phe Thr Ser His Phe Asp Pro Asn Ser Pro
        210                 215                 220

Ile Phe Ser Pro Lys Glu Arg Val Leu Val His Ile Ser Asn Ala Gly
225                 230                 235                 240

Leu Val Ala Thr Gly Tyr Leu Leu Tyr Arg Ile Ala Met ala Lys Gly
                245                 250                 255

Val Gly Trp Leu Ile Arg Leu Tyr Gly Val Pro Leu Ile Val Leu Asn
            260                 265                 270

Ala Cys Val Val Leu Ile Thr Ala Leu Gln His Thr His Pro Ser Phe
            275                 280                 285

Pro Tyr Tyr Asp Ser Thr Glu Trp Asp Trp Leu Arg Gly Asn Leu Val
            290                 295                 300

Thr Val Asp Arg Asp Tyr Gly Pro Ile Met Asn Arg Val Phe His His
305                 310                 315                 320

Ile Thr Asp Thr His Val Val His His Leu Phe Pro Ser Met Pro His
                325                 330                 335

Tyr Asn Gly Lys Glu Ala Thr Val Ala Ala Lys Arg Ile Leu Gly Glu
            340                 345                 350

Tyr Tyr Gln Phe Asp Gly Thr Pro Ile Trp Lys Ala Ala Trp Arg Glu
            355                 360                 365

Phe Arg Glu Cys Val Tyr Val Glu Pro Asp Glu Asp Gly Ala Thr
370                 375                 380

Ser Gly Ser Ser Ser Lys Gly Val Phe Trp Tyr His Asn Lys Leu
385                 390                 395

<210> SEQ ID NO 9
<211> LENGTH: 387
<212> TYPE: PRT
<213> ORGANISM: Chrysobalanus icaco

<400> SEQUENCE: 9

Met Gly Ala Gly Gly Gln Lys Thr Phe Pro Arg Leu Glu Glu Glu
 1               5                  10                  15

Lys Gln Gln Gln Ala Ala Ala Gly Phe Lys Arg Ile Pro Thr Thr
            20                  25                  30

Lys Pro Pro Phe Thr Leu Ser Asp Leu Lys Lys Ala Ile Pro Pro His
            35                  40                  45

Cys Phe Gln Arg Ser Leu Leu Arg Ser Phe Ser Tyr Val Phe Ile Asp
 50                  55                  60

Leu Thr Ile Ile Ser Ile Leu Gly Tyr Ile Gly Ala Thr Tyr Ile Cys
 65                  70                  75                  80

Leu Leu Pro Pro Ser Lys Tyr Leu Ala Trp Leu Leu Tyr Trp Ala
                85                  90                  95

Val Gln Gly Cys Phe Phe Thr Gly Ala Trp Ala Leu Ala His Asp Cys
                100                 105                 110

Gly His His Ala Phe Ser Asp Tyr Gln Trp Ile Asp Asp Ala Val Gly
            115                 120                 125

Met Val Leu His Ser Thr Leu Met Val Pro Tyr Phe Ser Phe Lys Tyr
130                 135                 140

Ser His Arg Arg His Ser Asn Ile Asn Ser Leu Glu Arg Asp Glu
145                 150                 155                 160

Val Phe Val Pro Arg Pro Lys Ser Lys Ile Lys Trp Tyr Cys Ser Lys
                165                 170                 175
```

```
Tyr Leu Asn Asn Pro Leu Gly Arg Val Leu Thr Leu Ala Val Thr Leu
            180                 185                 190

Ile Leu Gly Trp Pro Met Tyr Leu Ala Leu Asn Ala Ser Gly Arg Asp
        195                 200                 205

Tyr Asp Arg Phe Val Ser His Phe Tyr Pro Tyr Gly Pro Ile Tyr Asn
    210                 215                 220

Asp Arg Glu Arg Leu Gln Ile Tyr Ile Ser Asp Ala Gly Ile Phe Ile
225                 230                 235                 240

Val Ser Tyr Val Leu Tyr Gln Val Ala Leu Ala Lys Gly Leu Pro Trp
                245                 250                 255

Leu Ile Cys Ile Tyr Gly Val Pro Leu Phe Val Asn Asn Ala Leu Val
            260                 265                 270

Val Thr Ile Thr Tyr Leu Gln His Thr His Pro Glu Leu Pro Arg Tyr
        275                 280                 285

Gly Asn Ser Glu Trp Asp Trp Phe Lys Gly Thr Leu Ala Thr Val Asp
    290                 295                 300

Arg Asp Met Gly Pro Leu Leu Asn Trp Ala Thr His His Val Ser Asp
305                 310                 315                 320

Thr His Tyr Val His His Leu Phe Ser Thr Met Pro His Tyr His Gly
                325                 330                 335

Val Glu Ala Thr Lys Ala Val Lys Pro Met Leu Gly Glu Tyr Tyr Arg
            340                 345                 350

Phe Asp Pro Thr Pro Leu Tyr Lys Ala Leu Trp Arg Glu Ala Lys Glu
        355                 360                 365

Cys Leu Phe Val Glu Pro Asp Ser Lys Ser Pro Gly Val Phe Trp Phe
    370                 375                 380

Asp Lys Phe
385

<210> SEQ ID NO 10
<211> LENGTH: 1361
<212> TYPE: DNA
<213> ORGANISM: Dimorphotheca sinuata

<400> SEQUENCE: 10
ggcacgagct acaagaaacc ttcaacaaca aaatgggagc aggaggttgc atctctgtct      60
ccgaaaccaa acccaaccaa aaaaacagtc tcgaacgagc cccttacgac aaaccgcctt     120
tcaccatcag cgacctcaaa aaagccatcc ctccccactt atttaaacgt tccttaatcc     180
gttcattatc ttacgtcgcc tctgacctca ccgtagcctt cctcctctac cacgccacca     240
cctacttcca ccacctcccg caaccgttca ccgcccctcgc atggctagct tattgggtag     300
cccaagggtg tgtgctcacc ggagtttggg tcataggcca tgaatgtggt caccatggac     360
ttagcgaata tcgaggggtt gacgacacgg ttggctacat actccactcg tctttactcg     420
tcccgtattt ctcgtggaaa tatagtcacc gtcgccacca ctccaacacc ggatcactcg     480
accgcgatga agtattcgtc ccaaaaccaa gatcaaaaat atcatggtat tcaaagtact     540
ttaacaaccc ggtcggacga atcggggttc tattcatcac gctcactctc ggctggccgt     600
tatacttaac tttcaatgtt tccggaagac cctacgaccg tttcgcgtgc cactattctc     660
ctaacagccc gatatacaac aaccgtgaac gcttccaaat ttatctttcc gatatcggga     720
tcgtcatcac gtcattagtc cttttacgtg ctgcgatggt gaaagggttg gtttggttaa     780
tttgcgtcta cggggtcccg ttaatgataa cgaacgggtt tcttgtattg gttacgtatc     840
```

-continued

```
ttcaacatac tcacccttca ttgcctcatt acgataactc ggaatgggag tggttaaagg      900
gagcattagt gactgtggac cgtgattttg gtgtgttaaa cacggtgttt catcacgcta      960
cggatggaca cattgtgcat catttgttcc caacaatacc acattataac gcgatggaag     1020
caactaaagc ggtgaagcct ttgatggggg agtattatca gtatgacgca actccgtttt     1080
atgtagcgat gtggagagag gcgaaggagt gtttgtttgt cgatcgggat gagggggaga     1140
aaggaggtgt gttttggtac aagaataaaa tgtaatgtgt gtatgtgtga gtttttagtt     1200
taggtagttt atgagtatgg ctggtgtttt tagtaatgtt gcgtgtgtgt gtgtgttcga     1260
accttgtgta tgyggttgtg tyatgtgtat gataaatgta atgtacctca ttaaaaggac     1320
ttatgttatc taaaataaga atgtktcttg ttggttatcg g                         1361
```

<210> SEQ ID NO 11
<211> LENGTH: 380
<212> TYPE: PRT
<213> ORGANISM: Dimorphotheca sinuata

<400> SEQUENCE: 11

```
Met Gly Ala Gly Gly Cys Ile Ser Val Ser Glu Thr Lys Pro Asn Gln
  1               5                  10                  15

Lys Asn Ser Leu Glu Arg Ala Pro Tyr Asp Lys Pro Pro Phe Thr Ile
             20                  25                  30

Ser Asp Leu Lys Lys Ala Ile Pro Pro His Leu Phe Lys Arg Ser Leu
         35                  40                  45

Ile Arg Ser Leu Ser Tyr Val Ala Ser Asp Leu Thr Val Ala Phe Leu
 50                  55                  60

Leu Tyr His Ala Thr Thr Tyr Phe His His Leu Pro Gln Pro Phe Thr
 65                  70                  75                  80

Ala Leu Ala Trp Leu Ala Tyr Trp Val Ala Gln Gly Cys Val Leu Thr
             85                  90                  95

Gly Val Trp Val Ile Gly His Glu Cys Gly His His Gly Leu Ser Glu
            100                 105                 110

Tyr Arg Gly Val Asp Asp Thr Val Gly Tyr Ile Leu His Ser Ser Leu
        115                 120                 125

Leu Val Pro Tyr Phe Ser Trp Lys Tyr Ser His Arg Arg His His Ser
130                 135                 140

Asn Thr Gly Ser Leu Asp Arg Asp Glu Val Phe Val Pro Lys Pro Arg
145                 150                 155                 160

Ser Lys Ile Ser Trp Tyr Ser Lys Tyr Phe Asn Asn Pro Val Gly Arg
                165                 170                 175

Ile Gly Val Leu Phe Ile Thr Leu Thr Leu Gly Trp Pro Leu Tyr Leu
            180                 185                 190

Thr Phe Asn Val Ser Gly Arg Pro Tyr Asp Arg Phe Ala Cys His Tyr
        195                 200                 205

Ser Pro Asn Ser Pro Ile Tyr Asn Asn Arg Glu Arg Phe Gln Ile Tyr
    210                 215                 220

Leu Ser Asp Ile Gly Ile Val Ile Thr Ser Leu Val Leu Arg Ala
225                 230                 235                 240

Ala Met Val Lys Gly Leu Val Trp Leu Ile Cys Val Tyr Gly Val Pro
                245                 250                 255

Leu Met Ile Thr Asn Gly Phe Leu Val Leu Val Thr Tyr Leu Gln His
            260                 265                 270

Thr His Pro Ser Leu Pro His Tyr Asp Asn Ser Glu Trp Glu Trp Leu
        275                 280                 285
```

-continued

Lys Gly Ala Leu Val Thr Val Asp Arg Asp Phe Gly Val Leu Asn Thr
            290                 295                 300

Val Phe His His Ala Thr Asp Gly His Ile Val His His Leu Phe Pro
305                 310                 315                 320

Thr Ile Pro His Tyr Asn Ala Met Glu Ala Thr Lys Ala Val Lys Pro
                325                 330                 335

Leu Met Gly Glu Tyr Tyr Gln Tyr Asp Ala Thr Pro Phe Tyr Val Ala
            340                 345                 350

Met Trp Arg Glu Ala Lys Glu Cys Leu Phe Val Asp Arg Asp Glu Gly
        355                 360                 365

Glu Lys Gly Gly Val Phe Trp Tyr Lys Asn Lys Met
    370                 375                 380

<210> SEQ ID NO 12
<211> LENGTH: 1337
<212> TYPE: DNA
<213> ORGANISM: Dimorphotheca sinuata

<400> SEQUENCE: 12
gggggatggg agcatctgag gagatgaagg tcttggaacg agttccagtc tcaaaacctc    60
cattcgagta caatgatctg aagaaagcag taccaccaca ttgttttaca cgatcacttt   120
cactctcgtt ttattacctg ttttatgacc taataaaagt atgtatcctt ttctacgtag   180
cctcaaaata cattcctatg cttccttata gcctttcctg cattgtatgg cctctttact   240
ggttcttcca aggagctttt ctaggcagat tgtggatgat tggccatgaa tgcgggcatc   300
atagctttag taattatcgt tggttagacg ataccgttgg gttcttggtc cacactgcca   360
ccctcactcc atattttct ttcaaataca gtcaccgtaa tcaccatgca cacaccaatt    420
ccttggagta tgacgaggtt catgtcccta agattaggaa atttaaatcc gaacatctct   480
actctgaatt tctcaccaac aacccatttg gcttagtggt caacatggta tttgaactca   540
cttttggata cccatcttac ttaatattca attattcagg tagaaagctt actcaagctg   600
gttttgcaag tcacttgtac ccacaaagcc caatcttcaa cgatagtgaa cgtaatcatg   660
tgttttctc tgatgttggt atttgcattg tgttatacgc attataccgc atagcgatag    720
ccaaaggcgc aatgctagtg ttgtatgtgt atggtcttcc ttgggttgta atgagtgctt   780
tcatcttttc ccttacttat ttacaacaca ctcatccttc catccctcac tatgattcaa   840
ctgagtggaa ttggctcaga ggtgctttat cctcaatcga cagagaatta gcaggggcct   900
tcaacatcaa aaaacacat tatcatgttg tgcaccattt gtttcccttt attccagaat    960
accatgcaca cgacgccacc gaggcccttaa gcccatctt aggcccatat tacaagtatg  1020
atggcactcc gttttataag gcgttgtgga gagaaatgaa ggactgtctt tatgttgaat  1080
ctgatgatgg cccccaacaaa actggtgttt actggttcaa aactaagact tgattaatca  1140
gctggcgtgt caccagcccg cccgggttcg ggttagggtt agggttaatt tcattgcagt  1200
aattttcttt ttcatttctt tttatttttc ttttatattg ttctcagtac ctgtatgttt  1260
gggttattgt gtaatgtata ataattcagt ttaataaaac cctttatatt tgatattaa   1320
aaaaaaaaaa aaaaaaa                                                 1337

<210> SEQ ID NO 13
<211> LENGTH: 375
<212> TYPE: PRT
<213> ORGANISM: Dimorphotheca sinuata

```
<400> SEQUENCE: 13

Met Gly Ala Ser Glu Glu Met Lys Val Leu Glu Arg Val Pro Val Ser
 1               5                  10                  15

Lys Pro Pro Phe Glu Tyr Asn Asp Leu Lys Lys Ala Val Pro Pro His
                 20                  25                  30

Cys Phe Thr Arg Ser Leu Ser Leu Ser Phe Tyr Tyr Leu Phe Tyr Asp
             35                  40                  45

Leu Ile Lys Val Cys Ile Leu Phe Tyr Val Ala Ser Lys Tyr Ile Pro
 50                  55                  60

Met Leu Pro Tyr Ser Leu Ser Cys Ile Val Trp Pro Leu Tyr Trp Phe
 65                  70                  75                  80

Phe Gln Gly Ala Phe Leu Gly Arg Leu Trp Met Ile Gly His Glu Cys
                 85                  90                  95

Gly His His Ser Phe Ser Asn Tyr Arg Trp Leu Asp Asp Thr Val Gly
                100                 105                 110

Phe Leu Val His Thr Ala Thr Leu Thr Pro Tyr Phe Ser Phe Lys Tyr
            115                 120                 125

Ser His Arg Asn His His Ala His Thr Asn Ser Leu Glu Tyr Asp Glu
130                 135                 140

Val His Val Pro Lys Ile Arg Lys Phe Lys Ser Glu His Leu Tyr Ser
145                 150                 155                 160

Glu Phe Leu Thr Asn Asn Pro Phe Gly Leu Val Val Asn Met Val Phe
                165                 170                 175

Glu Leu Thr Phe Gly Tyr Pro Ser Tyr Leu Ile Phe Asn Tyr Ser Gly
            180                 185                 190

Arg Lys Leu Thr Gln Ala Gly Phe Ala Ser His Leu Tyr Pro Gln Ser
        195                 200                 205

Pro Ile Phe Asn Asp Ser Glu Arg Asn His Val Phe Phe Ser Asp Val
210                 215                 220

Gly Ile Cys Ile Val Leu Tyr Ala Leu Tyr Arg Ile Ala Ile Ala Lys
225                 230                 235                 240

Gly Ala Met Leu Val Leu Tyr Val Tyr Gly Leu Pro Trp Val Val Met
                245                 250                 255

Ser Ala Phe Ile Phe Ser Leu Thr Tyr Leu Gln His Thr His Pro Ser
            260                 265                 270

Ile Pro His Tyr Asp Ser Thr Glu Trp Asn Trp Leu Arg Gly Ala Leu
        275                 280                 285

Ser Ser Ile Asp Arg Glu Leu Ala Gly Ala Phe Asn Ile Lys Lys Thr
290                 295                 300

His Tyr His Val Val His His Leu Phe Pro Phe Ile Pro Glu Tyr His
305                 310                 315                 320

Ala His Asp Ala Thr Glu Ala Leu Lys Pro Ile Leu Gly Pro Tyr Tyr
                325                 330                 335

Lys Tyr Asp Gly Thr Pro Phe Tyr Lys Ala Leu Trp Arg Glu Met Lys
            340                 345                 350

Asp Cys Leu Tyr Val Glu Ser Asp Asp Gly Pro Asn Lys Thr Gly Val
        355                 360                 365

Tyr Trp Phe Lys Thr Lys Thr
370                 375

<210> SEQ ID NO 14
<211> LENGTH: 378
<212> TYPE: PRT
<213> ORGANISM: Helianthus annuus
```

<400> SEQUENCE: 14

```
Met Gly Ala Gly Glu Tyr Thr Ser Val Thr Asn Glu Asn Asn Pro Leu
 1               5                  10                  15

Asp Arg Val Pro His Ala Lys Pro Pro Phe Thr Ile Gly Asp Leu Lys
             20                  25                  30

Lys Ala Ile Pro Pro His Cys Phe Gln Arg Ser Leu Thr Arg Ser Phe
         35                  40                  45

Ser Tyr Val Leu Ser Asp Leu Thr Ile Thr Ala Val Leu Tyr His Ile
     50                  55                  60

Ala Thr Thr Tyr Phe His His Leu Pro Thr Pro Leu Ser Ser Ile Ala
 65                  70                  75                  80

Trp Ala Ser Tyr Trp Val Val Gln Gly Cys Val Leu Thr Gly Val Trp
                 85                  90                  95

Val Ile Ala His Glu Cys Gly His His Ala Phe Ser Asp Tyr Gln Trp
             100                 105                 110

Val Asp Asp Thr Val Gly Phe Val Leu His Ser Ser Leu Leu Val Pro
         115                 120                 125

Tyr Phe Ser Trp Lys Tyr Ser His Arg His His Ser Asn Thr Gly
     130                 135                 140

Ser Leu Glu Arg Asp Glu Val Phe Val Pro Lys Ser Arg Ser Lys Val
145                 150                 155                 160

Pro Trp Tyr Ser Lys Tyr Phe Asn Asn Thr Val Gly Arg Ile Val Ser
                 165                 170                 175

Met Phe Val Thr Leu Thr Leu Gly Trp Pro Leu Tyr Leu Ala Phe Asn
             180                 185                 190

Val Ser Gly Arg Pro Tyr Asp Arg Phe Ala Cys His Tyr Val Pro Thr
         195                 200                 205

Ser Pro Met Tyr Asn Glu Arg Lys Arg Tyr Gln Ile Val Met Ser Asp
     210                 215                 220

Ile Gly Ile Val Ile Thr Ser Phe Ile Leu Tyr Arg Val Ala Met ala
225                 230                 235                 240

Lys Gly Leu Val Trp Val Ile Cys Val Tyr Gly Val Pro Leu Met Val
                 245                 250                 255

Val Asn Ala Phe Leu Val Leu Ile Thr Tyr Leu Gln His Thr His Pro
             260                 265                 270

Gly Leu Pro His Tyr Asp Ser Ser Glu Trp Glu Trp Leu Lys Gly Ala
         275                 280                 285

Leu Ala Thr Val Asp Arg Asp Tyr Gly Val Leu Asn Lys Val Phe His
     290                 295                 300

His Ile Thr Asp Thr His Val Val His His Leu Phe Ser Thr Met Pro
305                 310                 315                 320

His Tyr Asn Ala Met Glu Ala Gln Lys Ala Leu Arg Pro Val Leu Gly
                 325                 330                 335

Glu Tyr Tyr Arg Phe Asp Lys Thr Pro Phe Tyr Val Ala Met Trp Arg
             340                 345                 350

Glu Met Lys Glu Cys Leu Phe Val Glu Gln Asp Asp Glu Gly Lys Gly
         355                 360                 365

Gly Val Phe Trp Tyr Lys Asn Lys Met Asn
     370                 375
```

<210> SEQ ID NO 15
<211> LENGTH: 383
<212> TYPE: PRT

<213> ORGANISM: Borago officinalis

<400> SEQUENCE: 15

```
Met Gly Gly Gly Arg Met Pro Val Pro Thr Lys Gly Lys Lys Ser
 1               5                  10                  15

Lys Ser Asp Val Phe Gln Arg Val Pro Ser Glu Lys Pro Pro Phe Thr
                20                  25                  30

Val Gly Asp Leu Lys Lys Val Ile Pro Pro His Cys Phe Gln Arg Ser
                35                  40                  45

Val Leu His Ser Phe Ser Tyr Val Val Tyr Asp Leu Val Ile Ala Ala
            50                  55                  60

Leu Phe Phe Tyr Thr Ala Ser Arg Tyr Ile His Leu Gln Pro His Pro
 65                  70                  75                  80

Leu Ser Tyr Val Ala Trp Pro Leu Tyr Trp Phe Cys Gln Gly Ser Val
                85                  90                  95

Leu Thr Gly Val Trp Val Ile Ala His Glu Cys Gly His His Ala Phe
                100                 105                 110

Ser Asp Tyr Gln Trp Leu Asp Asp Thr Val Gly Leu Leu Leu His Ser
                115                 120                 125

Ala Leu Leu Val Pro Tyr Phe Ser Trp Lys Tyr Ser His Arg Arg His
130                 135                 140

His Ser Asn Thr Gly Ser Leu Glu Arg Asp Glu Val Phe Val Pro Lys
145                 150                 155                 160

Lys Arg Ser Gly Ile Ser Trp Ser Ser Glu Tyr Leu Asn Asn Pro Pro
                165                 170                 175

Gly Arg Val Leu Val Leu Leu Val Gln Leu Thr Leu Gly Trp Pro Leu
                180                 185                 190

Tyr Leu Met Phe Asn Val Ser Gly Arg Pro Tyr Asp Arg Phe Ala Cys
                195                 200                 205

His Phe Asp Pro Lys Ser Pro Ile Tyr Asn Asp Arg Glu Arg Leu Gln
                210                 215                 220

Ile Tyr Ile Ser Asp Ala Gly Ile Val Ala Val Met Tyr Gly Leu Tyr
225                 230                 235                 240

Arg Leu Val Ala Ala Lys Gly Val Ala Trp Val Val Cys Tyr Tyr Gly
                245                 250                 255

Val Pro Leu Leu Val Val Asn Gly Phe Leu Val Leu Ile Thr Tyr Leu
                260                 265                 270

Gln His Thr Gln Pro Ser Leu Pro His Tyr Asp Ser Ser Glu Trp Asp
                275                 280                 285

Trp Leu Lys Gly Ala Leu Ala Thr Val Asp Arg Asp Tyr Gly Phe Leu
                290                 295                 300

Asn Lys Val Leu His Asn Ile Thr Asp Thr His Val Ala His His Leu
305                 310                 315                 320

Phe Ser Thr Met Pro His Tyr His Ala Met Glu Ala Thr Lys Ala Ile
                325                 330                 335

Lys Pro Ile Leu Gly Asp Tyr Tyr Gln Cys Asp Arg Thr Pro Val Phe
                340                 345                 350

Lys Ala Met Tyr Arg Glu Val Lys Glu Cys Ile Tyr Val Glu Ala Asp
                355                 360                 365

Glu Gly Asp Asn Lys Lys Gly Val Phe Trp Tyr Lys Asn Lys Leu
                370                 375                 380
```

<210> SEQ ID NO 16
<211> LENGTH: 30

```
<212> TYPE: DNA
<213> ORGANISM: Artificial Sequence
<220> FEATURE:
<223> OTHER INFORMATION: Definition of Artificial Sequence: Calendula
      officinalis PCR primer

<400> SEQUENCE: 16
tttgagctct acacctagct acgtaccatg                                  30

<210> SEQ ID NO 17
<211> LENGTH: 30
<212> TYPE: DNA
<213> ORGANISM: Artificial Sequence
<220> FEATURE:
<223> OTHER INFORMATION: Definition of Artificial Sequence: Calendula
      officinalis PCR primer

<400> SEQUENCE: 17
tttggatcct cacggtactg atgatggcac                                  30

<210> SEQ ID NO 18
<211> LENGTH: 31
<212> TYPE: DNA
<213> ORGANISM: Artificial Sequence
<220> FEATURE:
<223> OTHER INFORMATION: Definition of Artificial Sequence: Calendula
      Fad2-1 PCR primer

<400> SEQUENCE: 18
ttgcggccgc tacacctagc tacgtaccat g                                31

<210> SEQ ID NO 19
<211> LENGTH: 30
<212> TYPE: DNA
<213> ORGANISM: Artificial Sequence
<220> FEATURE:
<223> OTHER INFORMATION: Definition of Artificial Sequence: Calendula
      Fad2-1 PCR primer

<400> SEQUENCE: 19
ttgcggccgt cacggtactg atgatggcac                                  30

<210> SEQ ID NO 20
<211> LENGTH: 24
<212> TYPE: DNA
<213> ORGANISM: Artificial Sequence
<220> FEATURE:
<223> OTHER INFORMATION: Definition of Artificial Sequence: Calendula
      Fad2-2 PCR primer

<400> SEQUENCE: 20
agcggccgct ataccatggg caag                                        24

<210> SEQ ID NO 21
<211> LENGTH: 22
<212> TYPE: DNA
<213> ORGANISM: Artificial Sequence
<220> FEATURE:
<223> OTHER INFORMATION: Definition of Artificial Sequence: Calendula
      Fad2-2 PCR primer

<400> SEQUENCE: 21
tgcggccgct atgttaaact tc                                          22

<210> SEQ ID NO 22
<211> LENGTH: 30
<212> TYPE: DNA
```

```
<213> ORGANISM: Artificial Sequence
<220> FEATURE:
<223> OTHER INFORMATION: Definition of Artificial Sequence: Calendula
      Fad2-2 PCR primer

<400> SEQUENCE: 22
tatgcggccg caaatgggag caggaggttg                              30

<210> SEQ ID NO 23
<211> LENGTH: 32
<212> TYPE: DNA
<213> ORGANISM: Artificial Sequence
<220> FEATURE:
<223> OTHER INFORMATION: Definition of Artificial Sequence: Calendula
      Fad2-2 PCR primer

<400> SEQUENCE: 23
tttgcggccg cattacatct tattcttgta cc                           32

<210> SEQ ID NO 24
<211> LENGTH: 37
<212> TYPE: DNA
<213> ORGANISM: Artificial Sequence
<220> FEATURE:
<223> OTHER INFORMATION: Definition of Artificial Sequence: Calendula
      Fad2-2 PCR primer

<400> SEQUENCE: 24
tgcggccgca atgggtggag ggatgggagc atctgag                      37

<210> SEQ ID NO 25
<211> LENGTH: 28
<212> TYPE: DNA
<213> ORGANISM: Artificial Sequence
<220> FEATURE:
<223> OTHER INFORMATION: Definition of Artificial Sequence: Calendula
      Fad2-2 PCR primer

<400> SEQUENCE: 25
tagcggccgc tgattaatca agtcttag                                28
```